United States Patent
Fukumoto et al.

(10) Patent No.: US 11,726,549 B2
(45) Date of Patent: Aug. 15, 2023

(54) PROGRAM, INFORMATION PROCESSOR, AND INFORMATION PROCESSING METHOD

(71) Applicant: SONY CORPORATION, Tokyo (JP)

(72) Inventors: Yasutaka Fukumoto, Tokyo (JP); Keita Mochizuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/045,024

(22) PCT Filed: Apr. 15, 2019

(86) PCT No.: PCT/JP2019/016150
§ 371 (c)(1),
(2) Date: Oct. 2, 2020

(87) PCT Pub. No.: WO2019/203188
PCT Pub. Date: Oct. 24, 2019

(65) Prior Publication Data
US 2021/0141443 A1 May 13, 2021

(30) Foreign Application Priority Data
Apr. 17, 2018 (JP) .................................. 2018-079335

(51) Int. Cl.
*G06F 3/01* (2006.01)
*G06T 7/246* (2017.01)
(Continued)

(52) U.S. Cl.
CPC ............ *G06F 3/011* (2013.01); *A61B 5/1114* (2013.01); *A61B 5/1122* (2013.01);
(Continued)

(58) Field of Classification Search
CPC ..... G06F 3/011; G06F 3/04815; A61B 5/744; A61B 5/1122; A61B 5/1114;
(Continued)

(56) References Cited

U.S. PATENT DOCUMENTS

2002/0103610 A1* 8/2002 Bachmann ............ A61B 5/1114
702/94
2015/0192413 A1* 7/2015 Bellusci ................ A61B 5/1114
702/152
(Continued)

FOREIGN PATENT DOCUMENTS

JP 2003259214 A 9/2003
JP 2006177749 A 7/2006
(Continued)

*Primary Examiner* — Adam R. Giesy
(74) *Attorney, Agent, or Firm* — Paratus Law Group, PLLC

(57) ABSTRACT

There is provided a program, an information processor, and an information processing method that make it possible to obtain position information for sites of a body with higher accuracy. The program causes a computer to implement a correction function of referencing a first output obtained by performing a first process on sensor data acquired by two or more motion sensors attached to two or more sites of a body and a second output obtained by performing a second process on the sensor data, and correcting position information for attachment sites to which the motion sensors are attached.

19 Claims, 36 Drawing Sheets

(51) Int. Cl.
  *G06F 3/04815* (2022.01)
  *G06T 19/00* (2011.01)
  *A61B 5/11* (2006.01)
  *A61B 5/00* (2006.01)
  *A63F 13/428* (2014.01)
  *G06T 13/40* (2011.01)
  *G01B 21/00* (2006.01)
  *A61B 5/0205* (2006.01)

(52) U.S. Cl.
  CPC ............ *A61B 5/1126* (2013.01); *A61B 5/744* (2013.01); *A63F 13/428* (2014.09); *G01B 21/00* (2013.01); *G06F 3/04815* (2013.01); *G06T 7/251* (2017.01); *G06T 13/40* (2013.01); *G06T 19/003* (2013.01); *A61B 5/0205* (2013.01); *A61B 5/7267* (2013.01); *A61B 2562/0219* (2013.01)

(58) Field of Classification Search
  CPC ............... A61B 5/1126; A61B 5/0205; A61B 2562/0219; A61B 5/7267; A63F 13/428; G06T 13/40; G06T 7/251; G06T 19/003; G01B 21/00
  See application file for complete search history.

(56) References Cited

U.S. PATENT DOCUMENTS

2017/0189752 A1* 7/2017 Mohrman ............ A61B 5/7271
2020/0060602 A1* 2/2020 Wagner ................ A61B 5/4082

FOREIGN PATENT DOCUMENTS

| JP | 2007072194 A | 3/2007 |
| JP | 2013125024 A | 6/2013 |
| JP | 2015184689 A | 10/2015 |
| JP | 2017511906 A | 4/2017 |
| WO | WO-2017043181 A1 | 3/2017 |
| WO | WO-2017217050 A1 | 12/2017 |
| WO | WO-2018051540 A | 3/2018 |

* cited by examiner

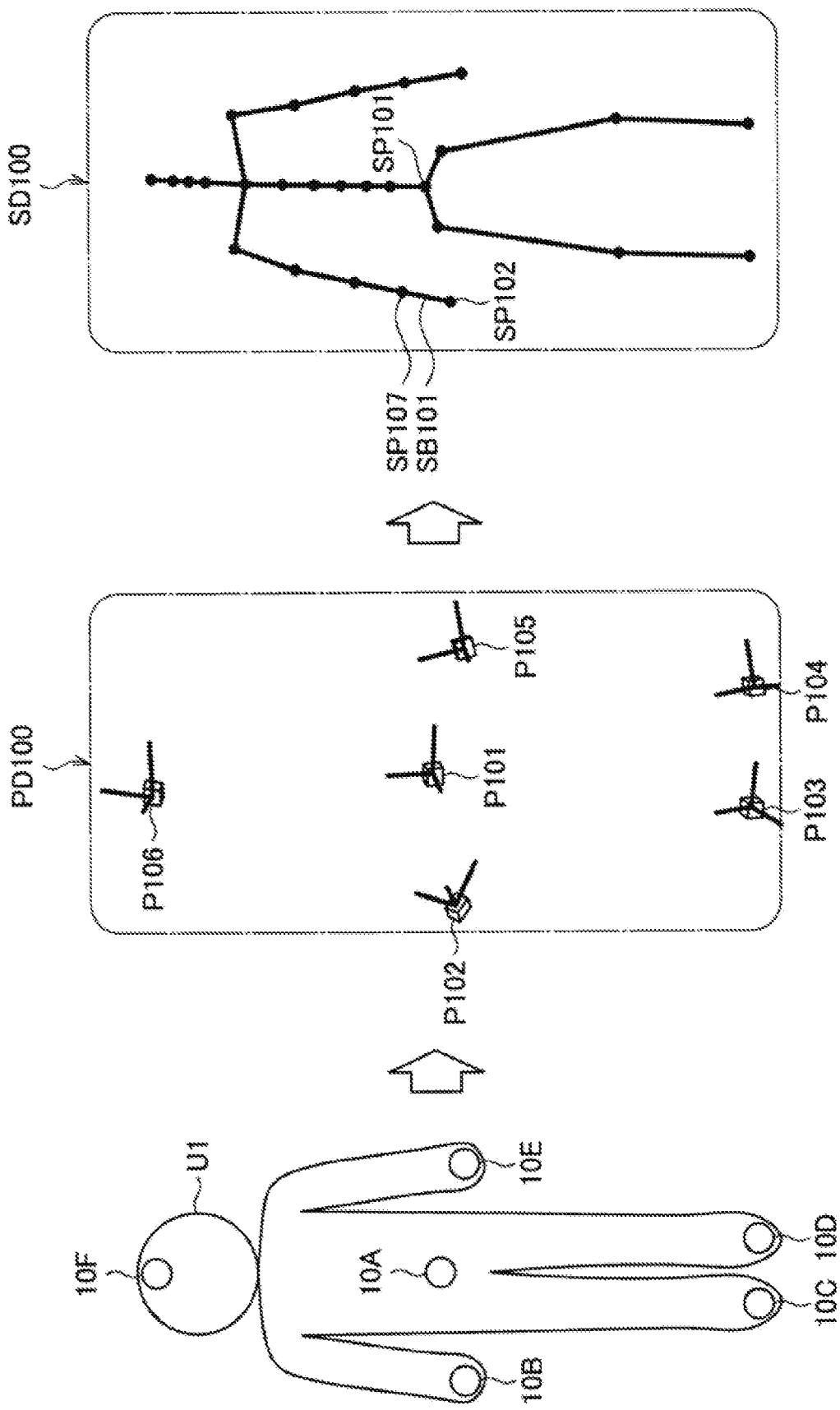

[FIG. 2]
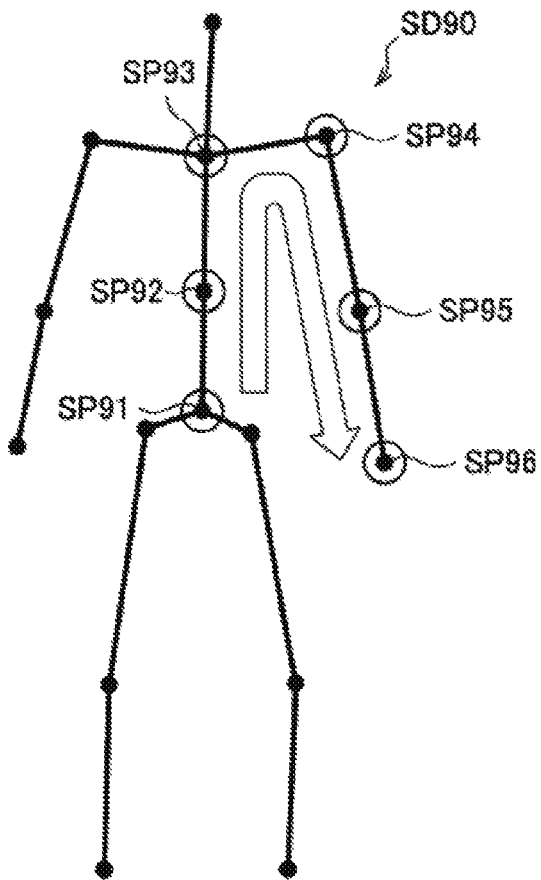
[FIG. 3]
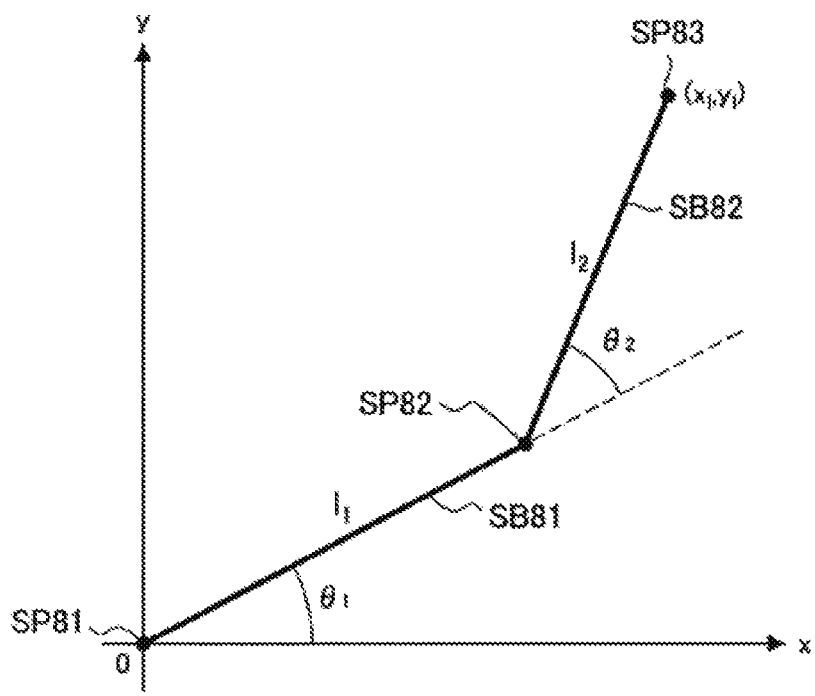

[FIG. 4]
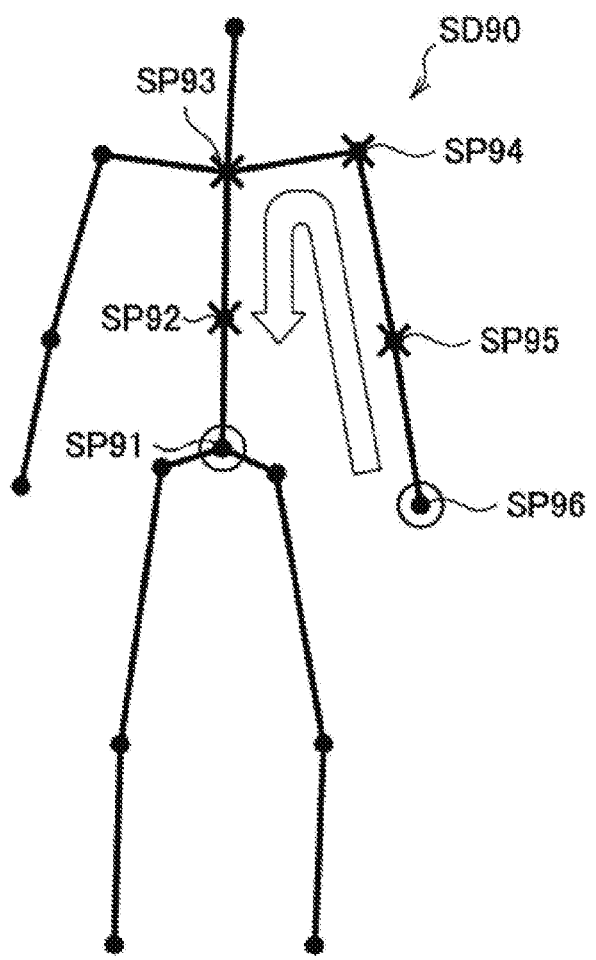

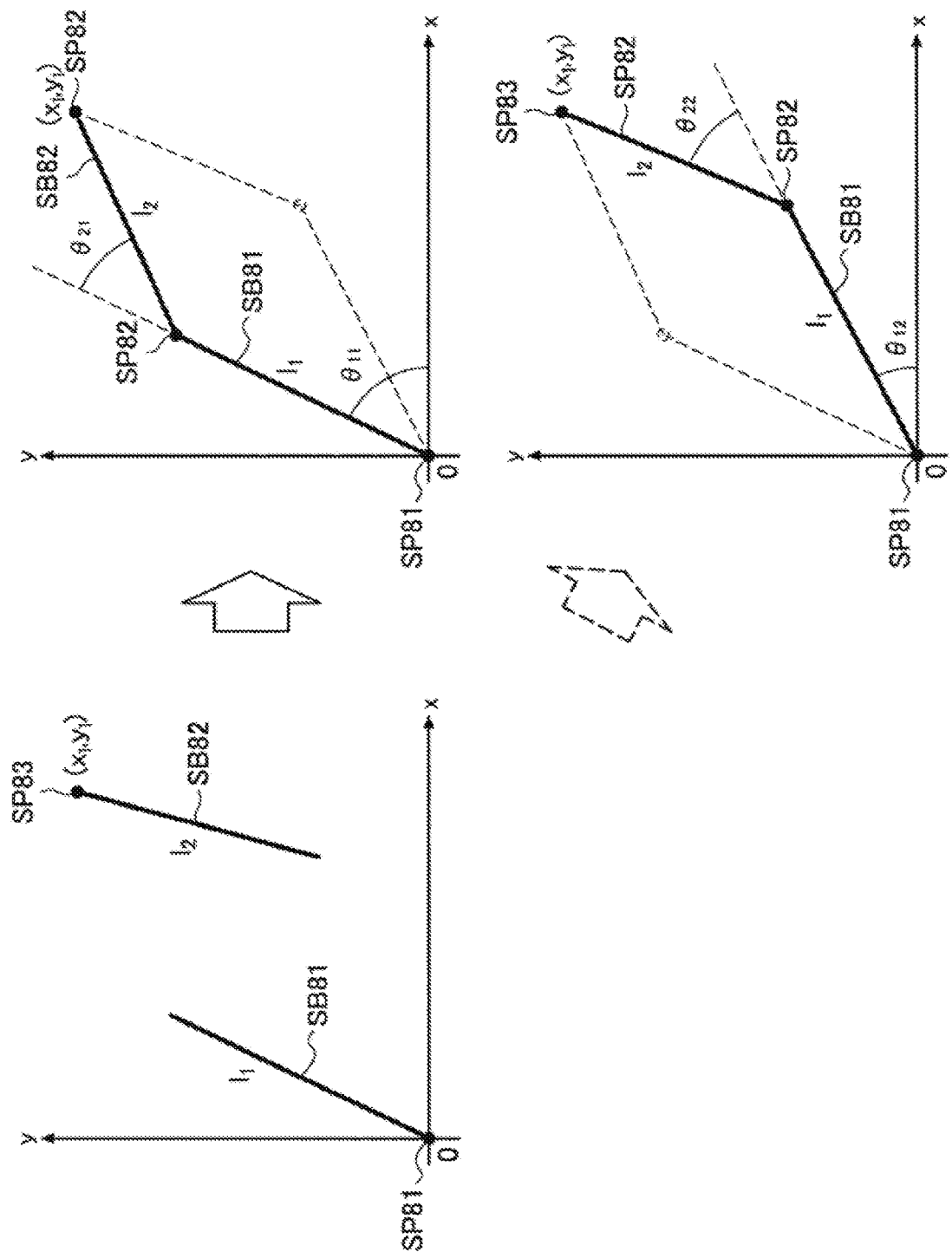
[FIG. 5]

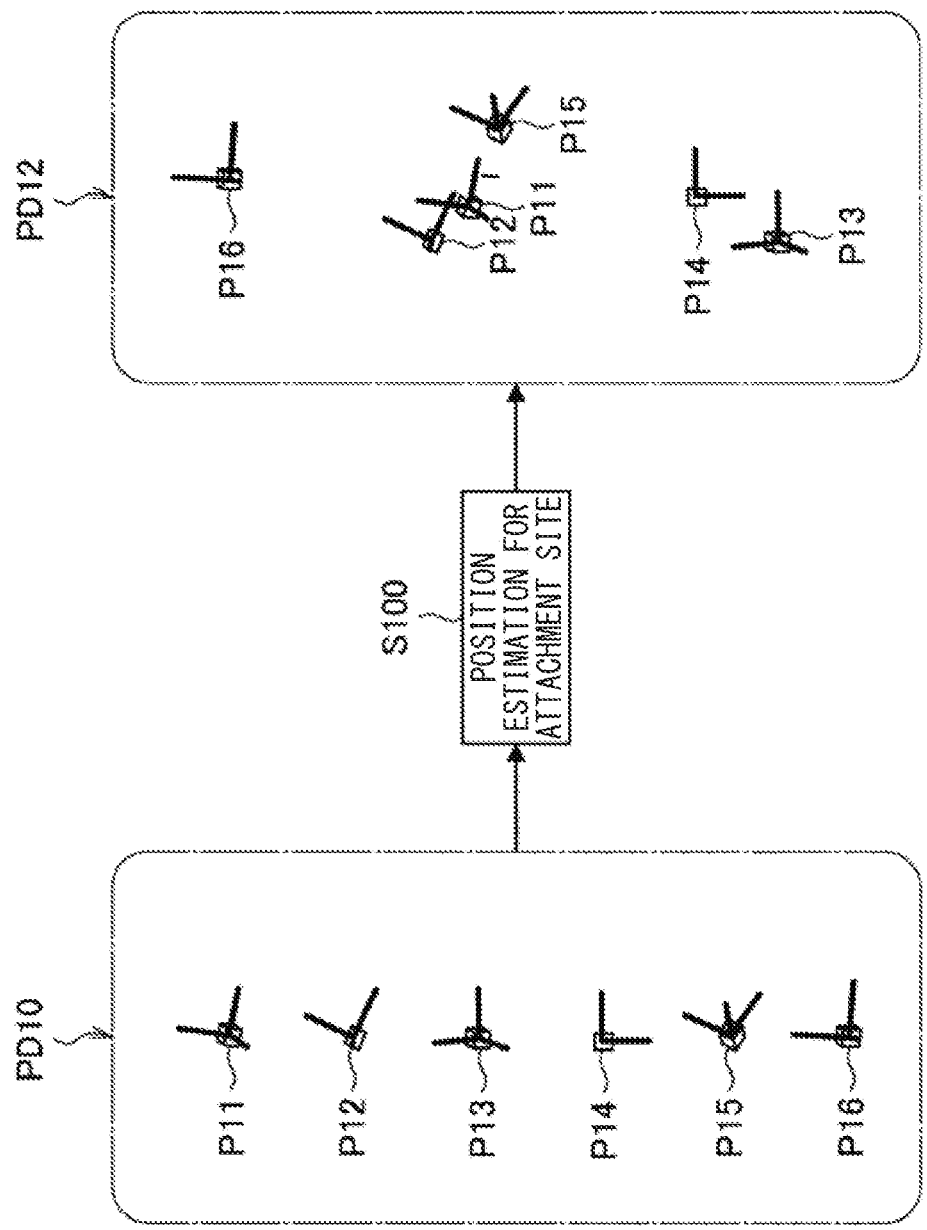
[FIG. 6]

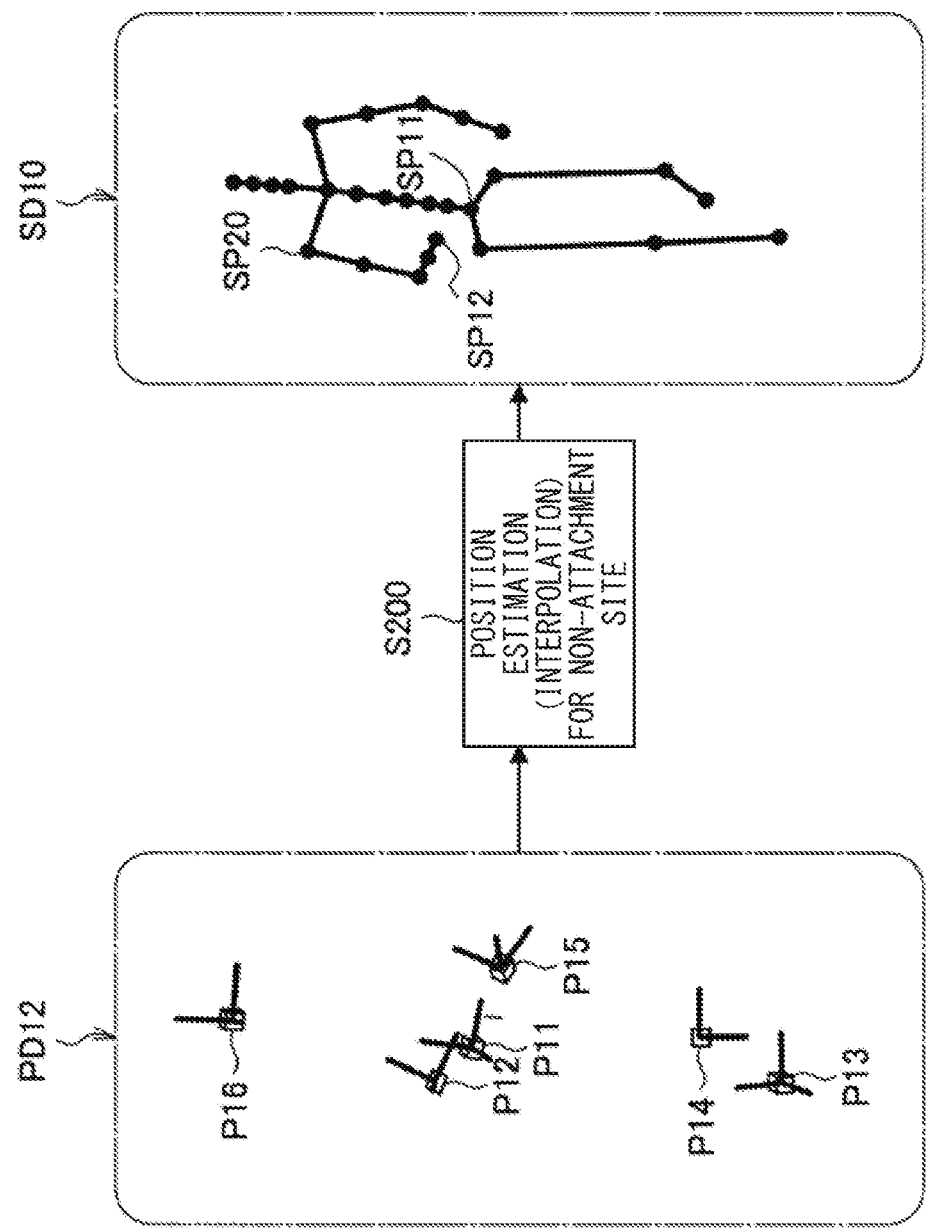
[FIG. 7]

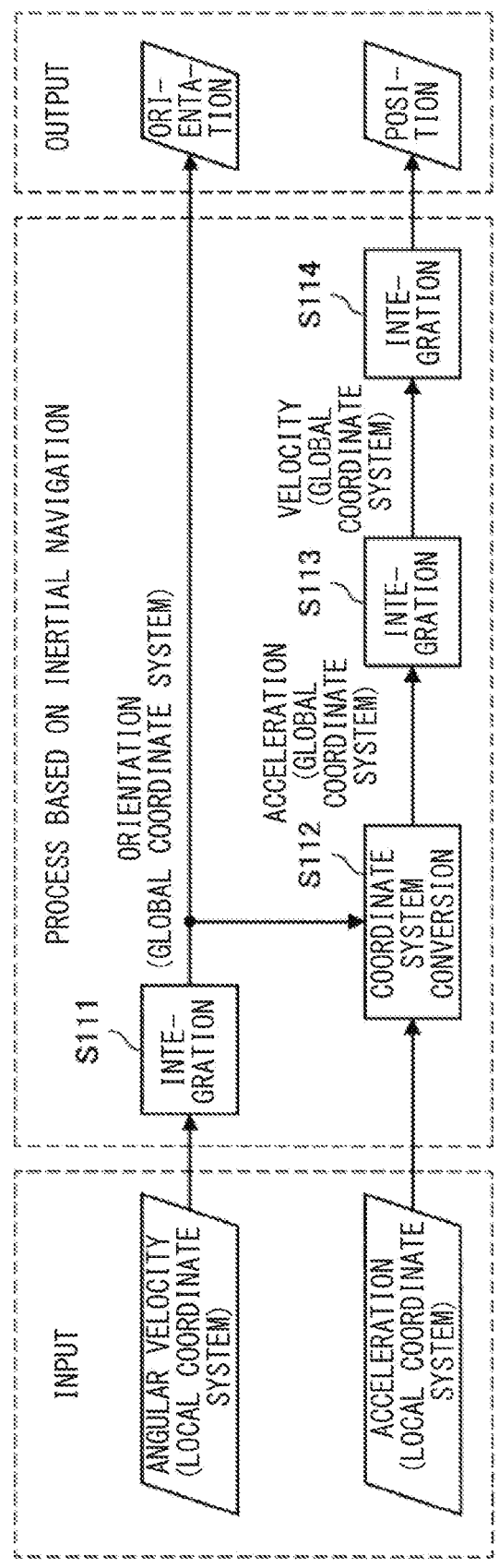
[FIG. 8]

[ FIG. 9 ]
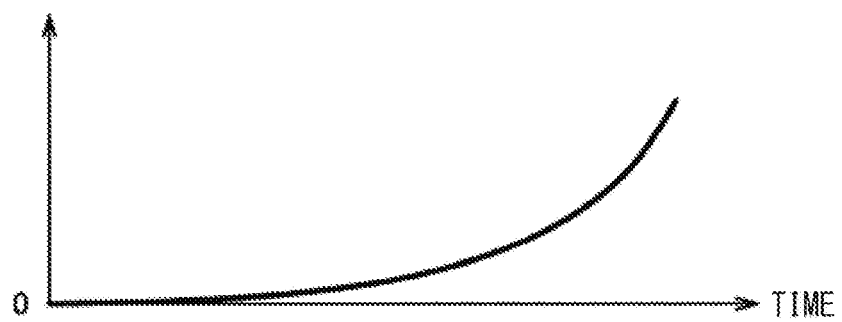

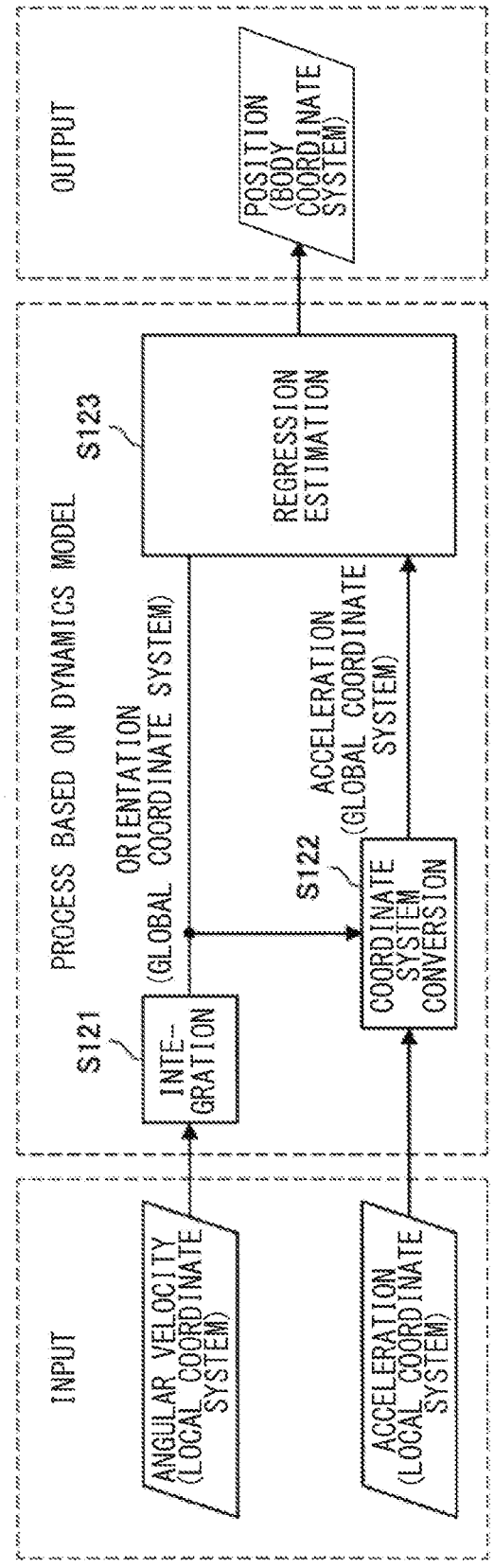
[FIG. 10]

[ FIG. 11 ]
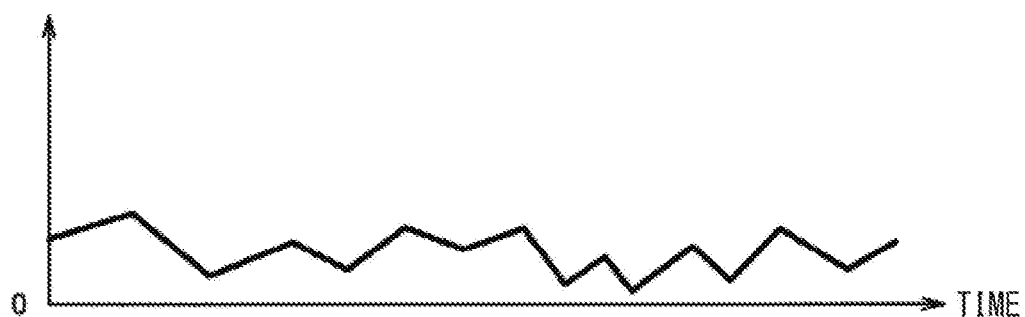

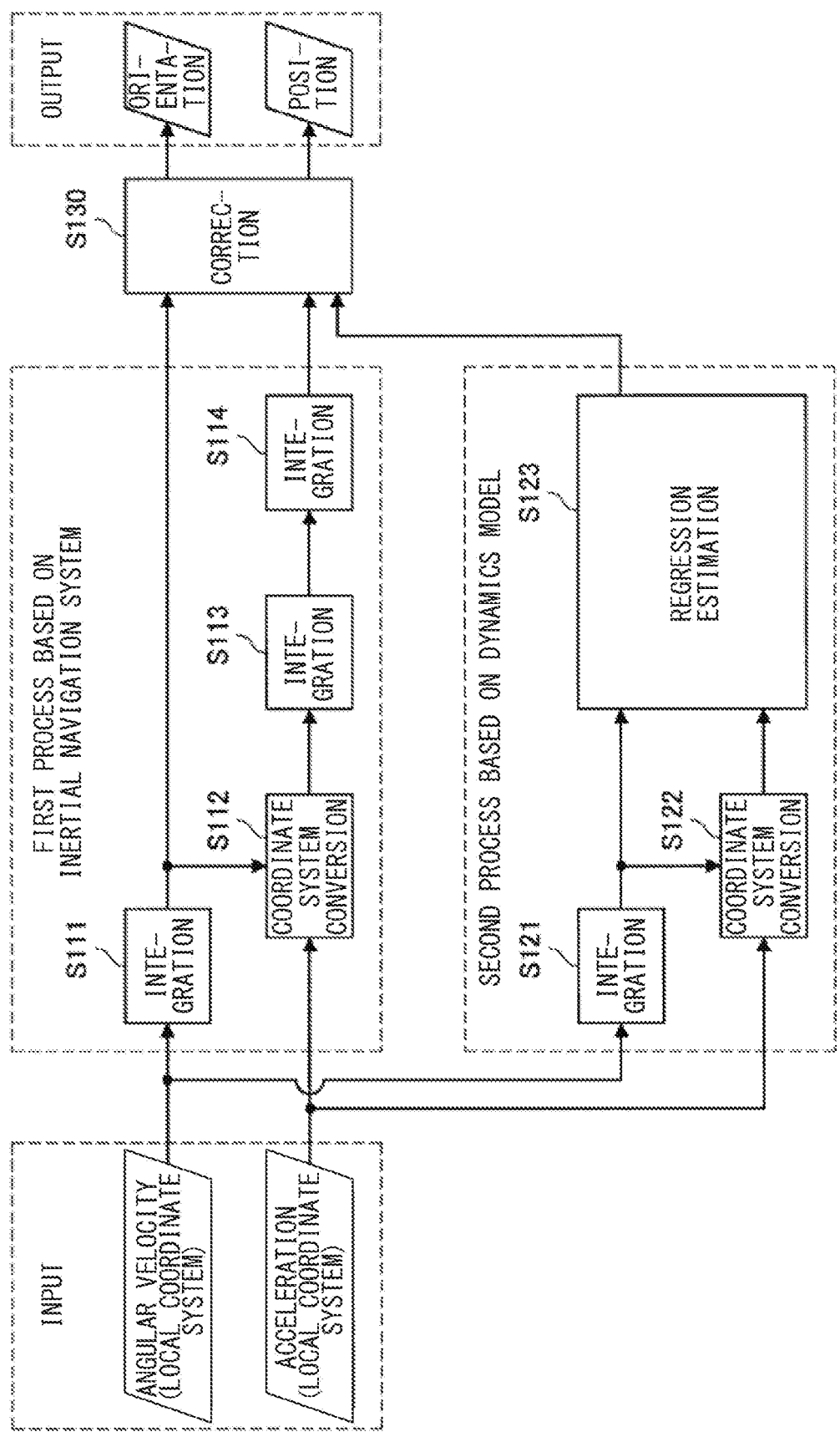
[FIG. 12]

[FIG. 13]
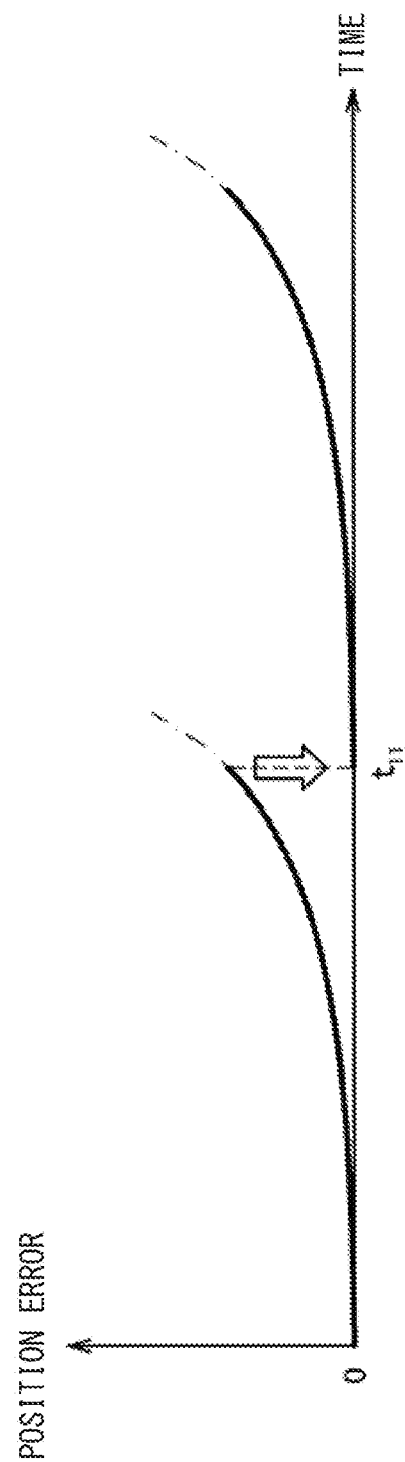

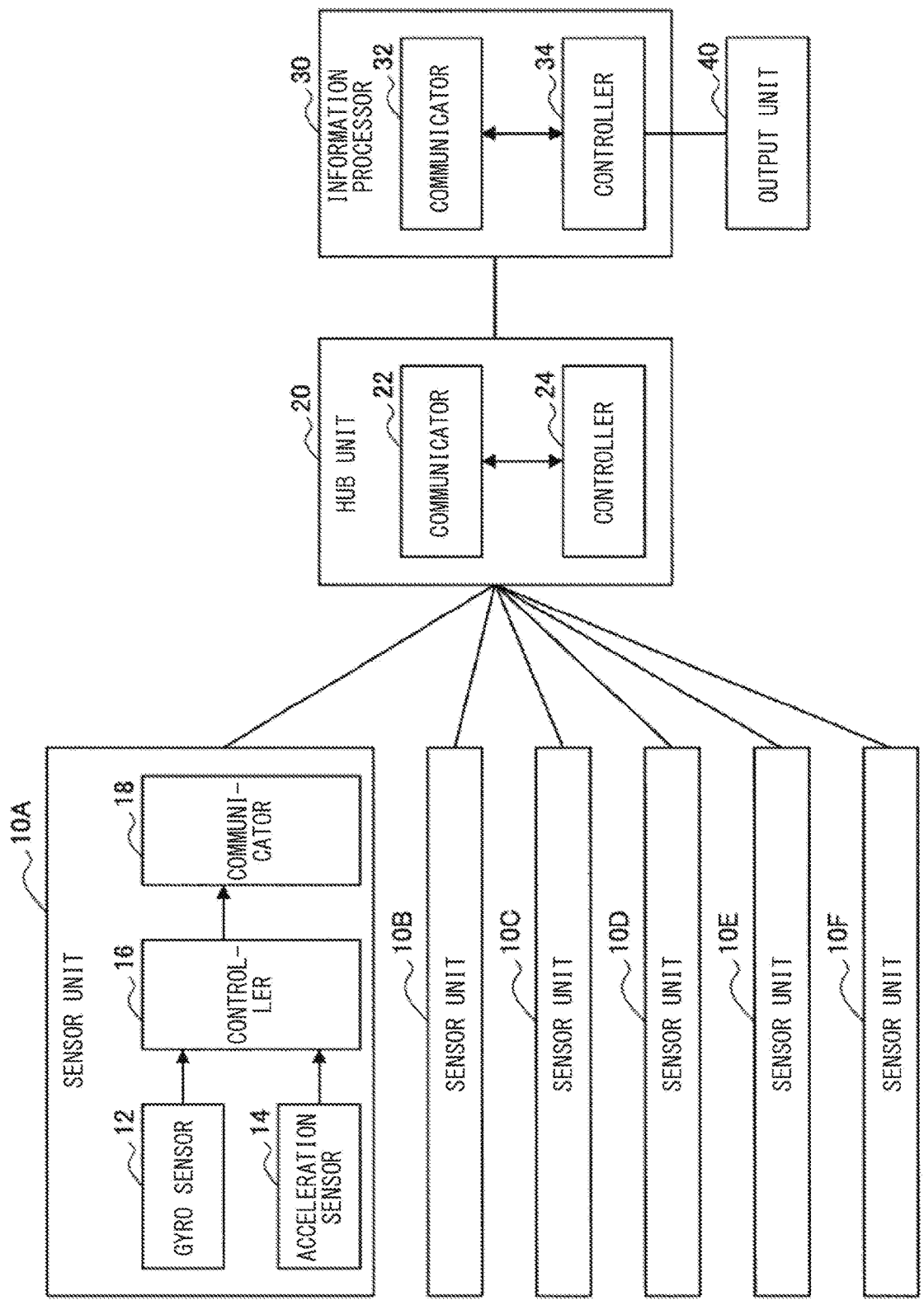
[FIG. 14]

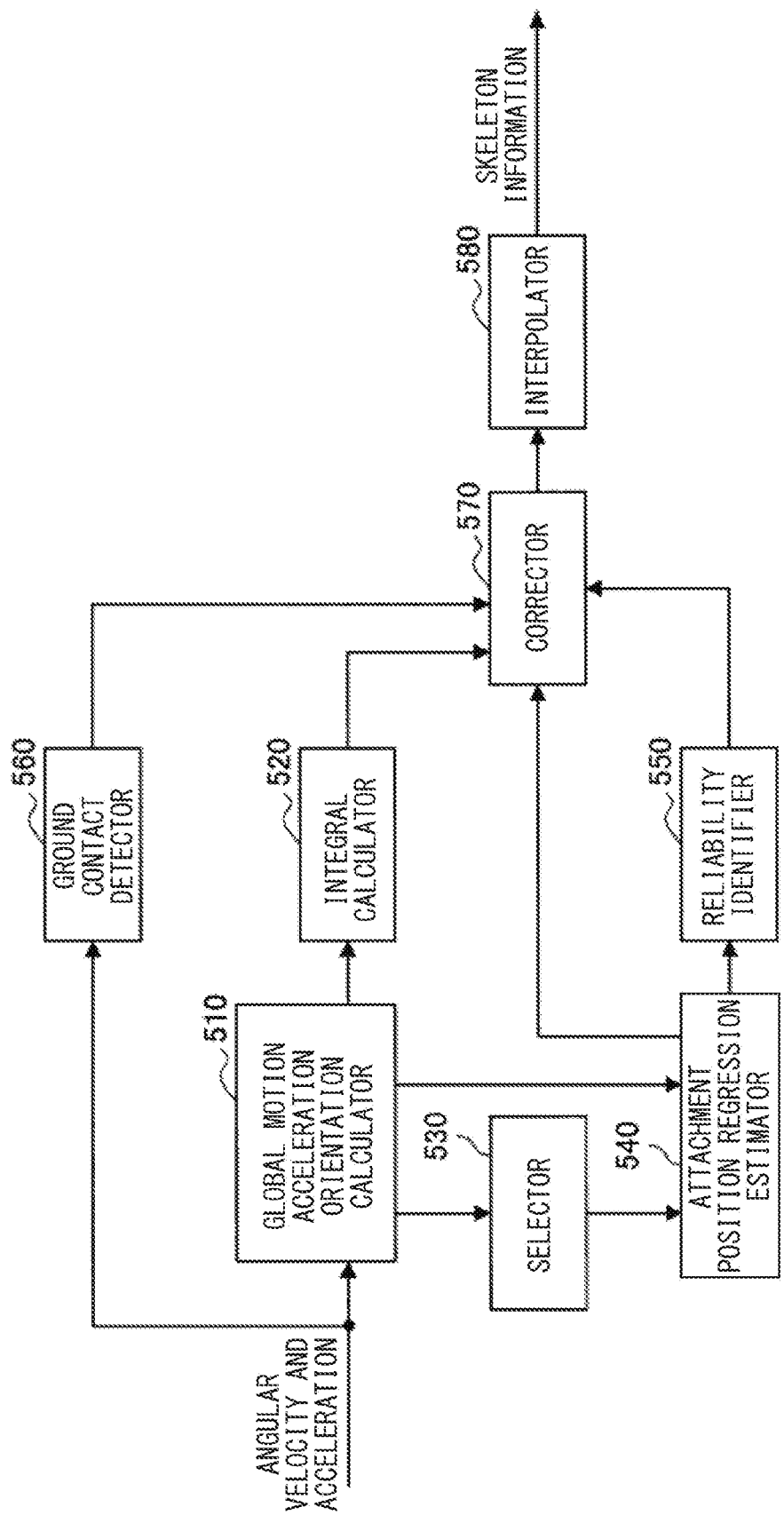
[FIG. 15]

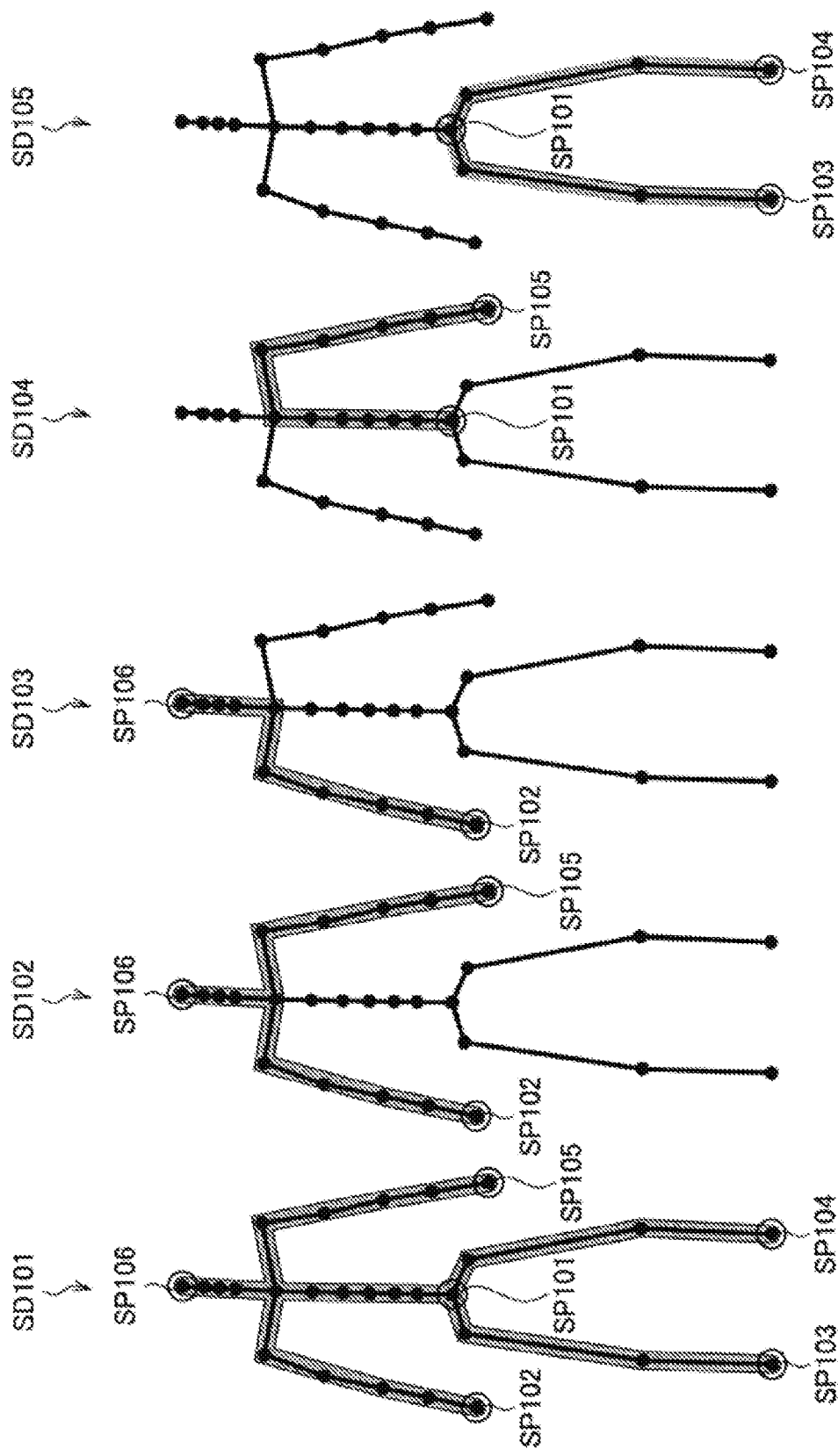
[FIG. 16]

[ FIG. 17 ]
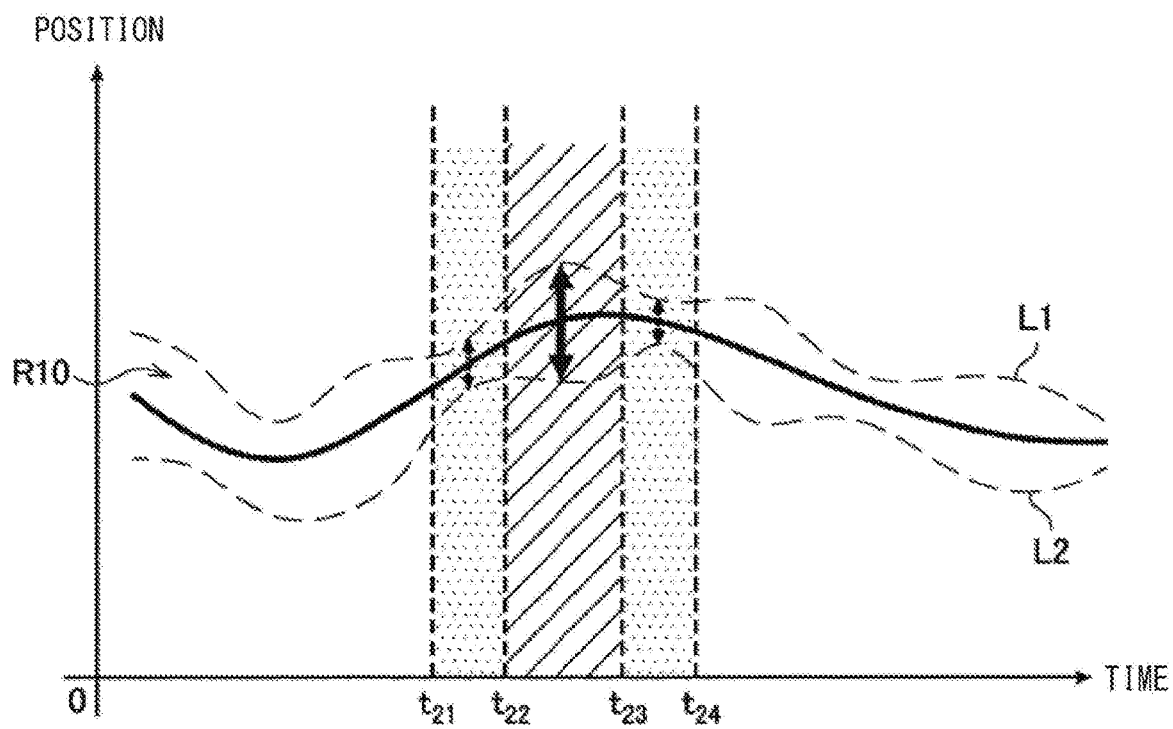

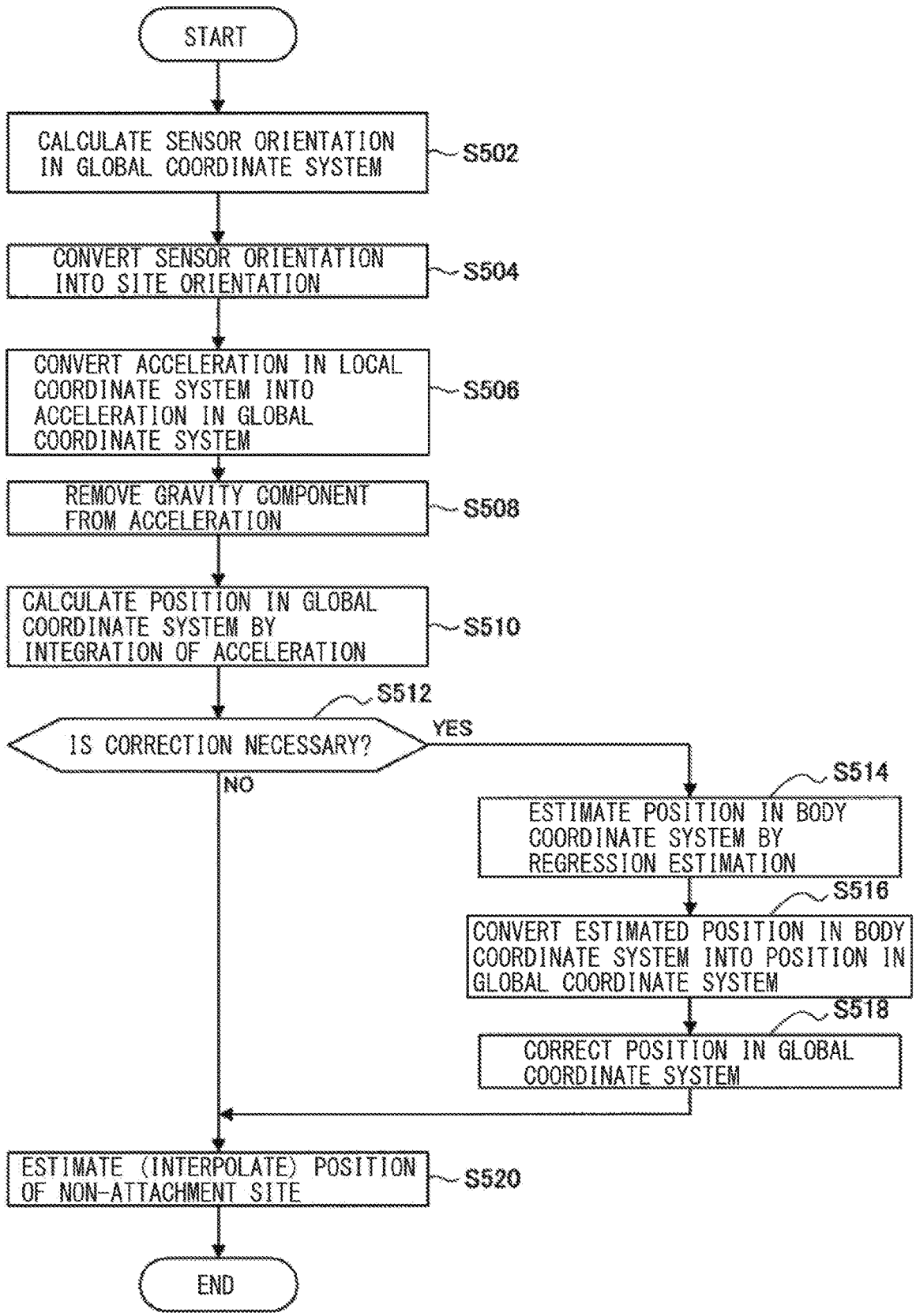
[FIG. 18]

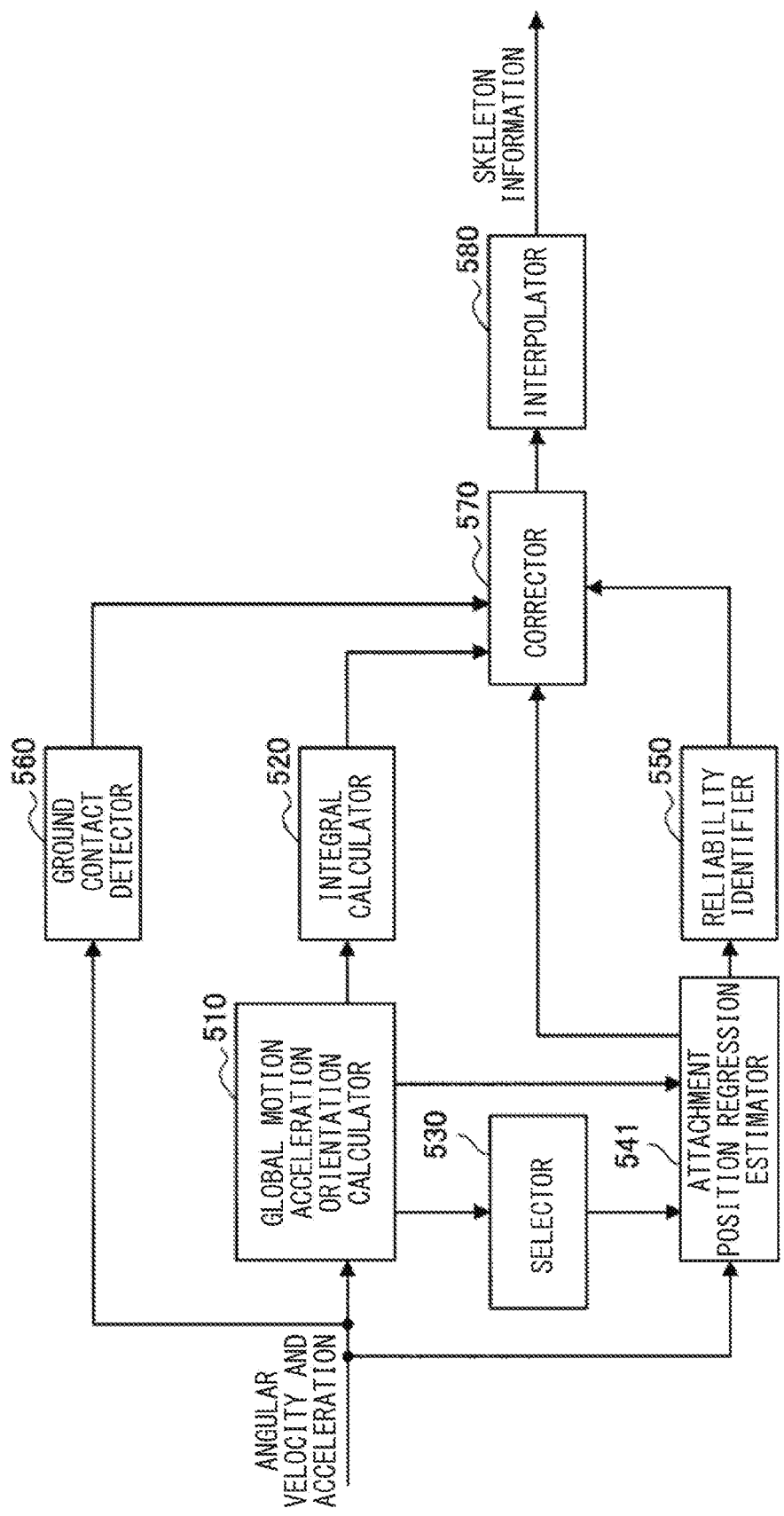
[FIG. 19]

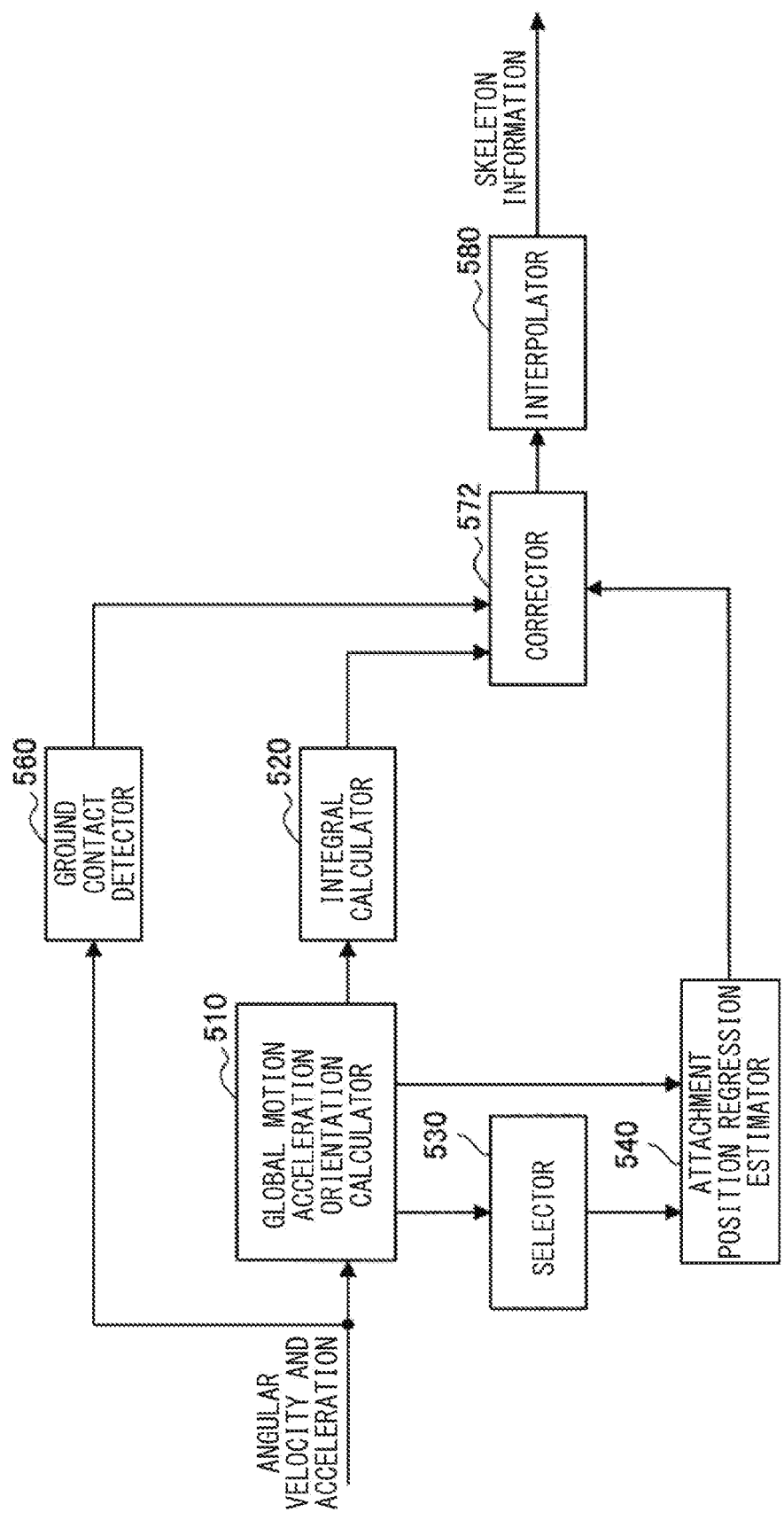
[FIG. 20]

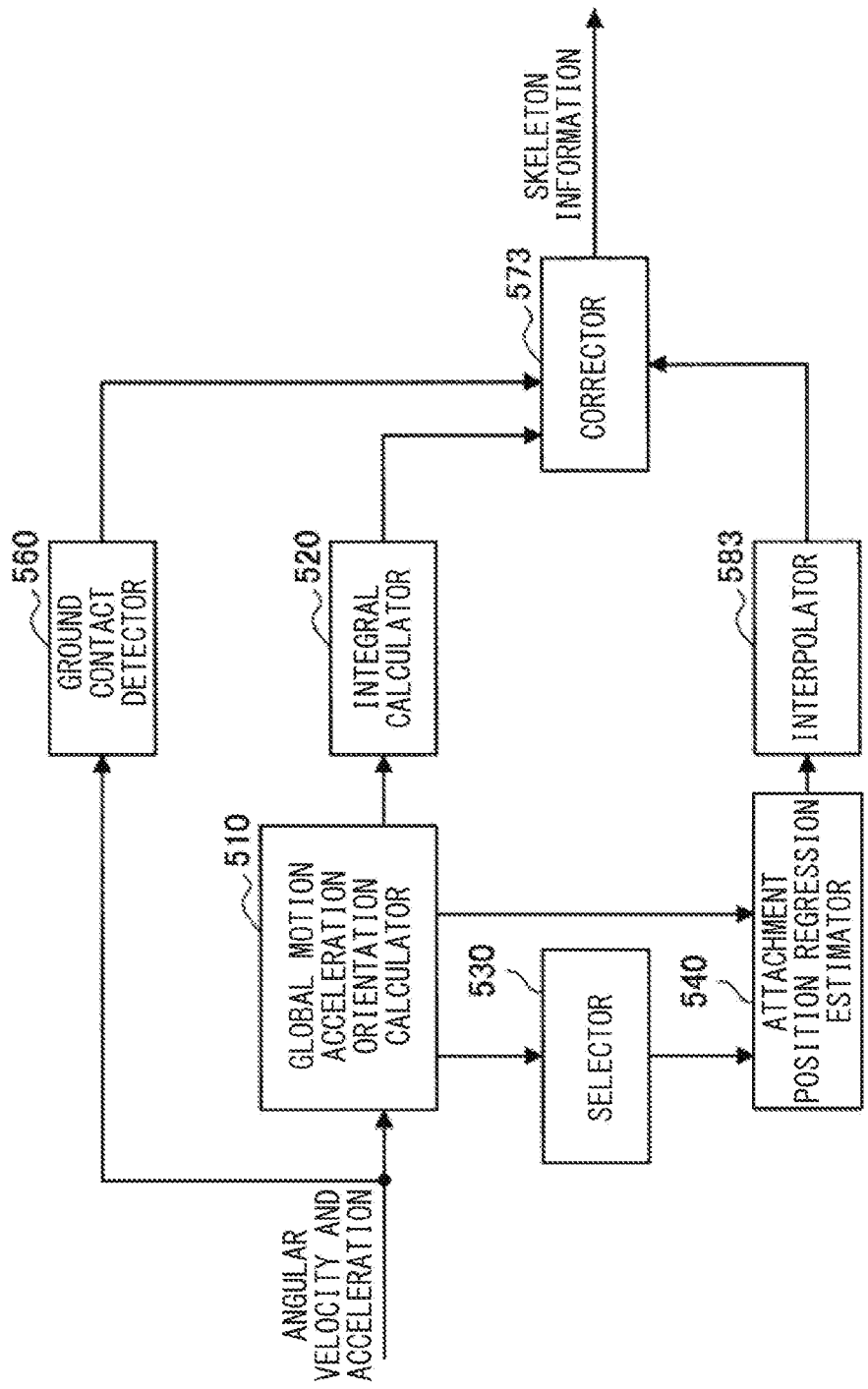
[FIG. 21]

[ FIG. 22 ]
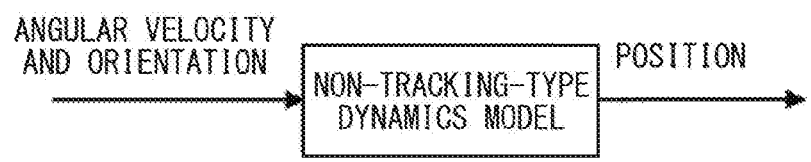
[ FIG. 23 ]
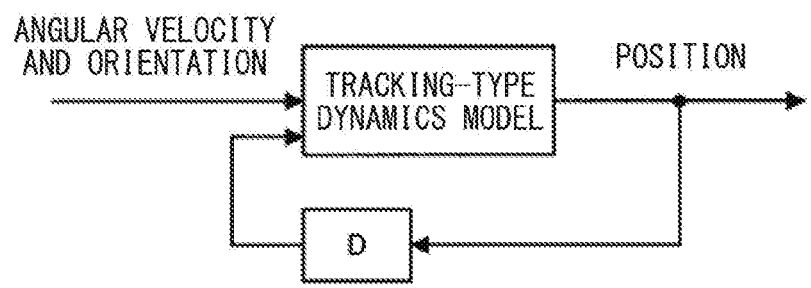

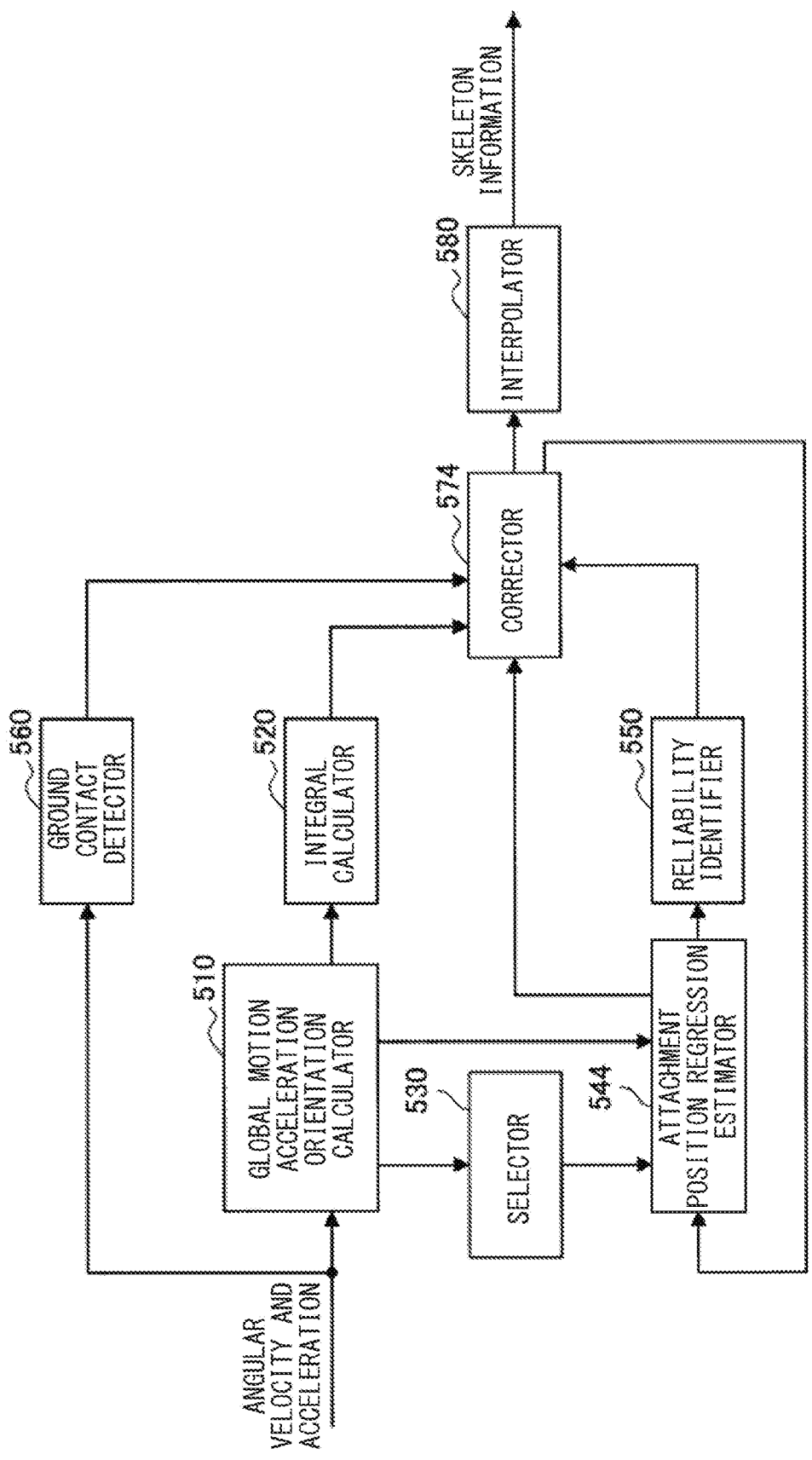

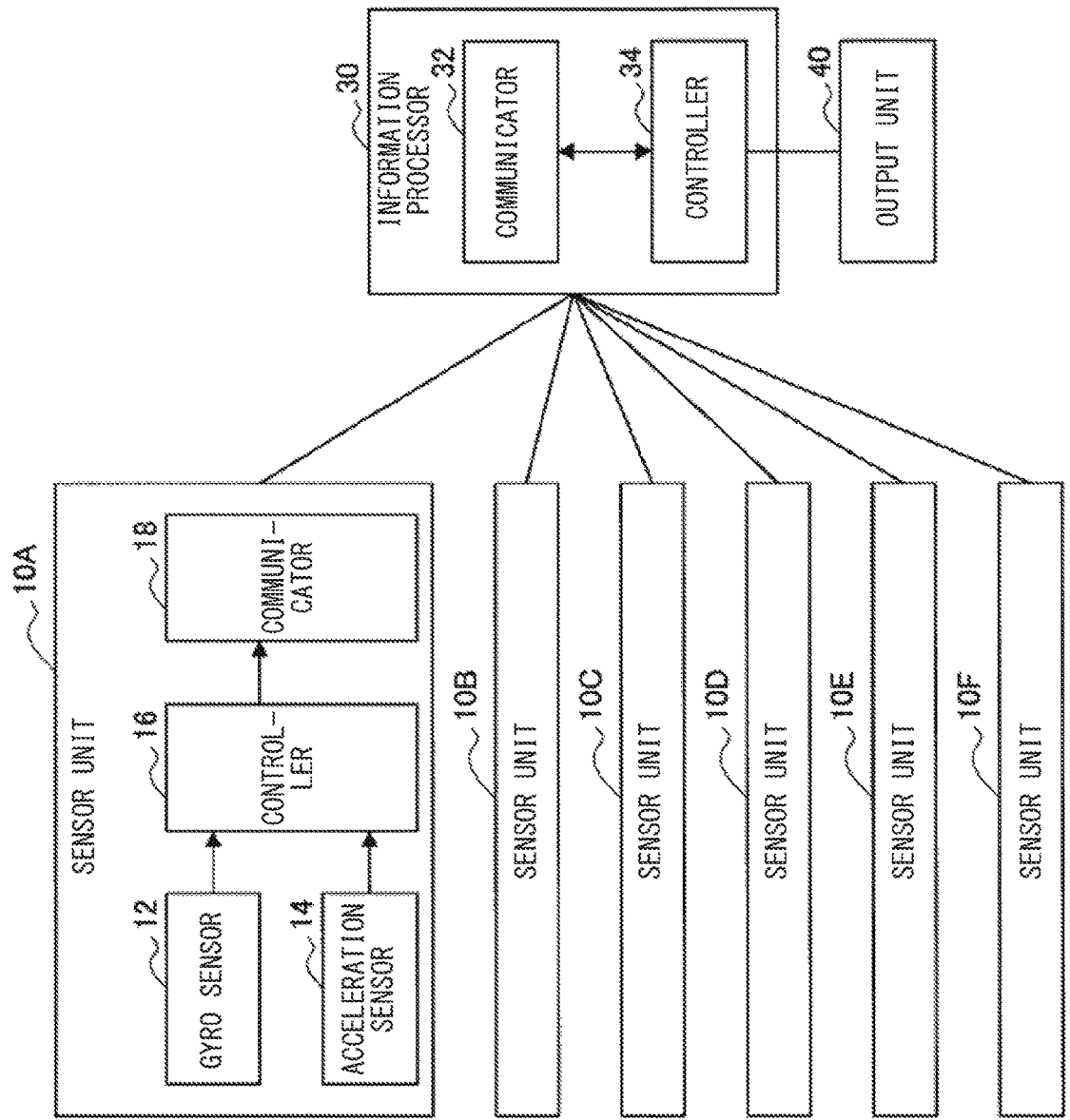
[FIG. 25]

[ FIG. 26 ]
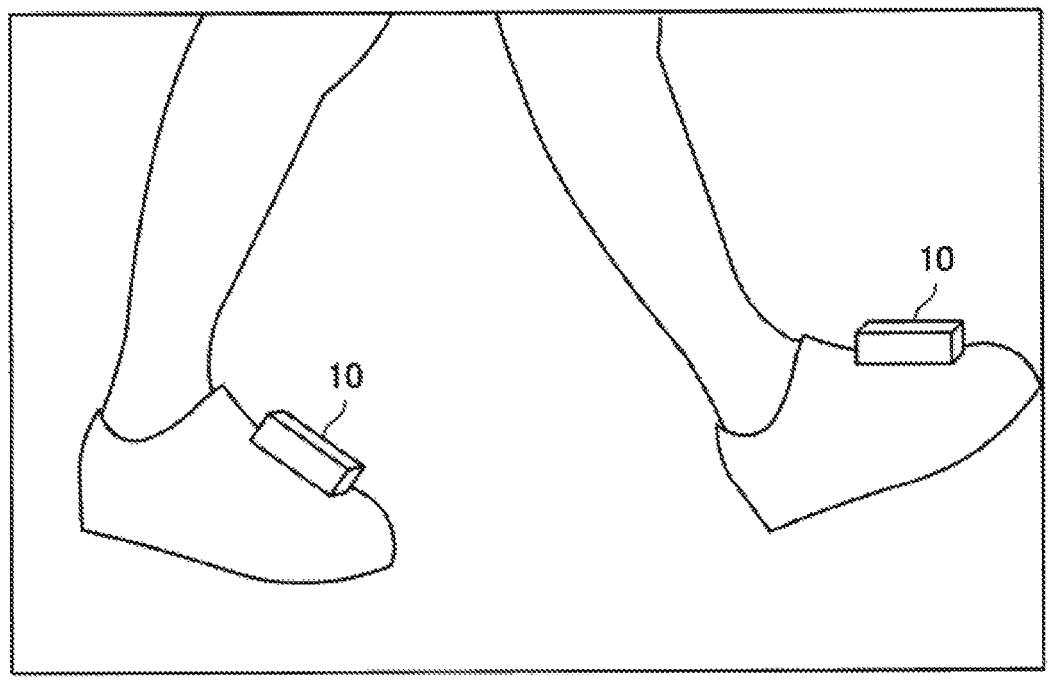

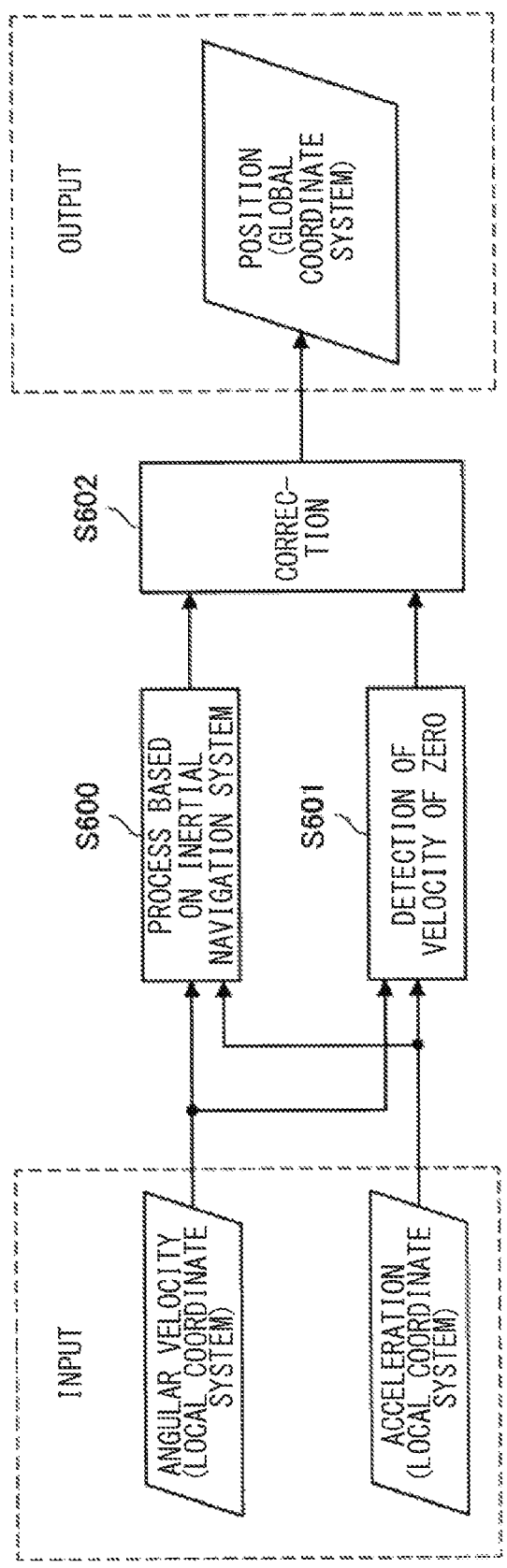
[FIG. 27]

[ FIG. 28 ]
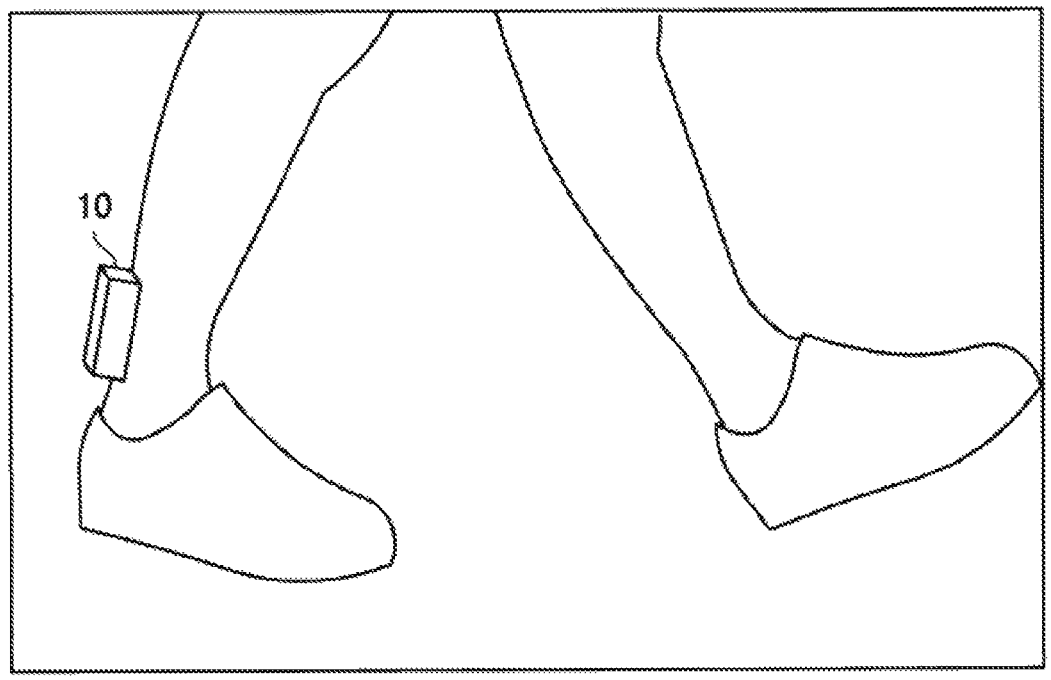

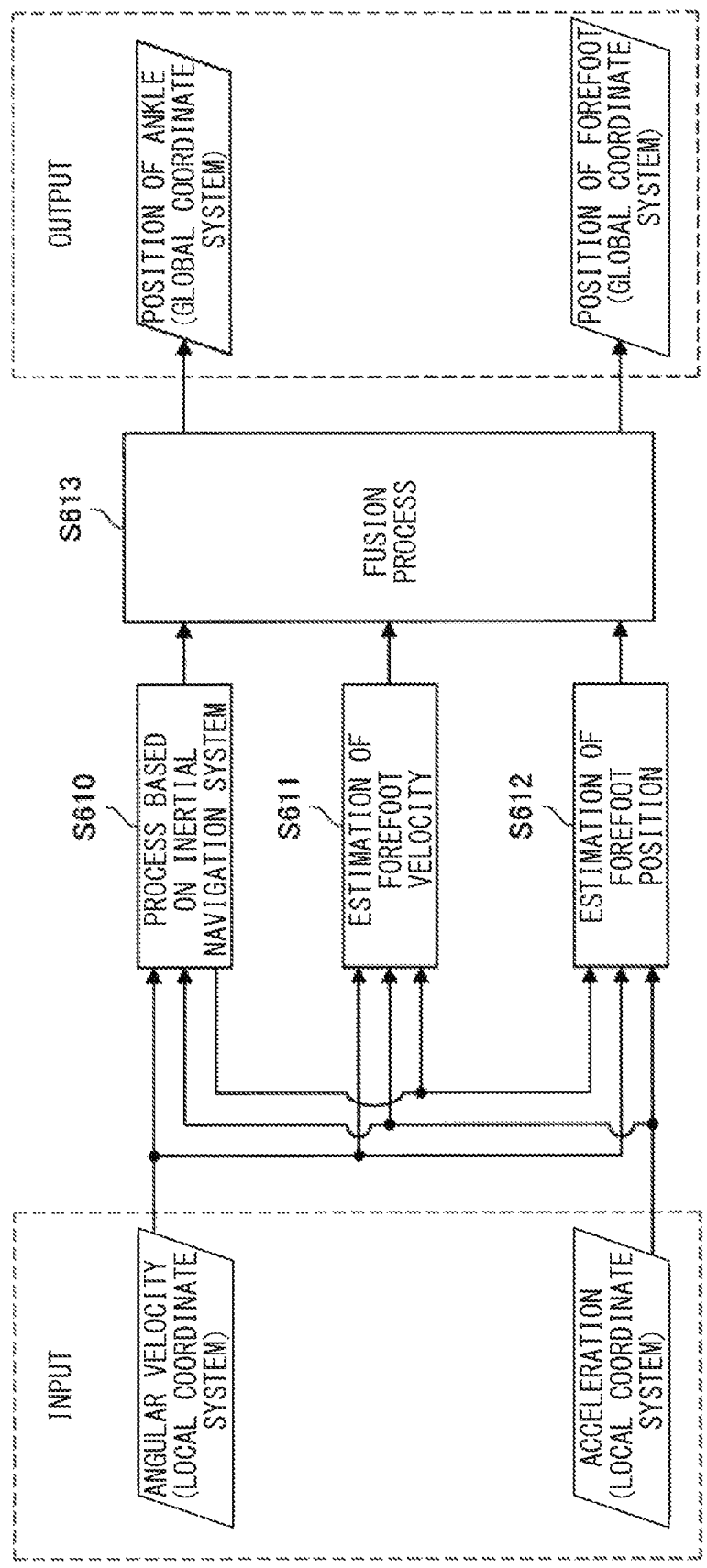
[FIG. 29]

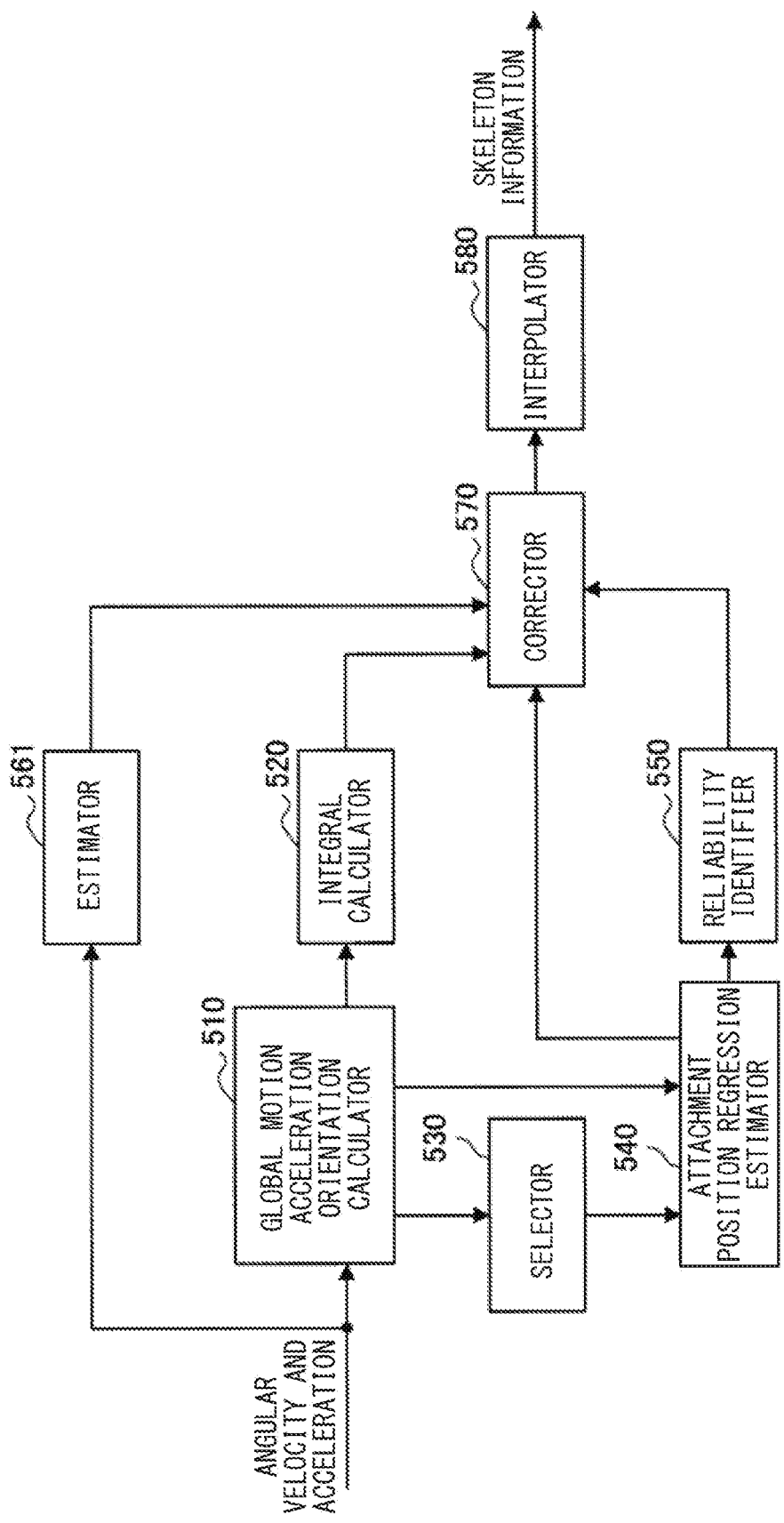

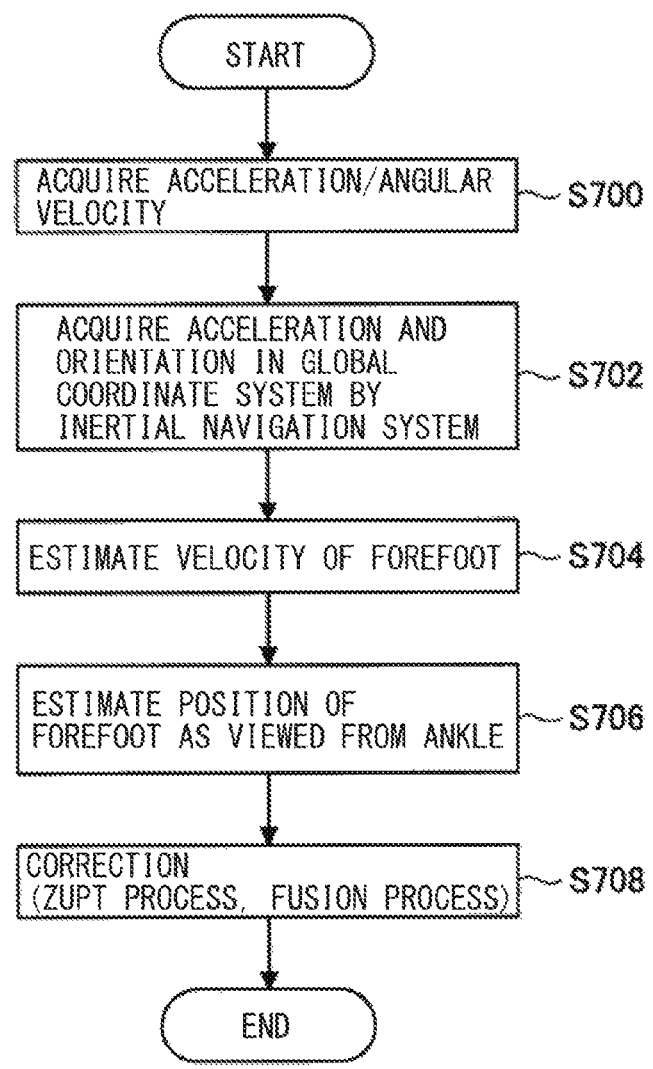
[FIG. 31]

[ FIG. 32 ]
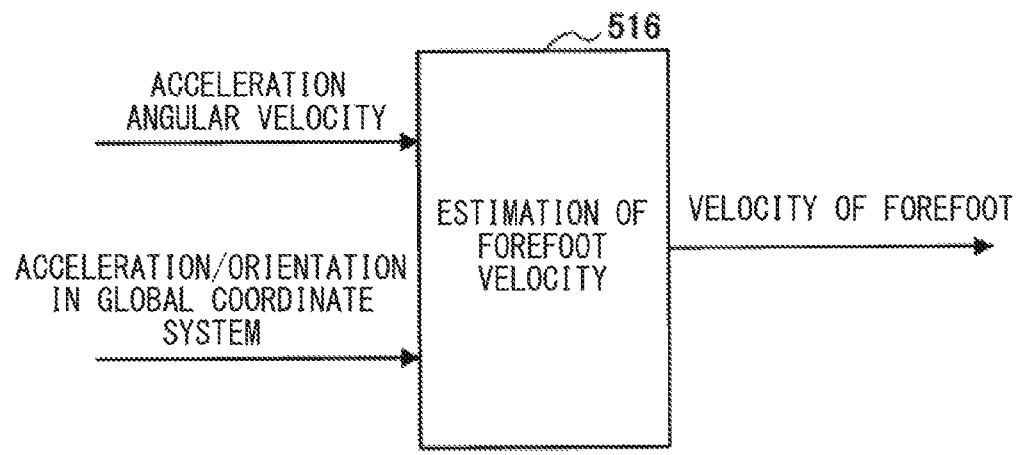
[ FIG. 33 ]
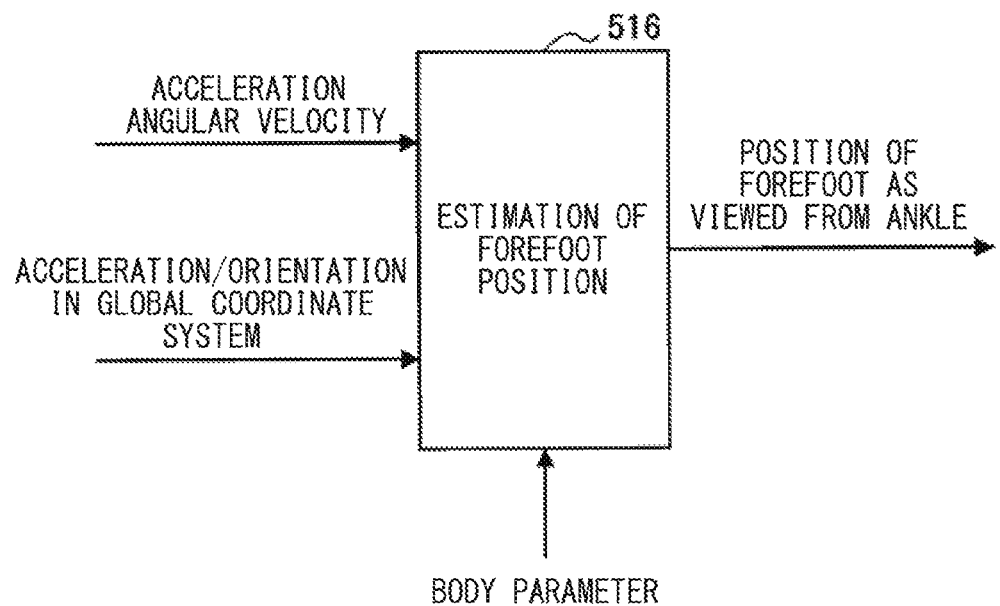

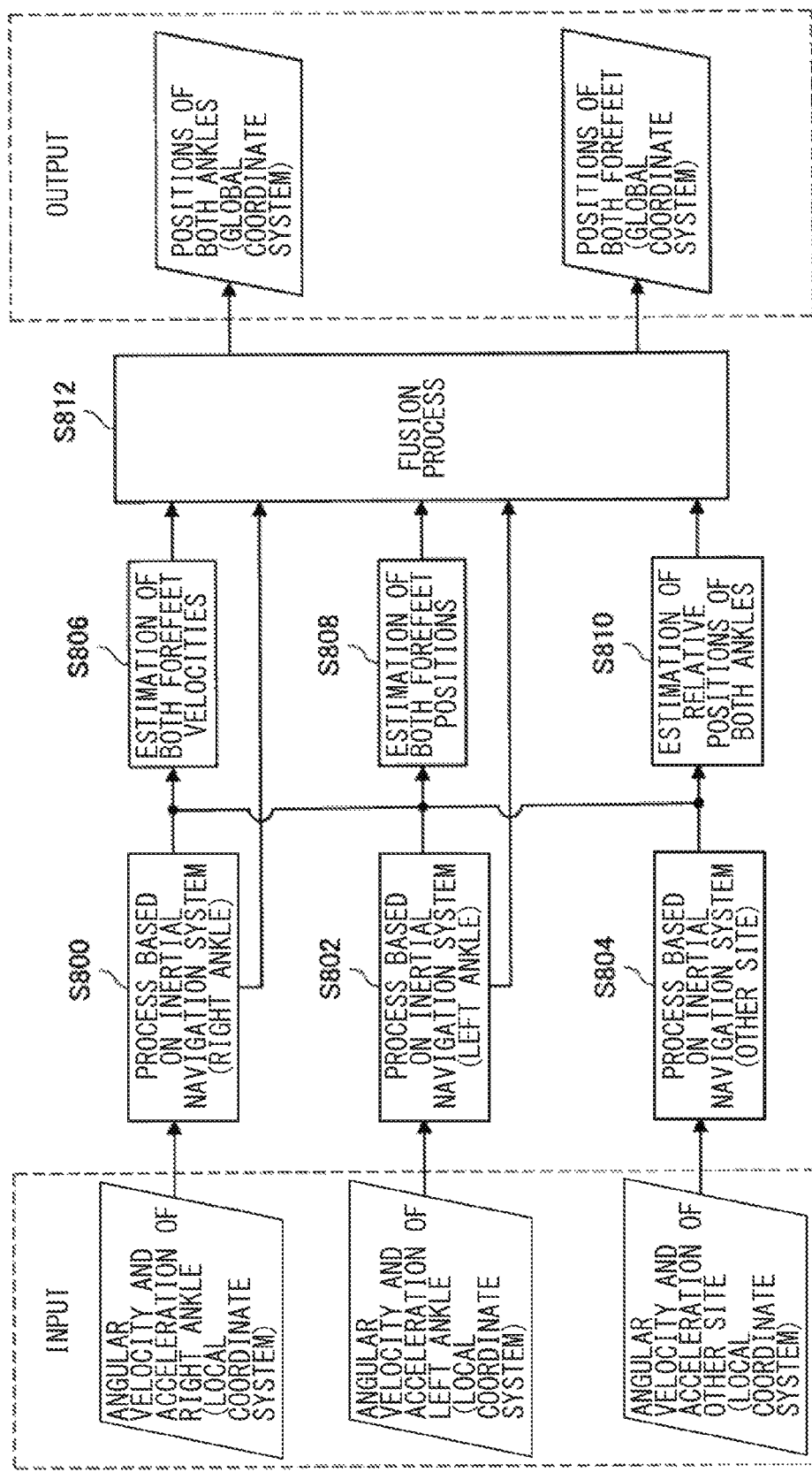
[FIG. 34]

[FIG. 35]
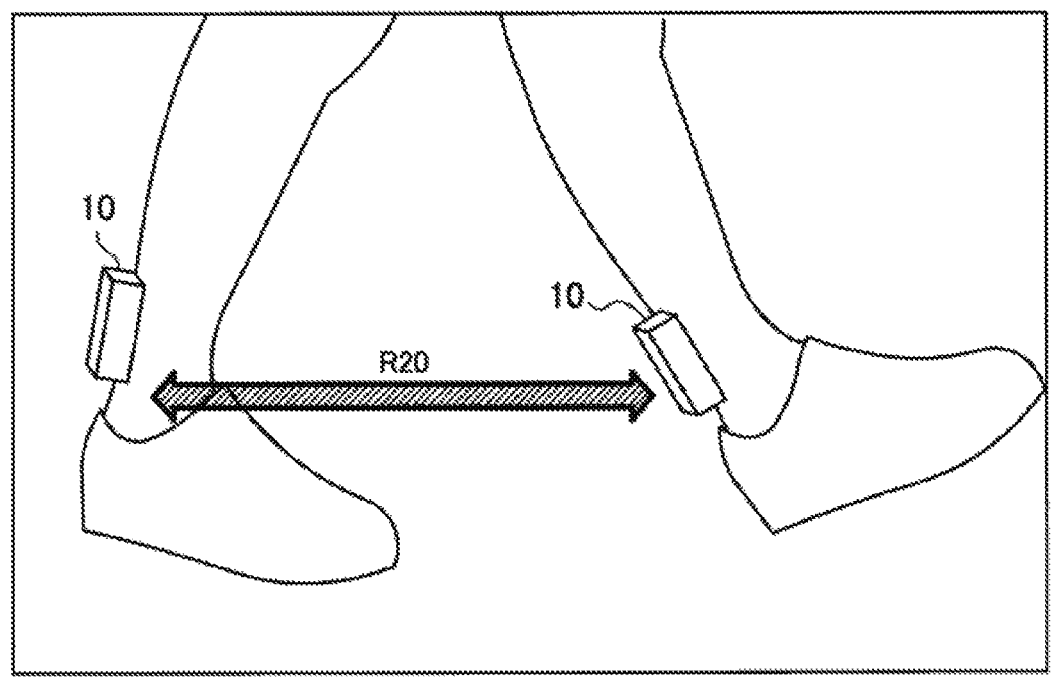

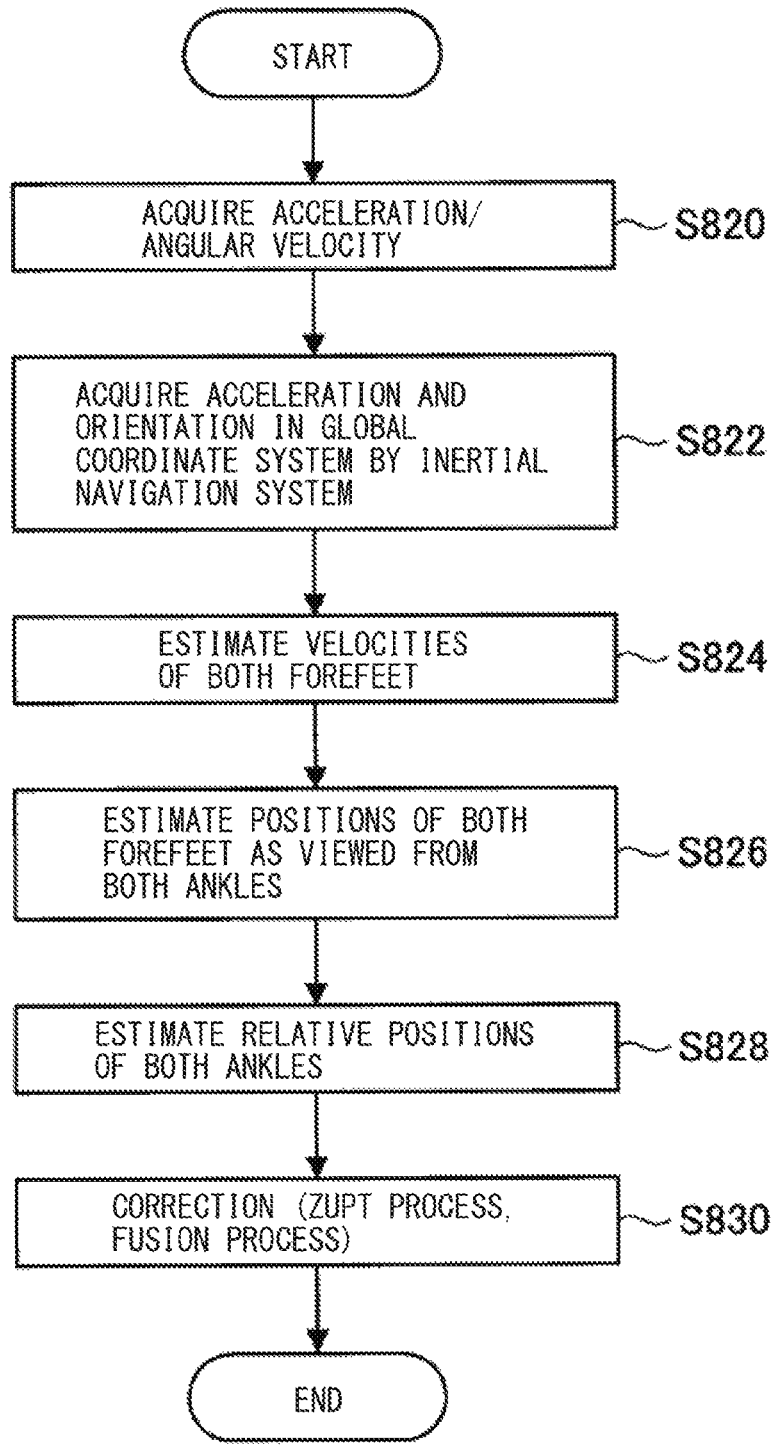
[FIG. 36]

[ FIG. 37 ]
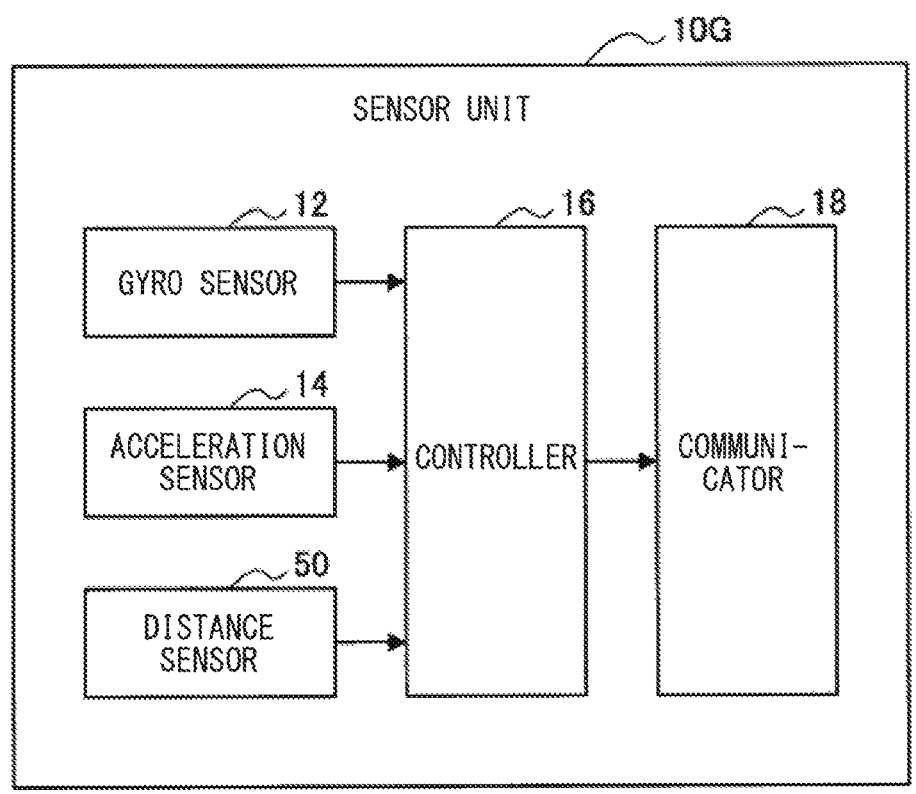

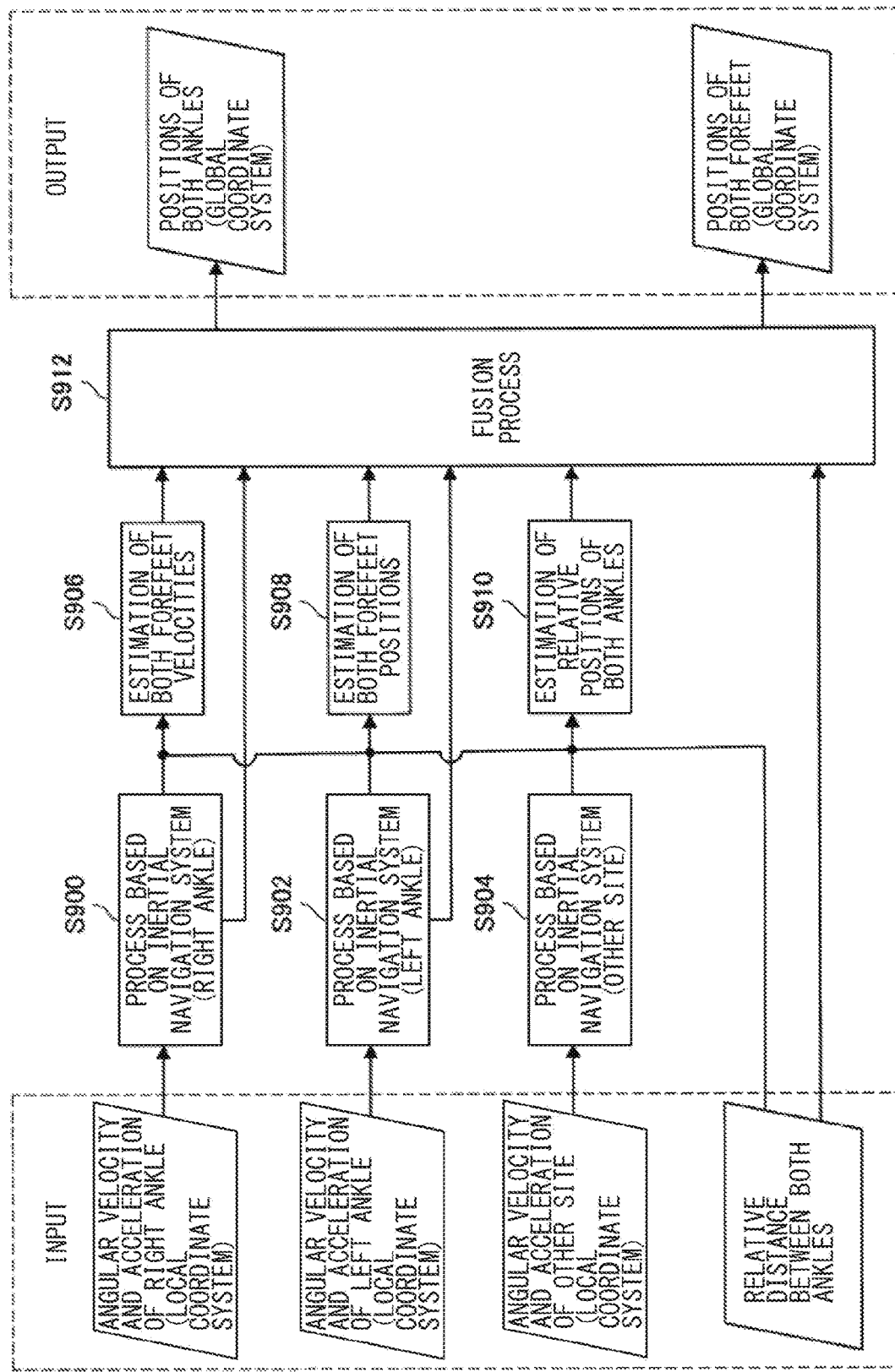
[FIG. 38]

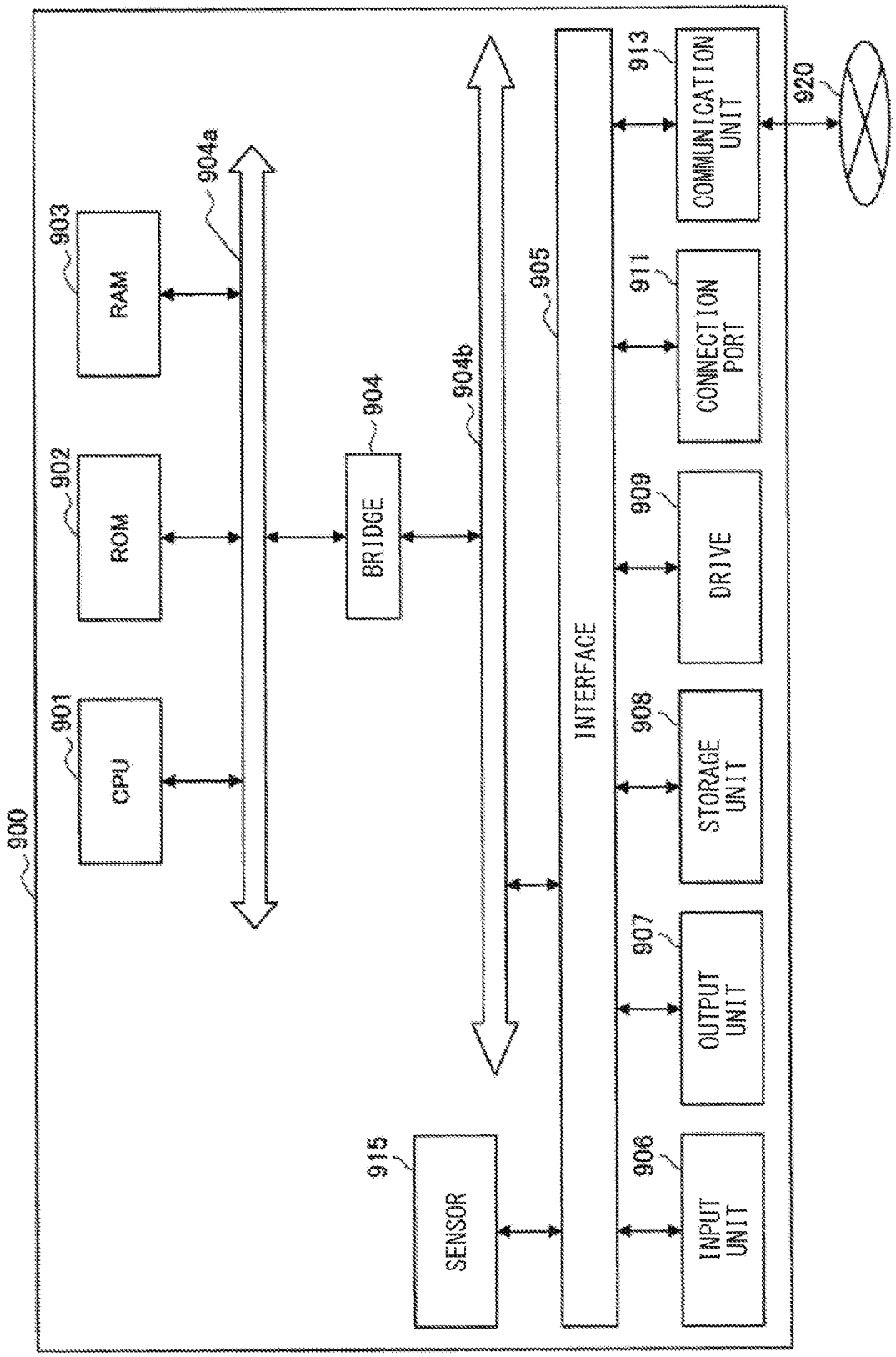
[FIG. 39]

PROGRAM, INFORMATION PROCESSOR, AND INFORMATION PROCESSING METHOD

CROSS REFERENCE TO PRIOR APPLICATION

This application is a National Stage Patent Application of PCT International Patent Application No. PCT/JP2019/016150 (filed on Apr. 15, 2019) under 35 U.S.C. § 371, which claims priority to Japanese Patent Application No. 2018-079335 (filed on Apr. 17, 2018), which are all hereby incorporated by reference in their entirety.

TECHNICAL FIELD

The present disclosure relates to a program, an information processor, and an information processing method.

BACKGROUND ART

In recent years, motion capture techniques for acquiring body motion information have been actively developed. The acquired body motion information is used, for example, for improvement in forms in sports, or in applications including VR (Virtual Reality) and AR (Augmented reality).

To acquire body motion information, for example, a position of a motion sensor attached to a body is calculated from sensor data (sensing data) acquired by the motion sensor by using an inertial navigation system (INS) (for example, PTL 1 below).

CITATION LIST

Patent Literature

PTL1: International Publication No. WO 2017/217050

SUMMARY OF THE INVENTION

Problems to be Solved by the Invention

In the inertial navigation system, however, the calculation of position is accomplished by integrating acceleration included in the sensor data a plurality of times, and therefore an error in the obtained position can become large with time. Accordingly, there has been a demand for a technique for obtaining, with higher accuracy, information regarding the position of a site to which the motion sensor is attached.

Means for Solving the Problems

According to the present disclosure, there is provided a program that causes a computer to implement a correction function of referencing a first output obtained by performing a first process on sensor data acquired by two or more motion sensors attached to two or more sites of a body and a second output obtained by performing a second process on the sensor data, and correcting position information for attachment sites to which the motion sensors are attached.

Furthermore, according to the present disclosure, there is provided an information processor including a corrector that references a first output obtained by performing a first process on sensor data acquired by two or more motion sensors attached to two or more sites of a body and a second output obtained by performing a second process on the sensor data, and corrects position information for attachment sites to which the motion sensors are attached.

Furthermore, according to the present disclosure, there is provided an information processing method including: referencing, by a processor, a first output obtained by performing a first process on sensor data acquired by two or more motion sensors attached to two or more sites of a body and a second output obtained by performing a second process on the sensor data; and correcting, by the processor, position information for attachment sites to which the motion sensors are attached.

Effect of the Invention

As described above, according to the present disclosure, it is possible to obtain, with higher accuracy, information regarding the positions of the sites to which the motion sensors are attached.

It should be noted that the above-described effect is not necessarily limiting, and any of the effects illustrated in the present specification or other effects that may be expected from the present specification may be achieved together with or instead of the above-described effect.

BRIEF DESCRIPTION OF DRAWINGS

FIG. 1 is an image diagram that describes an overview of a first embodiment of the present disclosure.

FIG. 2 is an explanatory diagram that describes an existing motion capture technique using a forward kinematics calculation.

FIG. 3 is an explanatory diagram that describes the forward kinematics calculation.

FIG. 4 is an explanatory diagram that describes an approach using an inverse kinematics calculation.

FIG. 5 is an explanatory diagram that describes the inverse kinematics calculation.

FIG. 6 is an explanatory diagram that describes a first step according to the embodiment.

FIG. 7 is an explanatory diagram that describes a second step according to the embodiment.

FIG. 8 is a schematic diagram illustrating an overview of a position estimation process based on an inertial navigation system.

FIG. 9 is a schematic diagram illustrating a time-varying image of a position error that can occur in the position estimation process based on the inertial navigation system.

FIG. 10 is a schematic diagram illustrating an overview of a position estimation process based on a dynamics model.

FIG. 11 is a schematic diagram illustrating a time-varying image of a position error that can occur in the position estimation process based on the dynamics model.

FIG. 12 is a schematic diagram illustrating an overview of a position estimation process according to the embodiment.

FIG. 13 is a schematic diagram illustrating a time-varying image of a position error that can occur in the position estimation process according to the embodiment.

FIG. 14 illustrates an example f a unit configuration of a system according to the embodiment.

FIG. 15 illustrates an example of a functional configuration of the system according to the embodiment.

FIG. 16 is an explanatory diagram illustrating an example of a combination of attachment sites and a dynamics model.

FIG. 17 illustrates an example of reliability identification by a reliability identifier 550.

FIG. 18 is a flowchart illustrating an operation example of the system according to the embodiment.

FIG. 19 illustrates a functional configuration example of a system according to a first modification example.

FIG. 20 illustrates a functional configuration example of a system according to a second modification example.

FIG. 21 illustrates a functional configuration example of a system according to a third modification example.

FIG. 22 is an explanatory diagram that describes an overview of a non-tracking-type dynamics model.

FIG. 23 is an explanatory diagram that describes an overview of a tracking-type dynamics model.

FIG. 24 illustrates a functional configuration example of a system according to a fourth modification example.

FIG. 25 illustrates a unit configuration example of a system according to a fifth modification example.

FIG. 26 is an explanatory diagram (Part 1) that describes a first ZUPT technique according to a second embodiment of the present disclosure.

FIG. 27 is an explanatory diagram (Part 2) that describes the first ZUPT technique according to the embodiment.

FIG. 28 is an explanatory diagram (Part 1) that describes a second ZUPT technique according to the embodiment.

FIG. 29 is an explanatory diagram (Part 2) that describes the second ZUPT technique according to the embodiment.

FIG. 30 illustrates an example of a functional configuration of a system according to the embodiment.

FIG. 31 is a flowchart illustrating an operation example of the system according to the embodiment.

FIG. 32 is an explanatory diagram that describes estimation of forefoot velocity according to the embodiment.

FIG. 33 is an explanatory diagram that describes estimation of forefoot position according to the embodiment.

FIG. 34 is an explanatory diagram that describes a ZUPT technique according to modification example 1 of the embodiment.

FIG. 35 is an explanatory diagram that describes estimation of a relative position according to modification example 1 of the embodiment.

FIG. 36 is a flowchart illustrating an operation example of a system according to modification example 1 of the embodiment.

FIG. 37 illustrates an example of a unit configuration of a sensor unit 10 according to modification example 2 of the embodiment.

FIG. 38 is an explanatory diagram that describes a ZUPT technique according to modification example 2 of the embodiment.

FIG. 39 is an explanatory diagram illustrating a hardware configuration example.

MODES FOR CARRYING OUT THE INVENTION

Preferred embodiments of the present disclosure will be described in detail below with reference to the accompanying drawings. It is to be noted that, in the present specification and drawings, components that have substantially the same functional configurations are denoted by the same reference signs, and redundant descriptions thereof are thus omitted.

In addition, in the present specification and drawings, a plurality of components having substantially the same functional configurations is sometimes distinguished from each other by attaching different alphabets after the same reference signs. However, in a case where it is unnecessary in particular to distinguish a plurality of components having substantially the same functional configurations from each other, only the same reference signs are assigned, It is to be noted that the description will be given in the following order.

<<1. Overview of First Embodiment>>
<<2. Principle of Present Technology>>
<<3. Configuration Example>>
<<4. Operation Example>>
<<5. Modification Examples>>
<<6. Overview of Second Embodiment>>
<<7. Hardware Configuration Example>>
<<8. Conclusion>>

Overview of First Embodiment

For example, skeleton information represented by a skeleton structure indicating the structure of a body is used to visualize information regarding motions of the body of a human, an animal, or the like. The skeleton structure includes information regarding sites, and bones which are line segments connecting the sites. The sites in the skeleton structure each correspond to, for example, an extremity site, a joint site, or the like. Further, the bones in the skeleton structure may correspond to, for example, human bones; however, the positions and the number of the bones may not necessarily be consistent with those in the actual human skeleton.

Site positions in the skeleton information are acquirable by, for example, attaching markers or motion sensors to respective corresponding sites of the body. For example, there exists a technique in which markers are attached to various sites of the body to acquire positions of the markers using an external camera or the like, and a technique in which motion sensors are attached to sites of the body to acquire position information of the motion sensors on the basis of sensor data acquired by the motion sensors.

Compared with the technique using markers attached to the body, the technique using motion sensors attached to the body is advantageous in that there is no need for any external camera, light source, or marker, resulting in portability and easiness of setting up. Further, the technique using motion sensors attached to the body is free from limitations by an image-capturing range of the camera, thus having an advantage in its availability even in a wide outdoor space, a space having a complicated shape that tends to generate a blind spot, a narrow and small space, etc.

However, in order to estimate a whole-body skeleton with the technique using motion sensors attached to the body, it is necessary to attach a motion sensor to every joint, which sometimes places a heavy load on the user. Further, although dedicated suits have also been developed to suitably attach a large number of motion sensors to various sites on the user, the dedicated suits are sometimes costly to manufacture.

Accordingly, focusing on the above-described circumstances, the present inventors have created a first embodiment of the present disclosure. A system according to the first embodiment of the present disclosure makes it possible to acquire position information for a larger number of sites than the number of attached motion sensors while achieving a reduction in the number of the motion sensors to be attached. It is to be noted that in the present specification, a motion sensor is a device that senses motion of the body and may include an inertial sensor (an acceleration sensor, an angular velocity sensor), a geomagnetic sensor, a barometric sensor, an image sensor, and the like. In the following, an example in which at least an inertial sensor is attached as a motion sensor to the body will be mainly described.

An overview of the present embodiment will be described with reference to FIG. 1. FIG. 1 is an image diagram that describes the overview of the present embodiment. In the example illustrated in FIG. 1, six sensor units 10A to 10F are attached to six sites of the body of a user U1. The sensor units 10A to 10F include, for example, an inertial sensor (IMU: Inertial Measurement Unit) such as an acceleration sensor that acquires acceleration (Acceleration) or a gyro sensor (an angular velocity sensor) that acquires angular velocity (Angular Velocity).

The sensor units 10A to 10F are preferably attached to a joint site e.g., waist or head) serving as a reference in the body or to the near extremities of the body (wrist, ankle, head, etc.). In the example illustrated in FIG. 1, the sensor unit 10A is attached to the waist; the sensor units 10B and 10E are attached to the wrists; the sensor units 10C and 10D are attached to the ankles; and the sensor unit 10F is attached to the head, of the user U1. It is to be noted that in the following description, the sensor units 10A to 10F may be collectively and simply referred to as sensor units 10 in a case where it is not necessary to distinguish them from each other. Further, in the following, sites of the body to which the sensor units 10 are attached may also be referred to as attachment sites. In addition, the number of the sensor units 10 and attachment positions (positions of the attachment sites) are not limited to those in the example illustrated in FIG. 1.

The system according to the present embodiment acquires information regarding position (Position) and orientation (Orientation) of each of the attachment sites on the basis of sensor data acquired by the sensor units 10. As information (hereinafter also referred to as attachment site information) for the attachment sites P101 to P106 to which the sensor units 10A to 10F are attached, FIG. 1 illustrates attachment site information PD100 that includes position information and orientation information.

Further, on the basis of the position information and the orientation information for the attachment sites P101 to P106 to which the sensor units 10A to 10F are attached, the system according to the present embodiment estimates skeleton information including position information and orientation information for various sites of the skeleton structure. Here, in the present embodiment, the position information and the orientation information are estimated for, among sites of the skeleton structure, not only the attachment sites to which the sensor units 10 are attached but also a site to which none of the sensor units 10 is attached (hereinafter also referred to as a non-attachment site).

In the example of FIG. 1, skeleton information SD100 is illustrated that includes position information and orientation information for various sites in the skeleton structure. The skeleton information SD100 includes information for a non-attachment site SP107 as well as information for an attachment site SP101 corresponding to the attachment site P101 and an attachment site SP102 corresponding to the attachment site P102.

In addition to the information for the sites, the skeleton information may also include information (position information, orientation information, etc.) for bones. For example, in the example illustrated in FIG. 1, the skeleton information SD100 may include information for a bone SB101. For example, on the basis of position information and orientation information for sites in the skeleton structure, it is possible to identify information for a bone between the sites.

As described above, according to the present embodiment, information for a non-attachment site to which none of the motion sensors is attached is estimated on the basis of information for the attachment sites to which the motion sensors are attached. This makes it possible to reduce the number of the motion sensors to be attached while maintaining the number of sites for which information is to be acquired. In the following, a description is given of the technical principle according to the present embodiment for achieving the above-described effects.

2. Principle of Present Technology

<2-1. Approach of Present Embodiment>

As an existing motion capture technique, there is a technique of acquiring skeleton information by forward kinematics (FK: Forward Kinematics) calculation. The forward kinematics calculation is a method of calculating the position of an extremity site on that basis of orientations of joint sites.

FIG. 2 is an explanatory diagram that describes the existing motion capture technique using the forward kinematics calculation. FIG. 2 illustrates skeleton information SD90 represented by a skeleton structure.

In the skeleton information SD90 illustrated in FIG. 2, attachment sites to which sensor units including inertial sensors are attached are marked with circles. Thus, sites SP91 to SP96 are the attachment sites. Here, in a case where the sensor units include angular velocity sensors, it is possible to identify orientation information (angle information) for the attachment sites by using an attitude measurement technique such as an AHRS(Attitude and Heading Reference System).

For example, in a case where a body coordinate system is set with the site SP91 corresponding to the waist of the body as a reference (a point of origin), it is possible to identify position information for the sites SP92 to SP96 in the body coordinate system by performing the forward kinematics calculation on the basis of orientation information for the sites SP91 to SP95. Note that in the following description, the site used as a reference in the body coordinate system will sometimes be referred to as a root site.

Here, the forward kinematics calculation will be described with reference to FIG. 3. FIG. 3 is an explanatory diagram that describes the forward kinematics calculation. For the sake of simplicity, FIG. 3 illustrates an example in which an arm is regarded as a simple linkage with two degrees of freedom.

In the example illustrated in FIG. 3, a site SP81 is the root site, and there is illustrated an xy coordinate system (a plane coordinate system) with the site SP81 as the reference (the point of origin). In the forward kinematics calculation, as described above, the orientation information for each site is known. In the example illustrated in FIG. 3, an angle $\theta_1$ formed between a bone SB81 and the x-axis based on the orientation of the site SP81, and an angle $\theta_2$ formed between the bone SB81 and a bone SB82 based on the orientation of a site SP82 are known. Further, in the forward kinematics calculation, the distances between sites, that is, the lengths of bones are also known, in the example illustrated in FIG. 3, the length $l_1$ of the bone SB81 and the length $l_2$ of the bone SB82 are known.

According to the forward kinematics calculation, it is possible to calculate a position $(x_1, y_1)$ of a site SP83 using the known information as described above. Specifically, the position $(x_1, y_1)$ of the site SP83 is expressed by the following equations (1) and (2).

[Math. 1]

$$x_1 = l_1 \cos\theta_1 + l_2 \cos(\theta_1 + \theta_2) \qquad (1)$$

$$y_1 = l_1 \sin\theta_1 + l_2 \sin(\theta_1 + \theta_2) \qquad (2)$$

While FIG. 3 illustrates an example of a planar and simple mechanism, it is also possible to perform the forward kinematics calculation in a similar manner even in a case of a three-dimensional and more complex mechanism. That is, it is possible to identify the position information for an extremity site by using the orientation information for a joint site between the root site serving as a reference and the extremity site, and information regarding the distance between the sites. In addition, not only the position information for the extremity sites but also the position information for a joint site located between the root site and an extremity site in the skeleton structure (for example, the position information for the site SP82 in the example illustrated in FIG. 3) is identified by the forward kinematics calculation.

One example of existing motion capture techniques using the forward kinematics calculation has been described above. However, as has been described with reference to FIGS. 2 and 3, identifying position information for each site by using the forward kinematics calculation necessitates orientation information for each joint site. Thus, the use of the forward kinematics calculation is a factor responsible for an increase in the number of motion sensors to be attached to the body.

Accordingly, in the present embodiment, skeleton information is acquired by using inverse kinematics (IK: Inverse Kinematics) calculation instead of the forward kinematics calculation described above. The inverse kinematics calculation is a method of calculating the orientation of each joint site on the basis of the position of an extremity site.

FIG. 4 is an explanatory diagram that describes an approach using the inverse kinematics calculation. FIG. 4 illustrates skeleton information SD90 represented by a skeleton structure similar to FIG. 2.

In the skeleton information SD90 illustrated in FIG. 4, attachment sites to which sensor units including inertial sensors are attached are marked with circles. Thus, sites SP91 to SP96 are the attachment sites. Meanwhile, in the skeleton information SD90 illustrated in FIG. 4, the sites to which any sensor units including inertial sensors are unattached are marked with crosses. Specifically, the sites SP92 to SP95, which are between the site 91 and the site 96, are the non-attachment sites.

Assume here that a body coordinate system has been set with the site SP91 corresponding to the waist of the body as the reference (the point of origin) and the position information for the site SP96 in the body coordinate system has been acquired. In such a case, it is possible to identify orientation information and position information for the sites SP92 to SP95 by performing the inverse kinematics calculation on the basis of the position information for the site SP96, which is an extremity site.

Here, the inverse kinematics calculation will be described with reference to FIG. 5. FIG. 5 is an explanatory diagram that describes the inverse kinematics calculation. For the sake of simplicity, FIG. 5 illustrates an example in which an arm is regarded as a simple linkage with two degrees of freedom.

In the example illustrated in FIG. 5, the site SP81 is the root site, and there is illustrated an xy coordinate system (a plane coordinate system) with the site SP81 as the reference (the point of origin). Here, as illustrated in the upper left in FIG. 5, assume that the length $l_1$ of the bone SB81 whose one end point is the site SP81 and the length $l_2$ of the bone SP82 whose one end point is the site SP83 are known.

In the inverse kinematics calculation, an angle formed between the bone SB81 and the x-axis and an angle formed between the bone SB81 and the bone SB82 are calculated using the known information as described above. In the inverse kinematics calculation, however, there can exist a plurality of solutions. In the example of FIG. 5, obtained are a solution that, as illustrated in the upper right in FIG. 5, an angle $\theta_{11}$ is formed between the bone SB81 and the x-axis and an angle $\theta_{21}$ is formed between the bone SB81 and the bone SB82; and a solution that, as illustrated in the lower right in FIG. 5, an angle $\theta_{12}$ is formed between the bone SB81 and the x-axis and an angle $\theta_{22}$ is formed between the bone SB81 and the bone SB82. It is to be noted that FIG. 5 illustrates an example of a planar and simple mechanism; therefore, there can exist a larger number of solutions in a case of a three-dimensional mechanism or in a case where there are a larger number of joint sites, for example.

The approach using the inverse kinematics calculation has been described above. Next, an overview of processing according to the present embodiment will be described. In the present embodiment, as described above, skeleton information (positions and orientations of joint sites) is acquired using the inverse kinematics calculation. Thus, the processing is performed in two general steps as illustrated in FIG. 6 and FIG. 7 described below.

FIG. 6 is an explanatory diagram that describes a first step according to the present embodiment. As has been described with reference to FIG. 1, in the present embodiment, information regarding acceleration and angular velocity is acquirable from two or more inertial sensors attached to two or more sites of the body. Further, it is possible to obtain information regarding acceleration (three-dimensional) and orientation (four-dimensional) in a global coordinate system from the information regarding acceleration and angular velocity acquired from the inertial sensors. It is to be noted that the global coordinate system is, for example, a coordinate system for common use by a plurality of sensors, devices, etc., and may be a coordinate system corresponding to a real space. The attachment site information PD10 illustrated in FIG. 6 includes information regarding acceleration and orientation for the attachment sites P11 to P16 acquired by the inertial sensors, and therefore includes information of 6×7=42 dimensions in total.

In the first step, position estimation for the attachment sites is performed (S100) on the basis of the attachment site information PD10, and thereby attachment site information PD12 is obtained that includes position information indicating positions (three-dimensional) of the attachment sites P11 to P16. It is to be noted that in a case where the attachment site information PD12 is represented in a body coordinate system with the attachment site P11 as a root site, the position information for the attachment site P11 is not necessary and therefore the attachment site information PD12 includes position information of 5×3=15 dimensions in total. Further, the attachment site information PD12 may include the orientation information for each of the sites in the global coordinate system included in the attachment site information PD10. In such a case, the attachment site information PD12 includes orientation information of 6×4=24 dimensions in total.

FIG. 7 is an explanatory diagram that describes a second step according to the present embodiment. Because the attachment site information PD12 illustrated in FIG. 7 is similar to the attachment site information PD12 illustrated in FIG. 6, the description thereof is omitted here.

In the second step, position estimation (interpolation) for a non-attachment site is performed (S200) on the basis of the attachment site information PD12, and thereby skeleton information SD10 is obtained that includes position information for the non-attachment site to which no inertial sensor is attached, in addition to the position information for the attachment sites. In the example illustrated in FIG. 7, for example, sites SP11 and SP12 are the attachment sites and a site SP20 is the non-attachment site.

Here, the position estimation for the non-attachment site, i.e., the second step, may be performed by the inverse kinematics calculation as described above. In order to perform the position estimation for the non-attachment site with high accuracy, it is desirable that the attachment site information PD12 serving as an input thereto be obtained with high accuracy in the first step. The first step, i.e., the position estimation for the attachment sites, may be performed by an inertial navigation system, for example. However, in a case where the position estimation for the attachment sites is performed by the inertial navigation system, an error in the estimated position can become larger with time. To cope with this, in the present embodiment, the position information for the attachment sites estimated by the inertial navigation system is corrected to thereby acquire position information for the attachment sites with higher accuracy. The correction of position information for the attachment sites according to the present embodiment is described below.

<2-2. Correction of Position Information for Attachment Site>

First, a description will be given of a position estimation process based on the inertial navigation system. The inertial navigation system is a technique for calculating a sensor position by performing integration (Integration) of angular velocity and acceleration a plurality of times, and is employed in, for example, vessels, aircraft, or the like. FIG. 8 is a schematic diagram illustrating an overview of the position estimation process based on the inertial navigation system.

In the inertial navigation system, first, an orientation of a sensor unit in a global coordinate system is calculated by integrating an angular velocity (an example of sensor data) in a local coordinate system acquired by a gyro sensor included in the sensor unit (S111). Next, in the inertial navigation system, on the basis of the orientation of the sensor unit in the global coordinate system, an acceleration (an example of sensor data) of the sensor unit in the local coordinate system (a coordinate system set for each sensor unit) acquired by an acceleration sensor included in the sensor unit is subjected to a coordinate system conversion into an acceleration of the sensor unit in the global coordinate system (S112). Then, the acceleration of the sensor unit in the global coordinate system resulting from the coordinate system conversion is integrated (S113) to thereby calculate a velocity of the sensor unit in the global coordinate system. Next, the velocity of the sensor unit in the global coordinate system is integrated (S114) to thereby calculate a moving distance of the sensor unit. Here, by combining the moving distances in the global coordinate system for each subdivision point, it is possible to obtain relative position information with respect to an initial position as a starting point. If the initial position is known, it is possible to calculate absolute position information (i.e., three-dimensional coordinates in the global coordinate system) of the sensor unit from the above information in the above-described manner, orientation information and position information of the sensor unit are outputted by the position estimation process based on the inertial navigation system.

The position estimation process based on the inertial navigation system illustrated in FIG. 8 is performable at a relatively low process load and a high speed.

Here, in the inertial navigation system, only one integration is applied to the angular velocity in step S111 in order to obtain the orientation information, and further, it is possible to acquire the orientation information with higher accuracy by combining a well-known technique such as AHRS. On the other hand, to obtain the position information, two integrations are applied to the acceleration in step S113 and step S114. Therefore, if the acceleration acquired by the acceleration sensor includes an error, the error can be accumulated in the outputted position information.

FIG. 9 is a schematic diagram illustrating a time-varying image of a position error that can occur in the position estimation process based on the inertial navigation system. As illustrated in FIG. 9, for a short period of time after the start of estimation of the position information by the inertial navigation system, the position error is small and it is thus possible to estimate the position information with high accuracy. However, the error included in the position information estimated by the inertial navigation system can increase with time as illustrated in FIG. 9, and therefore if the estimation is performed continuously for a long time, a significantly large error can be included in the position information.

To address this, in the present embodiment, position estimation for the attachment sites is performed by regression on the basis of a dynamics model (Dynamics Model), FIG. 10 is a schematic diagram illustrating an overview of a position estimation process based on the dynamics model.

The process in steps S121 and S122 illustrated in FIG. 10 is similar to the process in steps S111 and S112 described with reference to FIG. 8, and therefore the description thereof is omitted here. As illustrated in FIG. 10, in the position estimation process based on the dynamics model, position information of the sensor units is estimated by regression (S123) without performing integration of acceleration. In the regression estimation process in step S123, position information is estimated by regression where the orientations and accelerations of the sensor units in the global coordinate system are fitted to a dynamics model prepared in advance. Here, it is possible to generate the dynamics model by, for example, learning kinematic constraint information (for example, information including a plurality of samples of positions and orientations of various sites in postures or a series of motions acquired previously) in advance. It is to be noted that various regression analysis methods are usable for the regression estimation process in step S123 and, for example, methods such as DNN (Deep Neural Network) and Random Forest may be used alone or in combination.

Here, because the process illustrated in FIG. 10 involves no integration of acceleration, a position error is likely to become larger with time as with the case with the inertial navigation system described with reference to FIGS. 8 and 9. FIG. 11 is a schematic diagram illustrating a time-varying image of a position error that can occur in the position estimation process based on the dynamics model. Although a position error also occurs in the position estimation process based on the dynamics model as illustrated in FIG. 10, it does not become larger with time. Accordingly, a large error is less likely to result even if the process is performed continuously for a long time.

Therefore, it is considered that the position estimation process based on the dynamics model illustrated in FIG. 10 makes it possible to estimate position information with higher accuracy. However, because the position estimation process based on the dynamics model performs statistical estimation by regression, variations in output (estimation result) are likely to be discontinuous even in a case where variations in input are continuous. As a result, for example, the finally obtained skeleton information as visualized can tend to give rise to a sense of strangeness. Further, when compared with the position estimation process based on the inertial navigation system illustrated in FIG. 8, the position estimation process based on the dynamics model illustrated in FIG. 10 is higher in process load, which makes it difficult to achieve higher execution speed than the position estimation process based on the inertial navigation system.

As described above, the position estimation process based on the inertial navigation system and the position estimation process based on the dynamics model have their respective features. Therefore, in the present embodiment, position information is estimated with higher accuracy by combining the position estimation process based on the inertial navigation system and the position estimation process based on the dynamics model, and correcting the estimated position information. In the following, the position estimation process based on the inertial navigation system may be referred to as a first process, and the position estimation process based on the dynamics model may be referred to as a second process.

FIG. 12 is a schematic diagram illustrating an overview of a position estimation process according to the present embodiment. It is to be noted that FIG. 12 illustrates an overview, and thus the position estimation process according to the present embodiment may further include a process unillustrated in FIG. 12.

As illustrated in FIG. 12, the position estimation process according to the present embodiment includes a correction process (S130) in addition to the first process (S111 to S114) based on the inertial navigation system and the second process (S121 to S123) based on the dynamics model. In the correction process of step S130, correction is performed by referencing an output of the first process (hereinafter, also referred to as a first output) and an output of the second process (hereinafter, also referred to as a second output). It is to be noted that the first output includes orientation information and position information for the attachment sites, and the second output includes position information therefor. Then, in step S130, the position information included in the first output is corrected on the basis of the orientation information included in the first output and the position information included in the second output. Note that in step S130, the orientation information included in the first output may be used for correcting the position information and be outputted as it is. Further, the correction process in step S130 is implementable by a Kalman filter, for example.

Moreover, as described above, the first process is executable faster than the second process. Therefore, the correction process (S130) may be executed at the time when the second output is obtained and, if the second output is not obtained but only the first output is obtained, the first output may be outputted as it is as an output of the position estimation process according to the present embodiment.

FIG. 13 is a schematic diagram illustrating a time-varying image of a position error that can occur in the position estimation process according to the present embodiment. Assume that in the example illustrated in FIG. 13, the second output is obtained and correction based on the second output is performed at a time $t_{11}$. As illustrated in FIG. 13, in the position estimation process according to the present embodiment, the position error becomes larger with time during a period from the start of the process to the time $t_{11}$, however, as a result of the correction based on the second output performed at the time $t_{11}$, the position error is suppressed.

Thus, according to the position estimation process of the present embodiment, position error is suppressed every time correction is performed. Therefore, error is less likely to become larger with time, and even if the process is performed continuously for a long period of time, a large error is less likely to result. Further, in the position estimation process according to the present embodiment, the first output is outputted as it is in the case where the second output is not obtainable. This makes it possible to estimate position information more frequently as compared with a case of performing position estimation with only the second process based on the dynamics model.

3. Configuration Example

The principle of the technology according to the present embodiment has been described above. Next, a configuration example of the present embodiment will be described. In the following, a unit configuration example and a functional configuration example of the present embodiment will be described in order.

<3-1. Unit Configuration Example>

FIG. 14 illustrates an example of a unit configuration of a system according to the present embodiment. As illustrated in FIG. 14, the system according to the present embodiment includes the sensor units 10A to 10F, a hub unit 20, an information processor 30, and an output unit 40.

The sensor units 10 are units that each include at least a motion sensor and are to be attached to sites of a body. The sites to which the sensor units 10A to 10F are attached have been described with reference to FIG. 1, and individual descriptions will thus be omitted. For example, as illustrated in FIG. 14, the sensor units 10 each include a gyro sensor 12, an acceleration sensor 14, a controller 16, and a communicator 18. Note that the motion sensors included in the sensor units 10 are not limited to inertial sensors (the gyro sensors 12 and the acceleration sensors 14). For example, the sensor units 10 may include motion sensors such as geomagnetic sensors, barometric sensors, image sensors or the like in place of the inertial sensors or in addition to the inertial sensors. Further, while FIG. 14 illustrates the configuration of only the sensor unit 10A, the sensor units 10A to 10F may have identical configurations.

The gyro sensor 12 is an inertial sensor that acquires angular velocity as sensor data. The angular velocity acquired by the gyro sensor 12 may be an angular velocity of the sensor unit 10 in a local coordinate system.

Further, the acceleration sensor 14 is an inertial sensor that acquires acceleration as sensor data. The acceleration acquired by the acceleration sensor 14 may be an acceleration of the sensor unit 10 in a local coordinate system that is set for each sensor unit 10.

The controller 16 controls operations of the sensor unit 10. For example, the controller 16 may control communications performed by the communicator 18 and may cause the sensor data (angular velocity, and acceleration) acquired by the gyro sensor 12 and the acceleration sensor 14 to be transmitted to the hub unit 20. Alternatively, the controller 16 may perform processing on the sensor data acquired by the gyro sensor 12 and the acceleration sensor 14, and may cause the processing results obtained through the processing to be transmitted to the hub unit 20.

The communicator 18 is a communication module for transmitting and receiving data to and from other units in a wired manner or wirelessly. The communicator 18 communicates wirelessly with external equipment directly or via a network access point in a scheme such as a wired LAN (Local Area Network), wireless LAN, Wi-Fi (registered trademark) (Wireless Fidelity), infrared communication, Bluetooth (registered trademark), short-range/contactless communication or the like, for example.

The hub unit 20 is an information processor that receives information from a plurality of sensor units 10 and aggregates the information. It is to be noted that the sensor units 10 and the hub unit 20 may be connected to each other in a wired manner or wirelessly. The hub unit 20 includes, for example, communicator 22 and a controller 24 as illustrated in FIG. 14.

The communicator 22 is a communication module for transmitting and receiving data to and from other units in a wired manner or wirelessly. The communicator 22 communicates wirelessly with external equipment directly or via a network access point in a scheme such as a wired LAN, wireless LAN, Wi-Fi, infrared communication. Bluetooth, short-range/contactless communication or the like, for example.

The controller 24 controls operations of the hub unit 20. For example, the controller 24 may control communications performed by the communicator and may cause information received from the sensor units 10 to be transmitted as it is to the information processor 30. Alternatively, the controller 24 may perform processing on the information received from the sensor units 10, and may cause the processing results obtained through the processing to be transmitted to the information processor 30.

The information processor 30 is an information processor that receives information from the hub unit 20 and processes the information. It is to be noted that the hub unit 20 and the information processor 30 may be connected to each other in a wired manner or wirelessly. The information processor 30 includes, for example, a communicator 32 and a controller 34 as illustrated in FIG. 14.

The communicator 32 is a communication module for transmitting and receiving data to and from other units in a wired manner or wirelessly. The communicator 32 communicates wirelessly with external equipment directly or via a network access point in a scheme such as a wired LAN, wireless LAN, Wi-Fi, infrared communication, Bluetooth, short-range/contactless communication or the like, for example.

The controller 34 controls operations of the information processor 30. For example, the controller 34 performs processing on information received by the communicator 32. Further, the controller 34 is able to control display of the output unit 40 by controlling and causing the communicator 32 to transmit the foregoing processing results to the output unit 40 connected to the information processor 30. For example, the controller 34 may cause the output unit 40 to display visualized skeleton information, a 3-D model reflecting the skeleton information or the like on the basis of the skeleton information obtained as a result of the processing.

The output unit 40 is a unit that has at least a display function, and performs displaying in accordance with the control by the controller 34 of the information processor 30. The output unit 40 may be, for example, an installation-type display or an HMD (Head Mounted Display) to be worn by a user. Further, the output unit 40 and the information processor 30 may be an integral unit.

<3-2. Functional Configuration Example>

The unit configuration example of the system according to the present embodiment has been described above. Next, a functional configuration example of the system according to the present embodiment will be described. FIG. 15 illustrates an example of the functional configuration of the system according to the present embodiment. Note that FIG. 15 illustrates only the functional configuration that mainly represents the characteristics of the present embodiment, and the system according to the present embodiment may thus include a functional configuration unillustrated in FIG. 15.

Referring to FIG. 15, the system according to the present embodiment has functions as a global motion acceleration orientation calculator 510, an integral calculator 520, a selector 530, an attachment position regression estimator 540, a reliability identifier 550, a ground contact detector 560, a corrector 570, and an interpolator 580.

It is to be noted that each functional configuration in FIG. 15 described below may be achieved by any of the units illustrated in FIG. 14. For example, the controller 6 of the sensor unit 10 or the controller 24 of the hub unit 20 may have a function as the global motion acceleration orientation calculator 510, and the controller 34 of the information processor 3C) may have other functions as the integral calculator 520 to the interpolator 580. However, which unit has which function is not limited to such an example.

The global motion acceleration orientation calculator 510 has a function of performing processing on the basis of the sensor data (angular velocities and accelerations) acquired by the sensor units 10A to 10F illustrated in FIG. 14. Note that the global motion acceleration orientation calculator 510 may process pieces of the sensor data acquired respectively by the sensor units 10A to 10F independently of each other.

For example, the global motion acceleration orientation calculator 510 performs a process of integrating the angular velocities of the sensor units 10 in the local coordinate system included in the sensor data and thereby calculating orientations of the sensor units 10 in the global coordinate system (corresponding to steps S111 and S121 in FIG. 12). The global motion acceleration orientation calculator 510 may calculate the orientations of the sensor units 10 by AHRS. Note that in a case where the sensor units 10 include geomagnetic sensors, the global motion acceleration orientation calculator 510 may use sensor data acquired by the geomagnetic sensors in calculating the orientations of the sensor units 10 by Further, the global motion acceleration orientation calculator 510 performs a process of converting the calculated orientations of the sensor units 10 in the global coordinate system into orientation of the attachment sites to which those sensor units 10 are attached in the global coordinate system. The global motion acceleration orientation calculator 510 may convert the orientations of the sensor units 10 into the orientations of the attachment sites by using preliminary calibration results.

Further, on the basis of the orientations of the attachment sites in the global coordinate system, the global motion acceleration orientation calculator 510 performs a process of converting the accelerations in the local coordinate system included in the sensor data into accelerations in the global coordinate system (corresponding to steps S112 and S122 in FIG. 12).

Further, the global motion acceleration orientation calculator 510 performs a process of removing gravity components from the accelerations in the global coordinate system obtained as described above. For example, the global motion acceleration orientation calculator 510 may remove the gravity components from the accelerations in the global coordinate system on the basis of the orientations of the attachment sites in the global coordinate system.

The global motion acceleration orientation calculator 510 outputs the orientation information for the attachment sites in the global coordinate system obtained by the above-described process and the accelerations in the global coordinate system, from which the gravity components have been removed, to the integral calculator 520, the selector 530, and the attachment position regression estimator 540.

The integral calculator 520 calculates position information for the attachment sites in the global coordinate system by performing a process (corresponding to steps S113 and S114 in FIG. 12) of integrating twice the accelerations in the global coordinate system, from which the gravity components have been removed, inputted from the global motion acceleration orientation calculator 510. The integral calculator 520 outputs to the corrector 570 the calculated position information for the attachment sites in the global coordinate system and the orientation information for the attachment sites in the global coordinate system inputted from the global motion acceleration orientation calculator 510.

Note that the foregoing first process based on the inertial navigation system may be performed by the global motion acceleration orientation calculator 510 and the integral calculator 520 described above. Further, the position information and the orientation information outputted from the integral calculator 520 correspond to the first output.

The selector 530 selects a dynamics model for the attachment position regression estimator 540 to estimate the positions of the attachment sites by regression. For example, a plurality of dynamics models may be prepared depending on patterns of the sites to which the sensor units 10 are attached and may be stored in a memory section (not illustrated). From among such a plurality of dynamics models, the selector 530 selects a dynamics model to be used by the attachment position regression estimator 540.

The dynamics models may be prepared in advance for each combination of the attachment sites, for example. The selector 530 may select an appropriate dynamics model by identifying the combination of the attachment sites on the basis of information inputted from the global motion acceleration orientation calculator 510. Such a configuration allows the selector 530 to dynamically select an appropriate dynamics model even in a case where, for example, one or more of the sensor units 10 are detached and re-attached by the user at some point during operation of the system or power supply from batteries (not illustrated) is lost in one or more of the sensor units 10. Note that FIG. 15 illustrates an example in which the combination of the attachment sites is identified on the basis of the information inputted from the global motion acceleration orientation calculator 510; however, the selector 530 may identify the combination of the attachment sites by using the sensor data itself as an input or by using other information.

FIG. 16 is an explanatory diagram illustrating examples of combinations of the attachment sites and the dynamics models. In each of skeleton information SD101 to SD105 illustrated in FIG. 16, the attachment sites to which the sensor units 10 are attached are marked with circles. Also, different root sites may be set for different dynamics models.

For example, in the skeleton information SD101 corresponding to a whole-body model, the attachment site SP101 corresponding to the waist is the root site, and the sensor units 10 are attached to six attachment sites SP101 to SP106. In the skeleton information SD102 corresponding to an upper limb model, the attachment site SP106 corresponding to the head is the root site, and the sensor units 10 are attached to three attachment sites SP102, P105, and SP106. Further, in the skeleton information D103 corresponding to a head-to-arm model, the attachment site SP106 corresponding to the head is the root site, and the sensor units 10 are attached to two attachment sites SP102 and SP106. Further, in the skeleton information D104 corresponding to a waist-to-arm model, the attachment site SP101 corresponding to the waist is the root site, and the sensor units 10 are attached to two attachment sites SP101 and SP105. Further, in the skeleton information D105 corresponding to a lower limb model, the attachment site SP101 corresponding to the waist is the root site, and the sensor units 10 are attached to three attachment sites SP101, SP103, and SP104.

Note that not only the attachment position regression estimator 540 to be described later but also the corrector 570 and the interpolator 580 to be described later perform processes in accordance with the combination of the attachment sites, and therefore combinations of non-attachment sites to be estimated can differ depending on the combination of the attachment sites (i.e., depending on the dynamics model). Sites for which the system according to the present embodiment is able to estimate position information and orientation information may be the attachment sites, and non-attachment sites that are located between a plurality of attachment sites in a predetermined skeleton structure. In the skeleton information SD101 to SD105 in FIG. 16, indicated by hatching are the sites (including attachment sites and non-attachment sites) for which it is possible to estimate position information and orientation information in the present embodiment, in accordance with the combinations of the attachment sites.

It should be noted that FIG. 16 illustrates an example, and combinations of the attachment sites in the dynamics models usable in the present embodiment are not limited to the example illustrated in FIG. 16.

Using the dynamics model selected by the selector 530, the attachment position regression estimator 540 performs a regression estimation process (corresponding to step S123 in FIG. 12) of estimating position information for the attachment sites by regression based on the orientation information for the attachment sites in the global coordinate system and the accelerations in the global coordinate system from which the gravity components have been removed. Note that the attachment position regression estimator 540 according to the present embodiment estimates the position information for the attachment sites in a body coordinate system with reference to the root site set for each dynamics model. The attachment position regression estimator 540 outputs the estimated position information for the attachment sites in the body coordinate system to the reliability identifier 550 and the corrector 570.

Note that the foregoing second process based on the dynamics model may be performed by the global motion acceleration orientation calculator 510 and the attachment position regression estimator 540 described above. Further, the position information outputted from the attachment position regression estimator 540 corresponds to the second output.

The reliability identifier 550 has a reliability identification function of identifying reliability of the position information for the attachment sites estimated by the attachment position regression estimator 540, which will also be referred to as position information included in the second output. The reliability identified by the reliability identifier 550 may be used in corrections by the corrector 570 to be described later. For example, in a case where the reliability of the position information included second output is high, the corrector 570 to be described later places greater importance on (higher liability in) the position information included in the second output than on the position information included in the first output and performs a correction; in a case where the foregoing reliability is low, the corrector 570 places greater importance on the position information included in the first output than on the position information included in the second output and performs a correction.

For example, the reliability identifier 550 may set higher reliability in a case where the position information included in the second output exhibits a narrower likelihood distribution. FIG. 17 illustrates an example of reliability identification by the reliability identifier 550. In FIG. 17, a position estimated by the attachment position regression estimator 540 and its likelihood distribution R10 are illustrated. For example, higher reliability is identified in a case where a difference between an upper limit and a lower limit L2 of the likelihood distribution R10 is smaller. In the example illustrated in FIG. 17, high reliability is identified, that is, greater importance is placed on the position information included in the second output, during an interval between a time $t_{21}$ and a time $t_{22}$ and an interval between a time $t_{23}$ and a time $t_{24}$. Further, in the example illustrated in FIG. 17, low reliability is identified, that is, greater importance is placed on the position information included in the first output, during an interval between the time $t_{22}$ and the time $t_{23}$.

The reliability identifier 550 outputs the identified reliability to the corrector 570.

The ground contact detector 560 performs a process of detecting contact of a foot of the body with the ground on the basis of the sensor data (angular velocities and accelerations) acquired by the sensor units 10A to 10F. Such a configuration makes it possible for the corrector 570 described later to convert the position information in the body coordinate system estimated by the attachment position regression estimator 540 into that in the global coordinate system.

The ground contact detector 560 may detect contact with the ground in, for example, a so-called zero velocity update (ZUPT: Zero Velocity Update). It is to be noted that ZUPT is a technique of correcting position by detecting a zero-velocity state as a contact state. In a case where ZUPT is used, the function of correcting the position information by the corrector 570 to be described later is also implementable by ZUPT. Further, methods by which the ground contact detector 560 detects contact with the ground are not limited to such an example, and another technique may be used to detect contact of a foot of the body with the ground.

The corrector 570 references the first output inputted from the integral calculator 520 and the second output inputted from the attachment position regression estimator 540, and corrects the position information for the attachment sites included in the first output. Note that in the following, the function of the corrector 570 may be referred to as a correction function. By virtue of such a correction function, error is less likely to become larger with time as described with reference to FIGS. 12 and 13, and it is therefore possible to estimate position information for the attachment sites with higher accuracy.

As described above, the corrector 570 may correct the position information for the attachment sites on the basis of the reliability identified by the reliability identifier 550. Such a configuration makes it possible to estimate the position information for the attachment sites with higher accuracy.

Further, on the basis of the results of ground contact detection by the ground contact detector 560, the corrector 570 converts the position information for the attachment sites in the body coordinate system (the second output) estimated by the attachment position regression estimator 540 into position information for the attachment sites in the global coordinate system. With such a configuration, it is possible to perform correction with the coordinate systems unified into the global coordinate system.

Note that the correction function of the corrector 570 may be implemented by a Kalman filter. Furthermore, it is possible for the integration function of the integral calculator 520 described above and the correction function of the corrector 570 to be implemented in combination by a Kalman filter. For example, it is possible to assume a Kalman filter having the velocity and position of each attachment site as an internal state. Such a Kalman filter integrates the accelerations of the attachment sites in the global coordinate system outputted from the global motion acceleration orientation calculator 510, and thereby predicts the velocities and positions of the attachment sites. Then, such a Kalman filter is able to correct the position information by updating the internal state sing the positions obtained by converting the position information included in the second output into that in the global coordinate system as an observation.

On the basis of the position information for the attachment sites corrected by the correcting function of the corrector 570, the interpolator 580 estimates position information for non-attachment sites and generates skeleton information. The interpolator 580 may estimate the position information for a non-attachment site located between a plurality of attachment sites in a predetermined skeleton structure, as has been described with reference to FIG. 16. Note that in the following, the function of interpolator 580 may be referred to as an interpolation function. Such an interpolation function is implementable by, for example, the inverse kinematics calculation described with reference to FIGS. 4 and 5.

As has been described with reference to FIGS. 4 and 5, in the inverse kinematics calculation, there are typically a plurality of solutions, and there may be a large number of solutions depending on the number of joint sites, for example. Therefore, in order to obtain more accurate skeleton information, a mechanism is desired that makes it possible to identify a more appropriate solution from among a large number of solutions present. Thus, the interpolator 580 according to the present embodiment estimates the position information for the non-attachment sites by regression with fitting to an inverse kinematics model prepared in advance.

Here, it is possible to generate the inverse kinematics model by, for example, learning kinematic constraint information (e.g., information including a plurality of samples of positions and orientations of various sites in postures or a series of motions acquired previously) in advance. It should be noted that various regression analysis methods are usable for the interpolation function of the interpolator 580 and, for example, methods such as DNN and Random Forest may be used alone or in combination.

Note that although it is described above that the interpolator 580 estimates position information for each site, the present embodiment is not limited to such an example. If either one of the position information and the orientation information for each site is obtained, the other is identifiable in accordance with the skeleton structure. Therefore, the interpolator 580 only has to estimate at least one of the position information or the orientation information for the non-attachment sites.

4. Operation Example

The unit configuration example and the functional configuration example of the present embodiment have been described above. Next, an operation example of the present embodiment will be described. FIG. 18 is a flowchart illustrating an operation example of the system according to the present embodiment. Note that FIG. 18 illustrates only processes that mainly represent the characteristics of the present embodiment, and the system according to the present embodiment may thus execute a process unillustrated in FIG. 18.

As illustrated in FIG. 18, first, the global motion acceleration orientation calculator 510 calculates the orientations of the sensor units 10 in the global coordinate system (S502) by AHRS on the basis on the angular velocities acquired by the gyro sensors 12. Note that step S502 corresponds to steps S111 and S121 in FIG. 12.

Subsequently, the global motion acceleration orientation calculator 510 converts the orientations of the sensor units 10 in the global coordinate system obtained in step S502 into orientations of the attachment sites to which those sensor units 10 are attached in the global coordinate system (S504).

Subsequently, the global motion acceleration orientation calculator 510 converts the accelerations in the local coordinate system acquired by the acceleration sensors 14 into acceleration in the global coordinate system (S506) on the basis of the orientations of the attachment sites in the global coordinate system obtained in step S504, Note that step S506 corresponds to steps S112 and S122 in FIG. 12.

Subsequently, the global motion acceleration orientation calculator 510 removes gravity components from the accelerations in the global coordinate system (S508) obtained in step S506 on the basis of the orientations of the attachment sites in the global coordinate system obtained in step S504.

Subsequently, the integral calculator 520 calculates the position information for the attachment sites in the global coordinate system by integrating twice the accelerations in the global coordinate system (S510), from which the gravity components are removed, obtained in step S508. Note that step S510 corresponds to steps S113 and S114 in FIG. 12.

Subsequently, whether or not to perform correction of step S510 is determined (S512). As described above, the position estimation process based on the dynamics model is higher in process load than the position estimation process based on the inertial navigation system. Accordingly, the execution frequency of the position estimation process based on the dynamics model (S514) is less than that of the position estimation process based on the inertial navigation system (S502 to S510). Thus, in step S512, it may be determined that correction is to be performed once every time the process illustrated in FIG. 18 is performed a predetermined number of times. However, the present embodiment is not limited to such an example. For example, in a case where it is determinable that the attachment sites are not stationary on the basis of the sensor data, it may be determined that correction is to be performed, whereas in a case where it is determinable that the attachment sites are stationary, it may be determined that correction is not to be performed.

In the case where it is determined that correction is to be performed (YES in S512), the attachment position regression estimator 540 estimates position information for the attachment sites in the body coordinate system by regression estimation using a dynamics model (S514). Note that step S514 corresponds to step S123 of FIG. 12.

Subsequently, the corrector 570 converts the position information for the attachment sites in the body coordinate system estimated in step S514 into position information for the attachment sites in the global coordinate system (S516) on the basis of the result of ground contact detection by the ground contact detector 560.

Then, on the basis of the position information for the attachment sites in the global coordinate system obtained in step S516, the corrector 570 corrects the position information for the attachment sites in the global coordinate system (S518) obtained in step S510.

Subsequently, the interpolator 580 estimates (interpolates) position information for the non-attachment sites (S520) by regression with fitting to an inverse kinematics model on the basis of the position information for the attachment sites in the global coordinate system. Note that the position information for the attachment sites used for the regression estimation of the position information for the non-attachment sites in step S520 may differ depending on the determination result in step S512. In the case where it is determined in step S512 that correction is to be performed, the position information for the attachment sites corrected in step S518 is used for the regression estimation in step S520. Meanwhile, in the case where it is determined in step S512 that correction is not to be performed, the position information for the attachment sites in the global coordinate system obtained in step S510 is used for the regression estimation in step S520.

The operation of the system according to the present embodiment has been described above. It is to be noted that the processing illustrated in FIG. 18 may be repeatedly executed each time sensor data is acquired by the gyro sensor 12 and the acceleration sensor 14, or at a predetermined frequency.

5. Modification Examples

One embodiment of the present disclosure has been described above. In the following, some modification examples of the present embodiment will be described. Note that the modification examples described below may be applied to the present embodiment singly or in combination. Further, each of the modification example may be applied in place of or in addition to the configuration described in the present embodiment.

<5-1. First Modification Example>

For the foregoing embodiment, an example has been described in which the attachment position regression estimator 540 performs the regression estimation process on the basis of the orientation information for the attachment sites in the global coordinate system calculated by the global motion acceleration orientation calculator 510 and the accelerations in the global coordinate system from which the gravity components have been removed. However, the present technology is not limited to such an example. For example, angular velocities and accelerations acquired by the gyro sensors 12 and the acceleration sensors 14 may be used as inputs to such a regression estimation process. Such an example will be described as a first modification example.

FIG. 19 illustrates a functional configuration example of a system according to the first modification example. Of the configuration illustrated in FIG. 19, components substantially the same as those illustrated in FIG. 15 are denoted by the same reference signs, and description thereof will thus be omitted here. A description will be given below of points different from the system illustrated in FIG. 15. Referring to FIG. 19, the system according to the present modification example differs from the system illustrated in FIG. 15 in that it includes an attachment position regression estimator 541 in place of the attachment position regression estimator 540.

The attachment position regression estimator 541 according to the present modification example performs the regression estimation process using angular velocities and accelerations acquired by the gyro sensors 12 and the acceleration sensors 14 as inputs, in addition to or in place of the information calculated by the global motion acceleration orientation calculator 510. A dynamics model to be used for such regression estimation may be prepared in advance by learning kinematic constraint information including the same kind of information (angular velocity and acceleration) as the information used for the regression estimation.

The first modification example has been described above. According to the present modification example, using more information makes it possible to estimate the position information for the attachment sites with higher accuracy. Note that the above description deals with an example in which the angular velocity and acceleration are used as inputs to the regression estimation process by the attachment position regression estimator 541; however, other information may further be used as inputs. For example, in a case where the sensor units 10 include geomagnetic sensors or barometric sensors in addition to the gyro sensors 12 and the acceleration sensors 14, information about geomagnetism or barometric pressure may be used as inputs to such a regression estimation process.

<5-2. Second Modification Example>

Next, an example in which a corrector identifies reliability will be described as a second modification example. FIG. 20 illustrates a functional configuration example of a system according to the present modification example. Of the configuration illustrated in FIG. 20, components substantially the same as those illustrated in FIG. 15 are denoted by the same reference signs, and description thereof will thus be omitted here. A description will be given below of points different from the system illustrated in FIG. 15. Referring to FIG. 20, the system according to the present modification example differs from the system illustrated in FIG. 15 in that it includes a corrector 572 in place of the reliability identifier 550 and the corrector 570.

The corrector 572 has, in addition to the function of the corrector 570 described with reference to FIG. 15, a function of identifying reliability of either the position information for the attachment sites inputted from the integral calculator 520 or that inputted from the attachment position regression estimator 540, or both. For example, such a function may be implemented by a Kalman filter, may be implemented to be performed on the basis of a rule determined in advance, or may be implemented by regression estimation using a model prepared in advance by learning.

<5-3. Third Modification Example>

Next, an example in which a correction process is performed after the position estimation (interpolation) process for the non-attachment sites will be described as a third modification example. FIG. 21 illustrates a functional configuration example of a system according to the present modification example. Of the configuration illustrated in FIG. 21, components substantially the same as those illustrated in FIG. 15 are denoted by the same reference signs, and description thereof will thus be omitted here. A description will be given below of points different from the system illustrated in FIG. 15. Referring to FIG. 21, the system according to the present modification example differs from the system illustrated in FIG. 15 in that it includes a corrector 573 and an interpolator 583 in place of the reliability identifier 550, the corrector 570, and the interpolator 580.

The interpolator 583 according to the present modification example estimates either position information or orientation information, or both, for the non-attachment sites by regression on the basis of the orientation information for the attachment sites in the global coordinate system calculated by the global motion acceleration orientation calculator 510 and the position information for the attachment sites estimated by the attachment position regression estimator 540. Note that the regression estimation by the interpolator 583 may be similar to the regression estimation for the non-attachment sites by the interpolator 580 except that information to be inputted is different. The position information or the orientation information for the non-attachment sites estimated by the interpolator 583 is outputted to the corrector 573.

It is to be noted that the second process according to the present modification example includes an interpolation process of estimating, by the foregoing interpolator 583, either position information or orientation information, or both, for the non-attachment sites. Then, the second output (the output of the second process) according to the present modification example includes either the position information or the orientation information, or both, for the non-attachment sites estimated by the interpolator 583. Further, the second output according to the present modification example may include the position information or the orientation information for the attachment sites obtained by the global motion acceleration orientation calculator 510 or the attachment position regression estimator 540. That is, the second output according to the present modification example includes either the position information or the orientation information, or both, for all the sites targeted for estimation.

On the basis of the first output (the orientation information and the position information for the attachment sites) inputted from integral calculator 520, the corrector 573 according to the present modification example corrects either the position information or the orientation information, or both, for the non-attachment sites included, in the second output that is inputted, from the interpolator 583. In the present modification example, the velocities and positions of the attachment sites and the positions or orientations of the non-attachment sites have a nonlinear relationship, and therefore the correction function of the corrector 573 according to the present modification example may be implemented by, for example, an extended. Kalman filter. In the following, an example will be described in which a correction function of correcting the orientation information for the non-attachment sites is implemented by the extended Kalman filter.

Such an extended Kalman filter has, as an internal state, velocities and positions of all the attachment sites and orientations of all the sites (including the attachment sites and the non-attachment sites) targeted for estimation. Such an extended Kalman filter predicts the velocities and positions of the attachment sites by integrating the accelerations of the attachment sites in the global coordinate system outputted from the global motion acceleration orientation calculator 510. Then, the extended Kalman filter updates the internal state by using the orientation information for all the sites targeted for estimation included in the second output as an observation, thereby being able to correct the orientation information. It is to be noted that a covariance matrix of an error that the extended Kalman filter internally has may be predicted by using a Jacobian that describes the relationship between the velocities of the attachment sites and the orientations of the non-attachment sites used in the inverse kinematics calculation.

Note that FIG. 21 illustrates the attachment position regression estimator 540 and the interpolator 583 as separate functional configurations; however, the functions of the attachment position regression estimator 540 and the interpolator 583 may be unified. In such a case, position information and orientation information for all the sites targeted for estimation may be directly estimated by regression based on the information inputted from the global motion acceleration orientation calculator 510. In such a case, there is an effect that the number of models to be prepared in advance for the regression estimation is reduced.

<5-4. Fourth Modification Example>

In the foregoing embodiment, an example in which the attachment position regression estimator 540 performs regression estimation using a non-tracking-type dynamics model has been described; however, a tracking-type dynamics model may be used. In the following, an overview of the non-tracking-type dynamics model and the tracking-type dynamics model will be described with reference to FIGS. 22 and 23.

FIG. 22 is an explanatory diagram that describes an overview of the non-tracking-type dynamics model. As illustrated in FIG. 22, in the regression estimation using the non-tracking-type dynamics model, information about acceleration and orientation is inputted to allow position information to be outputted.

FIG. 23 is an explanatory diagram that describes an overview of the tracking-type dynamics model. As illustrated in FIG. 23, also in the regression estimation using the tracking-type dynamics model, information about acceleration and orientation is inputted to allow position information to be outputted. However, in the regression estimation using the tracking-type dynamics model, position information delayed by one sample by a delayer D (i.e., the output of a previous regression estimation process) is inputted to a next regression estimation process in addition to the information about acceleration and orientation. The tracking-type dynamics model has an advantage that the tracking ability is improvable.

An example in which position information for the attachment sites is estimated by regression using such a tracking-type dynamics model will be described as a fourth embodiment. FIG. 24 illustrates a functional configuration example of a system according to the present modification example. Of the configuration illustrated in FIG. 24, components substantially the same as those illustrated in FIG. 15 are denoted by the same reference signs, and description thereof will thus be omitted here. A description will be given below of points different from the system illustrated in FIG. 15. Referring to FIG. 24, the system according to the present modification example differs from the system illustrated in FIG. 24 in that it includes an attachment position regression estimator 544 and a corrector 574 in place of the attachment position regression estimator 540 and the corrector 570.

The attachment position regression estimator 544 performs the regression estimation process by using, as an input, position information for the attachment sites that is corrected by the corrector 574 by using position information for the attachment sites estimated in a previous regression estimation process, in addition to the information calculated by the global motion acceleration orientation calculator 510. The dynamics model used for such regression estimation is the tracking-type dynamics model described above, and may be prepared in advance by learning kinematic constraint information including position information delayed by one sample, for example.

The fourth modification example described above provides improved capability of tracking various motions, thus making it possible to estimate position information for the attachment sites with higher accuracy.

<5-5. Fifth Modification Example>

In the foregoing embodiment, a unit configuration example has been described with reference to FIG. 14; however, the present technology is not limited to such an example. In the following, a unit configuration example of a system that does not include the hub unit 20 will be described as a fifth modification example. FIG. 25 illustrates a unit configuration example of a system according to the present modification example.

As illustrated in FIG. 25, the system according to the present modification example includes the sensor units 10A to 10F, the information processor 30, and the output unit 40. As illustrated in FIG. 25, in the present modification example, the sensor units 10 are directly connected to the information processor 30 without the hub unit 20 therebetween. It is to be noted that the sensor units 10 and the information processor 30 may be connected to each other in a wired manner or wirelessly. Except for such a connection relationship, each of the units illustrated in FIG. 25 may have a similar configuration to that of a corresponding unit denoted by the same reference sign in FIG. 14.

<5-6. Sixth Modification Example>

In the foregoing embodiment, an example in which regression estimation is performed using a dynamics model and an inverse kinematics model has been described. The estimation result of this regression estimation can vary greatly depending on the kinematic constraint information used for learning to generate the dynamics model and the inverse kinematics model. For example, in a case where kinematic constraint information obtained by sensing a characteristic posture or motion is used for learning, the estimation result tends to have a characteristic closer to the motion used for learning than to the actual motion of the body.

Examples of the characteristic posture or motion include, but are not limited to, postures unique to characters such as zombies, dynamic motions typical of fighting scenes, postures frequently appearing in games such as shooting games, choreographed motions characteristic of each genre of dance, motions based on individual rules of each sport, etc.

By appropriately preparing the kinematic constraint information as described above to suit the application and using it for learning to generate a dynamics model and an inverse kinematics model, it is possible to estimate skeleton information appropriate to the application. As a result, for example, in a case of producing an animation on the basis of skeleton information, it is possible to produce a characteristic animation without involving postprocessing on the skeleton information estimated through the series of processes described above.

6. Overview of Second Embodiment

In the foregoing embodiment of the present disclosure, as described previously, the process of detecting contact of a foot of the body with the ground is performed by the ground contact detector 560 in order to convert the position information in the body coordinate system estimated by the attachment position regression estimator 540 or the like into that in the global coordinate system. For example, the ground contact detector 560 is able to utilize a technique of correcting position by using ZUPT, in other words, by detecting a state in which the velocity is zero (a predetermined velocity) as a contact state.

<6-1. First ZUPT Technique>

First, a description will be given of a first ZUPT technique with reference to FIGS. 26 and 27. FIGS. 26 and 27 are explanatory diagrams that describe the first ZUPT technique according to the present embodiment.

The first ZUPT technique utilizes sensor data acquired by the sensor units 10, which include inertial sensors such as acceleration sensors and gyro sensors, attached to forefeet (specifically, toes or insteps) as illustrated in FIG. 26.

Specifically, in the first ZUPT technique, as illustrated in FIG. 27, the sensor data is acquired from the foregoing sensor units 10, and the accelerations of the sensor units 10 in the local coordinate system and the angular velocities of the sensor units 10 in the local coordinate system included in the sensor data are acquired. Then, in the first ZUPT technique, the above-described process based on the inertial navigation system is performed on the acquired accelerations and angular velocities to thereby acquire accelerations, velocities, and positions in the global coordinate system (S600).

Next, in this technique, the foregoing sensor data is used to detect a state in which the velocity of a forefoot is zero (S601). In this detection, in the technique, the dispersion of the acceleration included in the foregoing sensor data, the norm of the angular velocity, or the like may be compared with a threshold value, or the state in which the velocity is zero may be detected from the acceleration or angular velocity by machine learning, and thus there is no specific limitation.

Then, in this technique, if it is detected that the velocity of a forefoot is zero, the position of the forefoot in the global coordinate system acquired in step S600 by the process based on the inertial navigation system is corrected (S602) on the assumption that the velocity of the forefoot in the global coordinate system acquired in S600 by the process based on the inertial navigation system is zero. A Kalman filter or the like is usable for the above correction. For example, with such a Kalman filter, it is possible to predict the position of the forefoot in the global coordinate system by integrating the acceleration of the forefoot in the global coordinate system. Furthermore, the Kalman filter makes it possible to correct the position of the forefoot in the global coordinate system by updating the internal state using an observation value where the velocity of the forefoot is assumed as zero.

<6-2. Second ZUPT Technique>

Next, a second ZUPT technique will be described with reference to FIGS. 28 and 29. FIGS. 28 and 29 are explanatory diagrams that describe the second ZUPT technique according to the present embodiment.

Incidentally, in motion capture, the foregoing sensor unit 10 is not always attached to a forefoot as illustrated in FIG. 26 but may be attached to, for example, an ankle, calf, or the like as illustrated in FIG. 28. As a characteristic of a human motion, when a forefoot contacts the ground, the velocity of the forefoot surely becomes zero within a certain period of time, whereas the velocity of an ankle or the like is less likely to become zero. In a case where, e.g., a running motion is made in motion capture, the above-described tendency may become noticeable, in particular. Accordingly, in a case where ZUPT is performed using sensor data of the sensor unit 10 attached to an ankle or the like, it is sometimes difficult to correct the position in the global coordinate system with high accuracy because the velocity is less likely to become zero within a certain period of time.

Furthermore, according to the study by the present inventors, in a case where a motion of the body obtained by motion capture in a configuration in which the sensor unit 10 is attached to an ankle and no sensor unit 10 is attached to a forefoot is reproduced in a skeleton structure representing the structure of the body, accurate reproduction is achievable for the region from the waist to the ankle of a human. However, because a forefoot or a like site places less constraints on a human body than a knee or a like site, the motion thereof is difficult to reproduce with high accuracy. In particular, in a case where a body motion obtained by motion capture is applied to an animation or the like in which an avatar makes a motion, the avatar's forefeet may sometimes be unsteady in the animation, resulting in lack of weightiness of the avatar.

In view of the above-described situations, the present inventors have conceived their own idea of using sensor data of the sensor unit 10 attached to an ankle or the like to estimate a state in which the velocity of a forefoot is zero, and have consequently created the second TUFT technique according to the present embodiment described below. The second ZUPT technique estimates the velocity of the forefoot indirectly. Therefore, even when a running motion is motion-captured, it is possible to detect with stability a state in which the velocity of a forefoot is zero, which allows for more robust correction of the position of the forefoot. Furthermore, according to the second ZUPT technique, it is possible to control the forefeet of an avatar described above by using the estimated forefoot velocity or forefoot position. Thus, in a case where the motion of the avatar's forefoot contacting the ground is reproduced in an animation, it is possible to reproduce a stable forefoot behavior.

Specifically, in the second ZUPT technique, as illustrated in FIG. 29, sensor data is acquired from the sensor unit 10 attached to an ankle, calf, or the like to acquire the acceleration of the sensor unit 10 in the local coordinate system and the angular velocity of the sensor unit 10 in the local coordinate system included in the sensor data. Then, in the second ZUPT technique, the foregoing process based on the inertial navigation system is performed on the acquired acceleration and angular velocity to thereby acquire the acceleration and orientation of the sensor unit 10 in the global coordinate system (S610).

Next, in this technique, the velocity of the forefoot is estimated (S611) by using the sensor data (the acceleration and angular velocity of the sensor unit 10 in the local coordinate system) and the acceleration and orientation of the sensor unit 10 in the global coordinate system based on the inertial navigation system. Then, in this technique, the position of the forefoot as viewed from the ankle is estimated (S612) by using the sensor data (the acceleration and angular velocity of the sensor unit 10 in the local coordinate system) and the acceleration and orientation of the sensor unit 10 in the global coordinate system based on the inertial navigation system. Furthermore, in this technique, a fusion process of fusing the acceleration and orientation of the sensor unit 10 in the global coordinate system, the estimation result for the velocity of the forefoot, and the estimation result for the position of the forefoot acquired through the foregoing steps is performed (S613). As a result, in this technique, it is possible to acquire corrected positions of the ankle and forefoot in the global coordinate system. The details of processing in each step will be described later.

<6-3. Functional Configuration Example>

The overviews of the first and second ZUPT techniques according to the present embodiment have been described above. Next, as one example, a system functional configuration according to the second ZUPT technique of the present embodiment will be described with reference to FIG. 30. FIG. 30 illustrates an example of the functional configuration of the system according to the present embodiment. Note that FIG. 30 illustrates only the functional configuration that mainly represents the characteristics of the present embodiment, and the system according to the present embodiment may include the functional configuration illustrated in FIG. 15.

Referring to FIG. 30, the system according to the present embodiment has functions as the global motion acceleration orientation calculator 510, the integral calculator 520, the selector 530, the attachment position regression estimator 540, the reliability identifier 550, the ground contact detector 560, the corrector 570, the interpolator 580, and an estimator 561. It is to be noted that the global motion acceleration orientation calculator 510, the integral calculator 520, the selector 530, the attachment position regression estimator 540, the reliability identifier 550, the ground contact detector 560, the corrector 570, and the interpolator 580 illustrated in FIG. 30 are the same as those in the functional configuration of the system according to the first embodiment described with reference to FIG. 15. Thus, the description thereof will be omitted here and only the estimator 561 different from the first embodiment will be described. Further, each functional configuration of FIG. 30 described below may be implemented by any of the units illustrated in FIG. 14, and is not particularly limited.

The estimator 561 estimates the velocity of the forefoot and the position of the forefoot as viewed from the ankle by using the sensor data (the acceleration and angular velocity of the sensor unit 10 in the local coordinate system) and the acceleration and orientation of the sensor unit 10 in the global coordinate system from the integral calculator 520, and outputs the estimation results to the corrector 570.

<6-4. Operation Example>

The functional configuration example according to the present embodiment has been described above. Next, an operation example of the second ZUPT technique of the present embodiment will be described with reference to FIG. 31. FIG. 31 is a flowchart illustrating an operation example of the system according to the present embodiment. Note that FIG. 31 illustrates only the processes that mainly represent the characteristics of the present embodiment, and the system according to the present embodiment may execute a process unillustrated in FIG. 31.

As illustrated in FIG. 31, the global motion acceleration orientation calculator 510 and the estimator 561 acquire sensor data (the acceleration and angular velocity of the sensor unit 10 in the local coordinate system) from the sensor unit 10 attached to the ankle, calf, or the like (S700). Then, the global motion acceleration orientation calculator 510 and the integral calculator 520 calculate the acceleration and orientation of the sensor unit 10 in the global coordinate system (S702) by performing the foregoing process based on the inertial navigation system on the acceleration and angular velocity acquired in step S700.

Subsequently, the estimator 561 estimates the velocity of the forefoot (S704) by using the sensor data (the acceleration and angular velocity of the sensor unit 10 in the local coordinate system) acquired in step S700 and the acceleration and orientation of the sensor unit 10 in the global coordinate system based on the inertial navigation system calculated in step S702. In addition, the estimator 561 estimates the position of the forefoot (S706) as viewed from the ankle by using the sensor data (the acceleration and angular velocity of the sensor unit 10 in the local coordinate system) acquired in step S700 and the acceleration and orientation of the sensor unit 10 in the global coordinate system based on the inertial navigation system calculated in step S702.

Next, the corrector 570 executes a correction by the ZUPT process on the velocity of the forefoot estimated in step S704, and executes a fusion process of fusing the position of the forefoot estimated in step S706 (S708).

Further, the details of each of steps S704, S706, and S708 illustrated in FIG. 31 will be described with reference to FIGS. 32 and 33. FIG. 32 is an explanatory diagram that describes estimation of forefoot velocity according to the present embodiment, and FIG. 33 is an explanatory diagram that describes estimation of forefoot position according to the present embodiment.

(Estimation of Velocity of Forefoot)

The estimator 516 estimates the velocity of the forefoot in step S704 described above. Specifically, first, the acceleration and the angular velocity of the sensor unit 10 in the local coordinate system included in the sensor data acquired by the sensor unit 10 attached to the ankle are inputted to the estimator 516, as illustrated in FIG. 32. Further, the acceleration and the orientation of the sensor unit 10 in the global coordinate system obtained by performing the above-described process based on the inertial navigation system on the acceleration and the angular velocity of the sensor unit 10 in the local coordinate system included in the sensor data are inputted to the estimator 516. It is to be noted that in estimating the velocity of the forefoot, any one or two of the foregoing sensor data (the acceleration and the angular velocity in the local coordinate system), the foregoing acceleration in the global coordinate system, or the foregoing orientation in the global coordinate system may be inputted to the estimator 516. Further, in estimating the velocity of the forefoot, sensor data of the sensor units 10 attached to other sites, or accelerations and orientations thereof in the global coordinate system obtained by subjecting that sensor data to the process based on the inertial navigation system may be inputted to the estimator 516, and thus there is no specific limitation.

Based on the inputs described above, the estimator 516 then estimates the velocity of the forefoot in accordance with pre-described rules. In the present embodiment, the estimator 516 may estimate the velocity of the forefoot by using machine-learned classifications and regressions. In this case, the estimator 516 is able to output a binary label in which the velocity of the forefoot is either zero or non-zero as an estimation result. Further, the present embodiment is not limited to outputting such a binary label as an estimation result. In the present embodiment, for example, a ternary or higher-valued label in which the velocity of the forefoot is "0 m/s$^2$ or more and less than 0.01 m/s$^2$", "0.01 m/s$^2$ or more and less than 0.10 m/s$^2$", "0.10 m/s$^2$ or more", or the like may be outputted. Further, in the present embodiment, instead of such a label, the velocity itself of the forefoot may be estimated and outputted.

(Estimation of Position of Forefoot)

The estimator 516 estimates the position of the forefoot as viewed from the ankle in step S706 described above. Specifically, as illustrated in FIG. 33, the acceleration and the angular velocity in the local coordinate system included in the sensor data acquired by the sensor unit 10 attached to the ankle are inputted to the estimator 516. Further, the acceleration and the orientation of the sensor unit 10 in the global coordinate system obtained by performing the above-described process based on the inertial navigation system on the acceleration and the angular velocity of the sensor unit 10 in the local coordinate system included in the sensor data are inputted to the estimator 516. It is to be noted that in estimating the position of the forefoot, one or two of the foregoing sensor data (the acceleration and the angular velocity in the local coordinate system), the foregoing acceleration in the global coordinate system, or the foregoing orientation in the global coordinate system may be inputted to the estimator 516. Further, in estimating the position of the forefoot, sensor data of the sensor units 10 attached to other sites, or accelerations and orientations thereof in the global coordinate system obtained by subjecting that sensor data to the process based on the inertial navigation system may be inputted to the estimator 516, and thus there is no specific limitation. Furthermore, body parameters such as height or lengths of leg parts (for example, leg length above knees or leg length below knees) may be inputted to the estimator 516 as illustrated in FIG. 33.

Then, on the basis of the foregoing inputs, the estimator 516 estimates the position of the forefoot in accordance with pre-described rules. In the present embodiment, the estimator 516 may estimate the velocity of the forefoot by using machine-learned classifications and regressions.

(Fusion Process)

In step S708 described above, the corrector 570 performs a fusion process of fusing the acceleration and the orientation in the global coordinate system, the estimated velocity of the forefoot, and the estimated position of the forefoot. The corrector 570 is able to perform the fusion process by using, for example, a Kalman filter or the like that fuses a plurality of data, placing higher weight on data having higher reliability. With such a Kalman filter, for example, in a case of a binary label in which the velocity of the forefoot estimated in step S704 is either zero or non-zero, it is possible to correct the observation value for the label of the zero velocity. Further, with the Kalman filter, for example, in a case of a multivalued label having three or more values for the estimated forefoot velocity, it is possible to suitably perform the fusion process by imparting reliability in a manner in which the reliability is sequentially made lower for a label closer to the zero velocity to thereby reduce the reliability of the vector of the zero velocity.

As described above, according to the second ZUPT technique of the present embodiment, it is possible to estimate the velocity of the forefoot indirectly. Therefore, even when a running motion is motion-captured, it is possible to detect with stability a state in which the velocity of the forefoot is zero, which allows for more robust correction of the position of the forefoot. Furthermore, according to the second ZUPT technique, it is possible to control the foregoing forefeet of an avatar by using the estimated forefoot velocity or forefoot position. Thus, in a case where the motion of the avatar's forefoot contacting the ground is reproduced in an animation, it is possible to reproduce a stable forefoot behavior.

<6-5. Modification Example 1>

In the foregoing embodiment, sensor data of the sensor unit 10 attached to one ankle is used; however, in the present embodiment, this is non-limiting and sensor data of the sensor units 10 attached to both ankles may be used. By doing so, it is possible to perform ZUPT with higher accuracy. Thus, a modification example that uses sensor data of the sensor units 10 attached to both ankles will be described with reference to FIGS. 34 to 36, as modification example 1 of the present embodiment. FIG. 34 is an explanatory diagram that describes a ZUPT technique according to modification example 1. FIG. 35 is an explanatory diagram that describes estimation of a relative position according to modification example 1. Further, FIG. 36 is a flowchart illustrating an operation example of a system according to modification example 1.

Specifically, in the present modification example 1, sensor data is acquired from the sensor unit 10 attached to the right ankle, the sensor unit 10 attached to the left ankle, and the sensor unit 10 attached to another site, as illustrated in FIG. 34. Further, in the present modification example 1, acceleration and angular velocity of the right ankle in the local coordinate system, acceleration and angular velocity of the left ankle in the local coordinate system, and acceleration and angular velocity of the other site in the local coordinate system are acquired. Then, in the present modification example 1, the foregoing process based on the inertial navigation system is performed on the acquired acceleration and angular velocity of the right ankle, and thereby acceleration and orientation of the right ankle in the global coordinate system are acquired (S800).

Furthermore, similarly to the foregoing, in the present modification example 1, the above-described process based on the inertial navigation system is performed on the acquired acceleration and angular velocity of the left ankle, and thereby acceleration and orientation of the left ankle in the global coordinate system are acquired (S802). Furthermore, in the present modification example 1, the foregoing process based on the inertial navigation system is performed on the acquired acceleration and angular velocity of the other site, and thereby acceleration and orientation of the other site in the global coordinate system are acquired (S804).

Next, in the present modification example, respective velocities of both forefeet are estimated (S806) by using the accelerations and orientations of the right ankle, the left ankle, and the other site in the global coordinate system based on the inertial navigation system. Then, in the present modification example, respective positions of both forefeet are estimated (S808) by using the accelerations and orientations of the right ankle, the left ankle, and the other site in the global coordinate system based on the inertial navigation system. Further, in the present modification example, relative positions (R20 illustrated in FIG. 35) of both ankles are estimated (S810) by using the accelerations and orientations of the right ankle, the left ankle, and the other site in the global coordinate system based on the inertial navigation system.

In the present modification example, relative positions of both ankles are newly estimated and this makes it possible to acquire positions of the ankles and forefeet in the global coordinate system stronger in restriction. In the estimation, similarly to the estimation in the foregoing embodiment, it is possible to use machine learning. Further, in estimating the velocities of both ankles, the positions of both ankles, and the relative positions of both ankles, not only the accelerations and orientations of the right ankle, the left ankle, and other site in the global coordinate system based on the inertial navigation system but also the accelerations and angular velocities of the right ankle, the left ankle, and the other site in the local coordinate system included in the sensor data may be used, or body parameters such as height or lengths of leg parts may be used, and thus there is no particular limitation.

Further, in the present modification example, a fusion process of fusing the estimation result of the velocities of both forefeet, the estimation result of the positions of both forefeet, and the relative positions of both ankles is performed (S812). Note that as with the foregoing, it is also possible to perform processing in the fusion process in the present modification example by using a Kalman filter or the like that estimates the states of velocities and positions of both ankles and both forefeet. As a result, in the present modification example, it is possible to acquire corrected positions of the ankles and forefeet in the global coordinate system.

The operation of modification example 1 described above is summarized as follows. As illustrated in FIG. 36, the global motion acceleration orientation calculator 510 and the estimator 561 acquire sensor data (accelerations and angular velocities of both ankles and the other site in the local coordinate system) from the sensor units 10 attached to both ankles and so on (S820). Then, the global motion acceleration orientation calculator 510 and the integral calculator 520 perform the foregoing process based on the inertial navigation system on the accelerations and angular velocities acquired in step S820, and thereby calculate accelerations and orientations of both ankles and the other site in the global coordinate system (S822).

Subsequently, the estimator 561 estimates velocities of both forefeet (S824) by using the accelerations and orientations of both ankles and the other site in the global coordinate system based on the inertial navigation system calculated in step S822. In addition, the estimator 561 estimates respective positions of both forefeet as viewed from both ankles by using both ankles and the other site in the global coordinate system based on the inertial navigation system calculated in step S822.

Next, the estimator 561 estimates relative positions (R20 illustrated in FIG. 35) of both ankles (S828) by using the accelerations and orientations of both ankles and the other site in the global coordinate system based on the inertial navigation system. Further, the corrector 570 performs correction by the ZUPT process to the velocities of both forefeet estimated in step S824, and performs the fusion process (S830) of fusing the positions of both forefeet estimated in step S826 and the relative positions of both ankles estimated in step S828.

In the present modification example described above, the relative positions of both ankles are newly estimated by using the sensor data, etc. of the sensor units 10 attached to both ankles, and therefore it is possible to acquire positions of the ankles and forefeet in the global coordinate system stronger in restriction. As a result, in the present modification example, it is possible to perform ZUPT with higher accuracy.

<6-6. Modification Example 2>

In the foregoing modification example 1, the relative positions of both ankles are estimated; however, sensor data from a distance sensor for measuring relative positions may further be used. By doing so, it becomes possible to perform ZUPT with higher accuracy. Thus, a modification example that uses sensor data from a distance sensor for measuring relative positions will be described with reference to FIGS. 37 and 38, as modification example 2 of the present embodiment. FIG. 37 illustrates an example of a unit configuration of the sensor unit 10 according to modification example 2, and FIG. 38 is an explanatory diagram that describes a ZUPT technique according to modification example 2.

As illustrated in FIG. 37, a system according to the present modification example 2 may include a sensor unit 10G. The sensor unit 10G includes the gyro sensor 12, the acceleration sensor 14, the controller 16, and the communicator 18, for example, like the sensor unit 10 illustrated in FIG. 14. In addition, the sensor unit 10G may further include a distance sensor 50 that is able to measure a relative distance between both ankles. The distance sensor 50 may be, for example, an ultrasonic sensor or the like that is able to measure the distance by the reflection of ultrasonic waves.

Specifically, in the present modification example 2, as illustrated in FIG. 34, sensor data is acquired from the sensor unit 10 attached to the right ankle, the sensor unit 10 attached to the left ankle, and the sensor unit 10 attached to another site. Furthermore, in the present modification example 2, sensor data regarding the relative distance between both ankles is acquired from the distance sensor 50. Then, in the present modification example 2, the foregoing process based on the inertial navigation system is performed on the accelerations and angular velocities acquired for both ankles, and thereby accelerations and orientations of both ankles in the global coordinate system are obtained (S900, S904). Further, in the present modification example 2, the foregoing process based on the inertial navigation system is performed on the acceleration and angular velocity acquired for the other site, and thereby an acceleration and an orientation of the other site in the global coordinate system are obtained (S904).

Next, in the present modification example, respective velocities and positions of both forefeet and further, relative positions of both ankles are estimated (S906, S908, S910) by using the accelerations and orientations of the right ankle, the left ankle, and the other site in the global coordinate system based on the inertial navigation system, and further, the relative distance between both ankles included in the sensor data.

Further, in the present modification example, a fusion process of fusing the estimation result of the velocities of both forefeet, the estimation result of the positions of both forefeet, the relative positions of both ankles, and further, the relative distance between both ankles included in the sensor data is executed (S912).

As above, the foregoing modification example 2 makes it possible to perform ZUPT with higher accuracy by newly using the sensor data of the distance sensor that measures relative positions.

7. Hardware Configuration Example

The embodiments of the present disclosure have been described above. Finally, with reference to FIG. 39, a description will be given of a hardware configuration of an information processor according to an embodiment of the present disclosure. FIG. 39 is a block diagram illustrating an example of the hardware configuration of the information processor according to the embodiment of the present disclosure. It is to be noted that the information processor 900 illustrated in FIG. 39 is able to implement, for example, the sensor unit 10, the hub unit 20, and the information processor 30 illustrated in FIG. 14. Information processing by the sensor unit 10, the hub unit 20, and the information processor 30 according to the embodiment of the present disclosure is implemented by cooperation of software and hardware described below.

As illustrated in FIG. 39, the information processor 900 includes a CPU (Central Processing Unit) 901, a ROM (Read Only Memory) 902, a RAM (Random Access Memory) 903, and a host bus 904a. Further, the information processor 900 includes a bridge 904, an external bus 904b, an interface 905, an input unit 906, an output unit 907, a storage unit 908, a drive 909, a connection port 911, a communication unit 913, and a sensor 915. The information processor 900 may include a processing circuit such a DSP or an ASIC in place of or in conjunction with the CPU 901.

The CPU 901 functions as an arithmetic processing unit and a control unit, and controls overall operations in the information processor 900 in accordance with various programs. Further, the CPU 901 may be a microprocessor. The ROM 902 stores programs, arithmetic parameters, etc. that the CPU 901 uses. The RAM 903 temporarily stores a program that is used in execution of the CPU 901, parameters that change appropriately in execution thereof, and the like. The CPU 901 may form, for example, the controller 16, the controller 24, and the controller 34.

The CPU 901, the ROM 902, and the RAM 903 are connected to each other by the host bus 904a including a CPU bus and the like. The host bus 904a is connected to the external bus 904b such as a PCI (Peripheral Component Interconnect/interface) bus via the bridge 904. Note that the host bus 904a, the bridge 904, and the external bus 904b are not necessarily configured separately, and these functions may be packaged in a single bus.

The input unit 906 is implemented by, for example, a unit through which the user inputs information, such as a mouse, a keyboard, a touch panel, a button, a microphone, a switch, and a lever. Further, the input unit 906 may be a remote-control unit that uses infrared ray or other electromagnetic waves, or may be external connection equipment such as a mobile phone or a PDA compatible with operations of the information processor 900. Further, the input unit 906 may include, for example, an input control circuit or the like that generates an input signal on the basis of information inputted by the user using the input means described above and outputs the generated input signal to the CPU 901. It is possible for the user of the information processor 900 to input various data or provide instructions for a processing operation to the information processor 900 by operating the input unit 906.

The output unit 907 is formed by a unit that is able to notify the user of acquired information visually or audibly. Examples of such a unit include a display unit such as a CRT display unit, a liquid crystal display unit, a plasma display unit, an EL display unit and a lamp, a sound output unit such as a speaker and a headphone, a printer unit, etc. The output unit 907 outputs, for example, results obtained through various processes performed by the information processor 900. Specifically, the display visually displays the results obtained through various processes performed by the information processor 900 in a variety of formats, such as text, images, tables, graphs, etc. Meanwhile, the sound output unit converts audio signals including reproduced sound data, acoustic data or the like into analog signals and outputs the analog signals audibly.

The storage unit 908 is a data storing unit formed as an example of a memory section of the information processor 900. The storage unit 908 is implemented by, for example, a magnetic memory section device such as an HDD, a semiconductor memory device, an optical memory device, a magneto-optical memory device or the like. The storage unit 908 may include a storage medium, a recording unit for recording data on the storage medium, a reading unit for reading data from the storage medium, a deletion unit for deleting data recorded on the storage medium, etc. The storage unit 908 stores a program to be executed by the CPU 901, various data, and various externally acquired data, etc.

The drive 909 is a reader/writer for a storage medium, and is incorporated in or externally attached to the information processor 900. The drive 909 reads information recorded on a removable storage medium mounted thereon, such as a magnetic disk, an optical disk, a magneto-optical disk, or a semiconductor memory, and outputs the information to the RAM 903. The drive 909 is also able to write information on the removable storage medium.

The connection port 911 is an interface to be connected to external equipment, and is a connector to the external equipment that is able to transmit data through, for example, a USB (Universal Serial Bus) or the like.

The communication unit 913 is, for example, a communication interface formed by a communication device or the like for connection to a network 920. The communication unit 913 may be, for example, a communication card or the like for wired or wireless LAN (Local Area Network), LTE (Long Term Evolution), Bluetooth (registered trademark), or WUSB (Wireless USB). Further, the communication unit 913 may be a router for optical communication, a router for ADSL(Asymmetric Digital Subscriber Line), modems for various types of communications, or the like. The communication unit 913 is able to transmit and receive signals or the like to and from the Internet or other communication equipment in accordance with predetermined protocols such as TCP/IP, for example. The communication unit 913 may form, for example, the communicator 18, the communicator 22, and the communicator The sensor 915 is a sensor of any type such as an acceleration sensor, a gyro sensor, a geomagnetic sensor, an optical sensor, a sound sensor, a range-finding sensor, or a force sensor, for example. The sensor 915 acquires information about the state of the information processor 900 itself, such as the orientation, moving speed or the like of the information processor 900, and information about a surrounding environment of the information processor 900, such as brightness or noise around the information processor 900. Further, the sensor 915 may include a GPS sensor that receives a GPS signal to measure the latitude, longitude, and altitude of the unit. The sensor 915 may form, for example, the gyro sensor 12 and the acceleration sensor 14.

Note that the network 920 is a wired or wireless transmission path for information transmitted from units connected to the network 920. For example, the network 920 may include a public network such as the Internet, a telephone network or a satellite communication network, various LANs (Local Area Networks) including Ethernet (registered trademark), WAN (Wide Area Network), and the like. Further, the network 920 may include a dedicated line network such as an IP-VPN (Internet Protocol-Virtual Private Network).

An example of a hardware configuration that is able to implement the functions of the information processor 900 according to the embodiment of the present disclosure has been described above. Each of the above-described components may be implemented by using a general-purpose member, or may be implemented by hardware specialized for the function of the component. Accordingly, it is possible to appropriately change the hardware configuration to be used in accordance with the technical level at the time of carrying out the embodiments of the present disclosure.

It is to be noted that it is possible to create a computer program for implementing each of the functions of the information processor 900 according to the embodiments of the present disclosure as described above and to install the computer program in a PC, etc. Further, it is also possible to provide a computer-readable recording medium in which such a computer program is stored. The recording medium is, for example, a magnetic disk, an optical disk, a magneto-optical disk, a flash memory, or the like. In addition, the computer program described above may be distributed via a network, for example, without using a recording medium.

8. Conclusion

As described above, according to the embodiments of the present disclosure, it is possible to obtain, with higher accuracy, position information for the sites of the body to which the motion sensors are attached. Further, according to the embodiments of the present disclosure, it is also possible to obtain position information and orientation information for the sites to which no motion sensors are attached. This makes it possible to obtain skeleton information using a smaller number of motion sensors.

Preferred embodiments of the present disclosure have been described above in detail with reference to the accompanying drawings; however, the technical scope of the present disclosure is not limited to such examples. It is apparent that those skilled in the art of the present disclosure may conceive various alterations or modifications within the scope of the technical idea described in the claims, and it should be understood that such alterations and modifications are also within the technical scope of the present disclosure.

For example, in the foregoing embodiments, an example in which an inertial sensor is attached to the body as the motion sensor has been mainly described; however, the present technology is not limited to such an example. The motion sensor only has to be a sensor that senses movements of a body, and may be a geomagnetic sensor, a barometric sensor, an image sensor, or the like as described above.

In addition, the steps in the foregoing embodiments may not necessarily be processed on a time-series basis in accordance with the order described herein as the flowchart. For example, the steps in the processes of the foregoing embodiments may be processed in an order different from the order described as the flowchart, or may be processed in parallel.

In addition, the effects described herein are merely illustrative or exemplary, and are non-limiting. That is, the technology according to the present disclosure may achieve other effects that are apparent to those skilled in the art from the description herein, in addition to the effects described above or in place of the effects described above.

It is to be noted that the following configurations are also encompassed by the technical scope of the present disclosure.

(1)
A program that causes a computer to implement a correction function of referencing a first output obtained by performing a first process on sensor data acquired by two or more motion sensors attached to two or more sites of a body and a second output obtained by performing a second process on the sensor data, and correcting position information for attachment sites to which the motion sensors are attached.

(2)
The program according to (1), in which
the sensor data includes an acceleration
the first process includes integration of the acceleration, and the first output includes the position information for the attachment sites obtained by the integration.

(3)
The program according to (1) or (2), in which
the sensor data includes an acceleration,
the second process includes a regression estimation process of estimating the position information for the attachment sites by regression, and
the regression estimation process is performed on the basis of the acceleration.

(4)
The program according to (3), in which
the sensor data further includes an angular velocity, and
the regression estimation process is performed further on the basis of the angular velocity.

(5)
The program according to (4), in which the acceleration, after being subjected to a coordinate system conversion on the basis of the angular velocity, is used as an input to the regression estimation process.

(6)
The program according to (4) or (5), in which orientation information for the attachment sites obtained on the basis of the angular velocity is used as an input to the regression estimation process.

(7)
The program according to any one of (4) to (6), in which the acceleration or the angular velocity acquired by the motion sensors is used as an input to the regression estimation process.

(8)
The program according to any one of (3) to (7), in which the regression estimation process is performed on the basis of position information for the attachment sites previously estimated by the regression estimation process.

(9)
The program according to any one of (1) to (8), further causing the computer to implement an interpolation function of estimating, on the basis of the position information for the attachment sites corrected by the correction function, position information or orientation information for a non-attachment site to which none of the motion sensors is attached.

(10)
The program according to (9), in which the interpolation function estimates the position information or the orientation information for the non-attachment site located between a plurality of the attachment sites in a predetermined skeleton structure.

(11)
The program according to (9) or (10), in which the interpolation function estimates the position information or the orientation information for the non-attachment site by regression.

(12)
The program according to any one of (9) to (11), further causing the computer to implement a reliability identification function of identifying reliability that indicates reliability of the position information for the attachment sites included in the first output or the second output.

(13)
The program according to (12), in which the correction function corrects the position information for the attachment sites on the basis of the reliability identified by the reliability identification function.

(14)
The program according to any one of (3) to (8), in which the second process further includes an interpolation process of estimating, on the basis of the position information for the attachment sites estimated through the regression estimation process, position information or orientation information for a non-attachment site to which none of the motion sensors is attached.

(15)
The program according to (14), in which the correction function further corrects the position information or the orientation information for the non-attachment site included in the second output on the basis of the first output.

(16)

The program according to any one of (9) to (15), in which the correction function is implemented by a Kalman filter.

(17)

The program according to (1), in which the correction function detects a ground contact state and corrects the position information for the attachment sites on the basis of a detection result.

(18)

The program according to (17), in which correction function estimates a velocity and a position of a forefoot using an acceleration and an angular velocity included in the sensor data, and detects the ground contact state on the basis of an estimation result, the ground contact state being a state in which the forefoot has a predetermined velocity, (19)

An information processor including a corrector that references a first output obtained by performing a first process on sensor data acquired by two or more motion sensors attached to two or more sites of a body and a second output obtained by performing a second process on the sensor data, and corrects position information for attachment sites to which the motion sensors are attached.

(20)

An information processing method including: referencing, by a processor, a first output obtained by performing a first process on sensor data acquired by two or more motion sensors attached to two or more sites of a body and a second output obtained by performing a second process on the sensor data; and correcting, by the processor, position information for attachment sites to which the motion sensors are attached.

REFERENCE SIGNS LIST 10, 10A, 10B, 10C, 10D, 10E, 10F, 10G: Sensor unit
12: Gyro sensor
14: Acceleration sensor
16: Controller
18, 32: Communicator
20: Hub unit
22: Communicator
24, 34: Controller
30: Information processor
40, 907: Output unit
50: Distance sensor
510: Global motion acceleration orientation calculator
520: Integral calculator
530: Selector
540, 541, 544: Attachment position regression estimator
550: Reliability identifier
560: Ground contact detector
561: Estimator
570, 572, 573, 574: Corrector
580, 583: Interpolator
900: Information processor
901: CPU
902: ROM
903: RAM
904: Bridge
904a: Host bus
904b: External bus
905: Interface
906: Input unit
908: Storage unit
909: Drive
911: Connection port
913: Communication unit
915: Sensor
920: Network
D: Delayer
D103, D104, D105, SD10, SD90, SD100, SD101, SD102, SD103, SD104, SD105: Skeleton structure
L1: Upper limit
L2: Lower limit
P11, P12, P13, P14, P15, P16, P101, P102, P103, P104, P105, P106, SP101, SP102, SP103, SP105, SP106, SP107: Attachment site
PD10, PD12, PD100: Attachment site information
R10: Likelihood distribution
R20: Relative position
S100, S111, S112, S113, S114, S121, S122, S123, S130, S200, S502, S504, S506, S508, S510, S512, S514, S516, S518, S520, S600, S601, S602, S610, S611, S612, S613, S700, S702, S704, S706, S708, S710, S800, S802, S804, S806, S808, S810, S812, S900, S902, S904, S906, S908, S910, S912: Step
S53, S54, S55, S56, S57, S58, S59: Position estimation process
SB101, SB81, SB82: Bone
SP11, SP12, SP20, SP8I, SP82, 5P83, SP91, SP92, SP93, SP94, SP95, SP96: Site
U1: User

The invention claimed is:

1. A non-transitory computer-readable medium having embodied thereon a program, which when executed by a computer causes the computer to execute an information processing method, the method comprising:

implementing a correction function of referencing a first position information obtained by performing a first process on sensor data acquired by two or more motion sensors attached to two or more sites of a body and a second position information estimated by using a learning model on the sensor data;

correcting the first position information for attachment sites to which the motion sensors are attached on a basis of the second position information; and implementing an interpolation function of estimating, on a basis of the first position information for the attachment sites corrected by the correction function, position information for a non-attachment site of the body to which none of the motion sensors are attached, the position information for the non-attachment site not including the first position information for the attachment sites, wherein the first position information and the second position information include coordinates of the attachment sites in a coordinate system and the position information for the non-attachment site of the body include coordinates of the non-attachment site in the coordinate system.

2. The non-transitory computer-readable medium according to claim 1, wherein the sensor data includes an acceleration, the first process includes integration of the acceleration, and the first position information for the attachment sites is obtained by the integration.

3. The non-transitory computer-readable medium according to claim 1, wherein the sensor data includes an acceleration, and the second position information is estimated in regression by using the learning model based on the acceleration.

4. The non-transitory computer-readable medium according to claim 3, wherein
the sensor data further includes an angular velocity, and
the second position information is estimated in regression by using the learning model further based on the angular velocity.

5. The non-transitory computer-readable medium according to claim 4, wherein the acceleration, after being subjected to a coordinate system conversion based on the angular velocity, is used for estimation in regression.

6. The non-transitory computer-readable medium according to claim 4, wherein orientation information for the attachment sites is obtained based on the angular velocity and is used for estimation in regression.

7. The non-transitory computer-readable medium according to claim 4, wherein the acceleration or the angular velocity acquired by the motion sensors is used for estimation in regression.

8. The non-transitory computer-readable medium according to claim 3, wherein the estimation in regression is performed on a basis of position information for the attachment sites previously performed by the estimation in regression.

9. The non-transitory computer-readable medium according to claim 3, wherein an interpolation process estimates in regression, on a basis of the second position information for the attachment sites estimated in regression, position information or orientation information for a non-attachment site to which none of the motion sensors are attached.

10. The non-transitory computer-readable medium according to claim 9, wherein the correction function further corrects the position information or the orientation information for the non-attachment site included in the second position information on a basis of the first position information.

11. The non-transitory computer-readable medium according to claim 1, wherein the executed method further comprises:
implementing a reliability identification function of identifying reliability that indicates reliability of the position information for the attachment sites related to the first positional information or the second positional information.

12. The non-transitory computer-readable medium according to claim 11, wherein the correction function corrects the first position information for the attachment sites on a basis of the reliability identified by the reliability identification function.

13. The non-transitory computer-readable medium according to claim 1, wherein the interpolation function estimates the position information or orientation information for the non-attachment site located between a plurality of the attachment sites in a predetermined skeleton structure.

14. The non-transitory computer-readable medium according to claim 13, wherein the interpolation function estimates the position information or the orientation information for the non-attachment site by regression.

15. The non-transitory computer-readable medium according to claim 1, wherein the correction function is implemented by a Kalman filter.

16. The non-transitory computer-readable medium according to claim 1, wherein the correction function detects a ground contact state and corrects the first position information for the attachment sites on a basis of a detection result.

17. The non-transitory computer-readable medium according to claim 16, wherein the correction function estimates a velocity and a position of a forefoot using an acceleration and an angular velocity included in the sensor data, and detects the ground contact state on a basis of an estimation result, the ground contact state being a state in which the forefoot has a predetermined velocity.

18. An information processor comprising
a corrector that references a first position information obtained by performing a first process on sensor data acquired by two or more motion sensors attached to two or more sites of a body and a second position information estimated by using a learning model on the sensor data, corrects the first position information for attachment sites to which the motion sensors are attached on a basis of the second position information, and implements an interpolation function of estimating, on a basis of the first position information for the attachment sites corrected by the correction function, position information for a non-attachment site of the body to which none of the motion sensors are attached, the position information for the non-attachment site not including the first position information for the attachment sites,
wherein the first position information and the second position information include coordinates of the attachment sites in a coordinate system and the position information for the non-attachment site of the body include coordinates of the non-attachment site in the coordinate system.

19. An information processing method comprising:
referencing, by a processor, a first position information obtained by performing a first process on sensor data acquired by two or more motion sensors attached to two or more sites of a body and a second position information estimated by using a learning model on the sensor data;
correcting, by the processor, the first position information for attachment sites to which the motion sensors are attached on a basis of the second position information; and
implementing an interpolation function of estimating, on a basis of the first position information for the attachment sites corrected by the correction function, position information for a non-attachment site of the body to which none of the motion sensors are attached, the position information for the non-attachment site not including the first position information for the attachment sites,
wherein the first position information and the second position information include coordinates of the attachment sites in a coordinate system and the position information for the non-attachment site of the body include coordinates of the non-attachment site in the coordinate system.

* * * * *